(12) United States Patent
Vig et al.

(10) Patent No.: US 9,259,432 B1
(45) Date of Patent: Feb. 16, 2016

(54) COMPOSITION AND METHODS FOR TARGETED DELIVERY OF A THERAPEUTIC COMPOUND TO THE BRAIN OR SPINAL CORD OF A SUBJECT FOR TREATMENT OF NEURODEGENERATIVE DISEASES

(75) Inventors: Parminder J. S. Vig, Flora, MS (US); Drazen Raucher, Madison, MS (US); Scoty Hearst, Clinton, MS (US)

(73) Assignee: Parminder J. S. Vig, Flora, MS (US)

( * ) Notice: Subject to any disclaimer, the term of this patent is extended or adjusted under 35 U.S.C. 154(b) by 158 days.

(21) Appl. No.: 13/362,729

(22) Filed: Jan. 31, 2012

Related U.S. Application Data

(60) Provisional application No. 61/438,015, filed on Jan. 31, 2011.

(51) Int. Cl.
*A61K 31/704* (2006.01)
*A61K 31/519* (2006.01)
*A61K 31/475* (2006.01)

(52) U.S. Cl.
CPC ............ *A61K 31/704* (2013.01); *A61K 31/475* (2013.01)

(58) Field of Classification Search
None
See application file for complete search history.

(56) References Cited

U.S. PATENT DOCUMENTS

| | | | |
|---|---|---|---|
| 7,892,764 B2 * | 2/2011 | Xiong et al. | 435/7.2 |
| 2003/0211990 A1 | 11/2003 | Sieg et al. | |
| 2004/0152630 A1 * | 8/2004 | Fu et al. | 514/12 |
| 2005/0143310 A1 | 6/2005 | Hirashima et al. | |
| 2007/0092444 A1 * | 4/2007 | Benos et al. | 424/1.69 |
| 2007/0135340 A1 | 6/2007 | Rosenthal et al. | |
| 2007/0265197 A1 | 11/2007 | Furgeson et al. | |
| 2008/0124790 A1 * | 5/2008 | Yang et al. | 435/287.9 |
| 2010/0022466 A1 * | 1/2010 | Raucher et al. | 514/34 |

OTHER PUBLICATIONS

Bidwell et al. Peptides. 31;834-841:2010.*
Rousselle et al. Molecular Pharmacology. 57:679-686 (2000).*
Mackie et al. FEBS Journal. 272:4204-4210 (2005).*
McClintock et al. Journal of Biological Chemistry. 278:6251-6257 (2003).*
Tsuda et al. Cell. 122:633-644 (2005).*
Abdipranoto A, et al. (2008). The role of neurogenesis in neurodegenerative diseases and its implications for therapeutic development. CNS Neurol Disord Drug Targets. Apr.;7(2):187-210.
Tsuda H, et al., (2006) "The AXH Domain of Ataxin-1 Mediates Neurodegeneration through Its Interaction with Gfi-1/Senseless Proteins." Cell, vol. 122, 633-644.
Bidwell GL, 3rd, et al. (2009). Targeting a c-Myc inhibitory polypeptide to specific intracellular compartments using cell penetrating peptides. J Control Release 135:2-10.
Bidwell GL, 3rd, et al. (2007). Development of elastin-like polypeptide for thermally targeted delivery of doxorubicin. Biochem Pharmacol 73:620-631.
Bidwell GL, 3rd, et al. (2010) Cell penetrating elastin-like polypeptides for therapeutic peptide delivery. Adv Drug Deliv Rev 62:1486-1496.
Bidwell GL, 3rd, et al. (2010)A thermally targeted peptide inhibitor of symmetrical dimethylation inhibits cancer-cell proliferation. Peptides 31:834-841.
Burright EN, (1995) SCA1 transgenic mice: a model for neurodegeneration caused by an expanded CAG trinucleotide repeat. Cell 82:937-948.
Charpentier TH, et al. (2010). The effects of CapZ peptide (TRTK-12) binding to S100B-Ca2+ as examined by NMR and X-ray crystallography. J Mol Biol 396:1227-1243.
Custer SK, et al. (2006). Bergmann glia expression of polyglutamine-expanded ataxin-7 produces neurodegeneration by impairing glutamate transport. Nat Neurosci 9(10): 1302-11.
C. de Chiara, C. Giannini, S. Adinolfi, J. de Boer, S. Guida, A. Ramos, C. Jodice, D. Kioussis, A. Pastore, The AXH molecule: an independently folded domain common to ataxin-1 and HBP1. FEBS Letters, vol. 551:1, pp. 107-112, (2003).
Donato R (2001). S100: a multigenic family of calcium-modulated proteins of the EF-hand type with intracellular and extracellular functional roles. Int J Biochem Cell Biol 33:637-668.
Donato R, et al. (2009). S100B's double life: intracellular regulator and extracellular signal. Biochim Biophys Acta 1793:1008-1022.
Dreher MR, et al. (2007) Thermal cycling enhances the accumulation of a temperature-sensitive biopolymer in solid tumors. Cancer Res 67(9):4418-4424.
Drin G, et al. (2002). Peptide delivery to the brain via adsorptive-mediated endocytosis: advances with SynB vectors. AAPS PharmSci, 4(4):E26.
Emamian ES, et al. (2003). Serine 776 of ataxin-1 is critical for polyglutamine-induced disease in SCA1 transgenic mice. Neuron, 38(3):375-87.
Frizzo JK, et al. (2004). S100B-mediated inhibition of the phosphorylation of GFAP is prevented by TRTK-12. Neurochem Res 29:735-740.
Goold R, et al.(2007). Down-regulation of the dopamine receptor D2 in mice lacking ataxin 1. Hum Mol Genet, 16 (17):2122-34.
Griffin WS, et al. (1989). Brain interleukin 1 and S-100 immunoreactivity are elevated in Down syndrome and Alzheimer disease. Proc Natl Acad Sci U S A 86(19):7611-7615.
Hearst SM, et al. (2011). The Design and Delivery of a Thermally Responsive Peptide to Inhibit S100B-Mediated Neurodegeneration, Neuroscience 197: 369-380.
Hearst SM, et al. (2010). Dopamine D2 receptor signaling modulates mutant ataxin-1 S776 phosphorylation and aggregation. J Neurochem 114:706-716.
Hilhorst R, et al. (2009) Peptide microarrays for detailed, high-throughput substrate identification, kinetic characterization, and inhibition studies on protein kinase A. Anal Biochem, 387(2):150-61.
Huttunen HJ, et al. (2000). Coregulation of neurite outgrowth and cell survival by amphoterin and S100 proteins through receptor for advanced glycation end products (RAGE) activation. J Biol Chem 275(51):40096-40105.
Inman KG, et al. (2002). Solution NMR structure of S100B bound to the high-affinity target peptide TRTK-12. J Mol Biol 324:1003-1014.
Kim SJ, et al. (2003). Polyglutamine-expanded ataxin-1 recruits Cu/Zn-superoxide dismutase into the nucleus of HeLa cells. Biochem Biophys Res Commun 307:660-665.

(Continued)

*Primary Examiner* — Amber D Steele
*Assistant Examiner* — Schuyler Milton
(74) *Attorney, Agent, or Firm* — Stites & Harbison PLLC; Mandy Wilson Decker

(57) ABSTRACT

Compositions for targeting to a desired region of the brain or spinal cord include a therapeutic compound useful for the treatment of a neurodegenerative disease; a cell penetrating peptide (CPP); and a thermal targeting polypeptide (TTP).

21 Claims, 14 Drawing Sheets

(56) References Cited

OTHER PUBLICATIONS

Kim SJ, et al. (2003). Oxidative stimuli affect polyglutamine aggregation and cell death in human mutant ataxin-1-expressing cells. Neurosci Lett 348:21-24.

Li, et al. (2001). The Molecular Basis for the Inverse Temperature Transition of Elastin. J Mol. Biol 305:581-592.

Liu Y, et al. (2008) Novel interaction of the dopamine D2 receptor and the Ca2+ binding protein S100B: role in D2 receptor function. Mol Pharmacol, 74(2): 371-8.

Martin E, et al. (2009). High-intensity focused ultrasound for noninvasive functional neurosurgery. Ann Neurol 66:858-861.

Massodi, et al. (2005). Evaluation of cell penetrating peptides fused to elastin-like polypeptide for drug delivery, J Control Release 108:396-408.

Matilla-Duenas A, et al. (2008) Clinical, genetic, molecular, and pathophysiological insights into spinocerebellar ataxia type 1. Cerebellum 7:106-114.

Mod T, et al. (2010) Overexpression of human S100B exacerbates cerebral amyloidosis and gliosis in the Tg2576 mouse model of Alzheimer's disease. Glia 58:300-314.

Sorci G, et al. (2010). S100B Protein, A Damage-Associated Molecular Pattern Protein in the Brain and Heart, and Beyond. Cardiovasc Psychiatry Neurol 2010.

Skinner PJ, et al. (2001). Altered trafficking of membrane proteins in purkinje cells of SCA1 transgenic mice. Am J Pathol 159:905-913.

Vig PJ, et al. (2006). (Glial S100B Positive Vacuoles in Purkinje Cells: Earliest Morphological Abnormality in SCA1 Transgenic Mice. J Neurol Sci Turk 23:166-174.

Vig PJ, et al. (2009). Bergmann glial S100B activates myo-inositol monophosphatase 1 and Co-localizes to purkinje cell vacuoles in SCA1 transgenic mice. Cerebellum 8:231-244.

Vig PJ, et al, (2000). Relationship between ataxin-1 nuclear inclusions and Purkinje cell specific proteins in SCA-1 transgenic mice, J Neurol Sci 174:100-110.

Vig PJ, et al, (1996). Decreased parvalbumin immunoreactivity in surviving Purkinje cells of patients with spinocerebellar ataxia-1, Neurology 47(1):249-253.

Vig PJ, et al. (2011) Glial S100B Protein Modulates Mutant Ataxin-1 Aggregation and Toxicity: TRTK12 Peptide, a Potential Candidate for SCA1 Therapy. Cerebellum.

Vig PJ, et al, (1998) Reduced immunoreactivity to calcium-binding proteins in Purkinje cells precedes onset of ataxia in spinocerebellar ataxia-1 transgenic mice. Neurology, 50(1):106-13.

Vig PJS, (2011). Suppression of Calbindin-D28K Expression Exacerbates SCA1 phenotype in a Disease Mouse Model. Cerebellum, 2011 (Published online, Nov. 11, 2011).

Vig PJS, et al. (2009). Glial response to polyglutamine-mediated stress, Biosci Hypotheses 2 (2009) 148-150.

Vig PJS (2009). S100B—A common connection between depression and cerebellar disorders, Bioscience Hypothesis 2 (2009) 343-344.

Vig et al., "Calcium homeostasis and spinocerebellar ataxia-1(SCA-1)", Brian Research Bulletin, vol. 56, Nos. 3/4, pp. 221-225, (2001).

Wilder PT, et al. (2006). Recognition of the tumor suppressor protein p53 and other protein targets by the calcium-binding protein S100B. Biochim Biophys Acta 1763(11):1284-1297.

Whitaker-Azmitia PM (1997). Transgenic mice overexpressing the neurotrophic factor S-100 beta show neuronal cytoskeletal and behavioral signs of altered aging processes: implications for Alzheimer's disease and Down's syndrome. Brain Res 776(1-2)51-60.

Zoghbi HY et al., (2009) Pathogenic Mechanisms of a Polyglutamine-mediated Neurodegenerative Disease, Spinocerebellar Ataxia Type 1, J Biol Chem 284:7425-7429.

Vig, et al.; Intranasal administration of IGF-I improves behavior and Purkinje cell pathology in SCA 1 mice; Brain Reserach Bulletin 69; 2006; pp. 573-579.

\* cited by examiner

COMPOSITION AND METHODS FOR TARGETED DELIVERY OF A THERAPEUTIC COMPOUND TO THE BRAIN OR SPINAL CORD OF A SUBJECT FOR TREATMENT OF NEURODEGENERATIVE DISEASES

RELATED APPLICATIONS

This application claims priority from U.S. Provisional Application Ser. No. 61/438,015 filed Jan. 31, 2011, the entire disclosure of which is incorporated herein by this reference.

GOVERNMENT INTEREST

Subject matter described herein was made with U.S. Government support under Grant Number RO3NS070065 awarded by the National Institute of Neurological Disorders and Stroke (NINDS) of the National Institutes of Health (NIH). The government has certain rights in the described subject matter.

INTRODUCTION

Neurologic disorders result from the progressive loss of structure, function and death of neurons in the specific regions of the brain and spinal cord. These conditions either cause problems with movements e.g. spinocerebellar ataxias, Huntington and Parkinson's disease, epilepsy and amyotrophic lateral sclerosis or affect memory e.g. Alzheimer's disease and major depression. Most of the recent research has focused on identifying mechanisms that lead to neurodegeneration and therapeutic approaches primarily targeted to prevent neuronal loss or stimulate neurogenesis (Abdipranoto (2008)). However, therapies currently available have had limited success and marketed pharmaceuticals do not have dramatic benefits (Abdipranoto (2008)). Described herein is an innovative therapeutic approach of targeting the central nervous system with therapeutic compounds and peptides of subjects suffering from the above mentioned neurodegenerative diseases.

Interaction between astrocytes and neurons are essential during development and for many critical functions in adult brain. Astrocytes, the most prevalent cell type in brain express receptors for variety of growth factors and neurotransmitters, and are actively involved with neurite growth and control of neuronal activities. Neurons on the other hand, regulate astrocyte function. Studies show that astrocytic glia release the same trophic factors when activated under stress or during normal physiological conditions. There seems to be a delicate balance of events that may lead to the transition from neuroprotection to neurodegeneration (Rojo et al 2007). Glial cells that normally produce the neurotrophic factors required for neurogenesis or neuronal repair when activated by stressing events, might overproduce those factors, triggering the altered pathway to neurodegeneration. Recent evidences suggest that altered signaling patterns between the glia-neuron interactions, activate cellular events common to many neurodegenerative diseases (Rojo et al, 2007).

Temporal lobe epilepsy is a common disorder of the brain, often associated with neuronal loss and gliosis in the regions of the hippocampus (Lewis 1999).

Spinocerebellar ataxias (SCAs) are autosomal dominant neurodegenerative disorders that primarily affect the cerebellum and brain stem, causing progressive ataxia, motor impairment and eventual death. Most SCAs are caused by CAG repeat expansions. In SCA1, the expanded CAG repeat tract in ataxin-1 causes cerebellar Purkinje cells (PCs) to degenerate. The exact mechanism of PC degeneration in SCA1 is not fully understood. There is currently no effective pharmacologic treatment for SCA1 and other SCAs.

The development of therapeutic peptides has advanced rapidly, because these molecules have such diverse activity and show great promise as targeted drugs. An inherent limitation of bioactive peptides, however, is their relative instability, and the delivery of a therapeutic dose proves challenging. As the field of peptide therapy grows, much attention is focused on peptide delivery using macromolecular carriers.

Macromolecular delivery systems are promising strategies to deliver drugs. Micro- and nanospheres are being investigated for their ability to deliver bioactive peptides via the oral route, stabilizing and delivering them through absorption barriers in the gastrointestinal tract. However, nanoparticles do not offer the possibility of thermal targeting. Liposomes have emerged as a major class of macromolecular carriers for drug delivery. Liposome-peptide conjugates have been investigated, but a focus of this field is the conjugation of cell penetrating peptides to the surface of liposomes to enhance fusion with the cell membrane. The use of liposomes to deliver therapeutic peptides, though promising, has not been adequately researched.

To date, liposomes and micro- and nano-particle based drug delivery systems have been developed to improve the therapeutic efficacy of the drug, e.g., chemotherapeutics for the treatment of solid tumors (Allen (1998), Langer (1998), Torchilin (1998), Jones (1999)). Unlike free drugs that have faster plasma clearance and poor selectivity towards tumor cells, macromolecular based drugs display improved pharmacokinetics and better tumor uptake due to enhanced permeability and retention (EPR) of the tumor vasculature (Cassidy (1989), Maeda (1992), Takakura (1990), Yamaoka (1994)). Polymer-delivered drugs also exhibit significantly lower systemic toxicity compared to free drug (Duncan (1998), Seymour (1987), Yeung (1991)), and studies have shown that water soluble polymer carriers can overcome multidrug resistance (St'astny (1999), Ryser (1978), Ohkawa (1993), Minko (1998)).

Thermosensitive liposomes are a technological innovation that employs lipid components with thermal sensitivity in the physiological temperature range. Upon application of hyperthermia, the lipid membrane undergoes a phase transition and becomes more permeable, thus releasing drug that has been loaded inside. This approach has been used successfully to deliver chemotherapeutic drugs, such as methotrexate, cisplatin, doxorubicin, and bleomycin, to solid tumors in animals. However, this approach requires diffusion of the drug out of the liposome under hyperthermic conditions and therefore limits delivery of small and relatively hydrophobic molecules. Therapeutic peptides are too large and hydrophilic to escape the liposomes, even under elevated temperatures.

With recent improvement in the control of power-density, temperature distribution and treatment monitoring by magnetic resonance tomography, which can characterize temperature as well as perfusion, it is possible to heat only a limited and specific target area in a patient and minimize the effects of non-specific toxicity. Consequently, the methods and techniques necessary to employ thermal targeting of thermally sensitive polypeptides are available in the clinical setting.

Therefore, as proposed herein, are compositions and methods for thermally targeted delivery of therapeutic polypeptides to particular regions of the brain for treating conditions of interest.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes a composition including a therapeutic compound, and a method of targeting the therapeutic compound to a desired region of a brain or spinal cord of a subject.

In some embodiments of the presently-disclosed subject matter, the composition includes a therapeutic compound (TC) useful for the treatment of a neurodegenerative disease and a thermal targeting polypeptide (TTP). In some embodiments, the composition further includes a cell penetrating peptide (CPP). In some embodiments, the composition further includes a carrier polypeptide (CP). In some embodiments, the therapeutic compound is a compound useful for the treatment of a neurodegenerative disease. In some embodiments, the therapeutic compound is a therapeutic polypeptide (TP). As such, embodiments of the composition can be represented as follows. TTP-TC; TTP-TP; CCP-TTP-TC, CCP-TTP-TP, CCP-CP-TTP-TC, CCP-CP-TTP-TP, CCP-TTP-CP-TC; and CCP-TTP-CP-TP.

In some embodiments, the TTP comprises an elastin-like polypeptide (ELP), as described herein. In some embodiments, the ELP comprises the sequence $-(VPGXG)_n-$, wherein n is an integer from about 30 to about 240. In some embodiments, each X is independently selected from valine, glycine, and alanine such that the Xs are provided in a 5:3:2 ratio. In some embodiments, each X is independently selected from valine, glycine, and alanine such that the Xs are provided in a 1:7:8 ratio. In some embodiments, each X is independently selected from valine, glycine, and alanine such that the Xs are provided in a 3:1:1 ratio.

As noted, in some embodiments, the composition further includes a CPP. In some embodiments, the CPP is selected from the group consisting of: TAT, Penetratin (Antp), Bac, SynB1, Poly-arginine, VP22, Transportan, MAP, pVEC, MTS, hCT derived, MPG, Buforin 2, PEP-1, Magainin 2, Oct6, and M918. In some embodiments, the CPP is selected from a polypeptide comprising the polypeptides set forth in Table 1. In some embodiments, the CPP comprises the amino acid sequence of RGGRLSYSRRRFSTSTGR (SEQ ID NO: 11).

Methods of targeting a therapeutic compound to a desired region of a brain or spinal cord of a subject include administering to the subject an effective amount of the composition of the presently-disclosed subject matter; and applying heat to a desired region of the brain or spinal cord.

BRIEF DESCRIPTION OF THE SEQUENCE LISTING

Figure 1A:
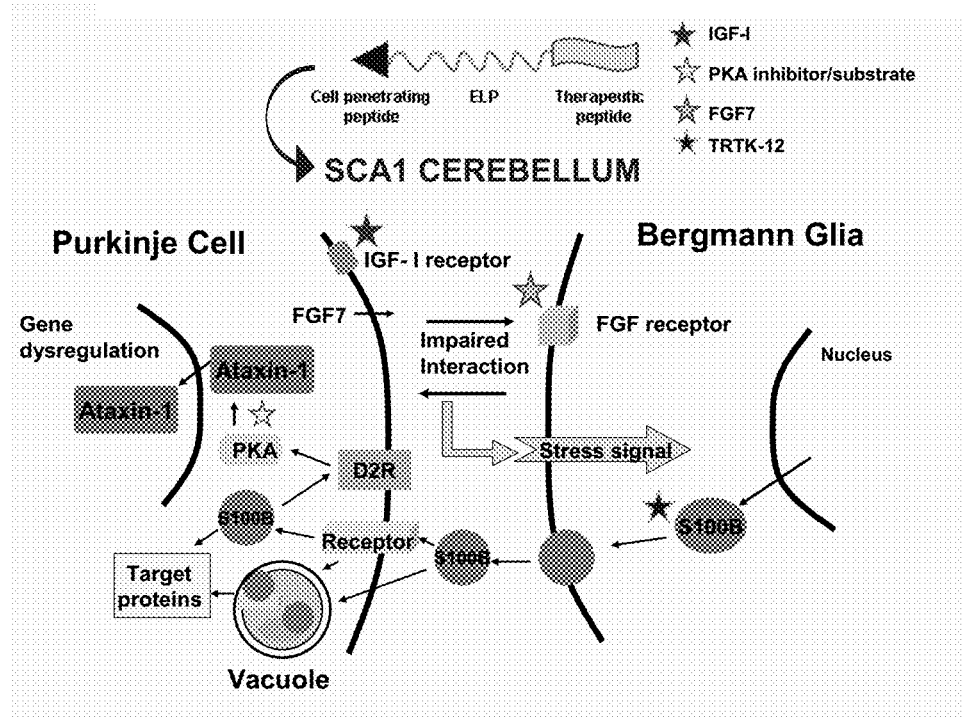
FIG. 1A is Schematic diagram. Without wishing to be bound by theory or mechanism, the diagram of FIG. 1A illustrates events leading to vacuole formation and abnormal spine morphology in Purkinje cells (PCs) in spinocerebellar ataxia 1 (SCA1). Mutant ataxin-1 as a transcriptional repressor early in development dysregulates genes involved in signaling and cell adhesion producing a stress signal to neighboring Bergmann glia (BG). These BG react by releasing high levels of S100B protein. S100B released from BG is internalized by PCs and internalized S100B then interacts with target proteins. The imbalance in S100B-mediated protein regulation leads to vacuole formation. Within PCs, S100B could also activate Dopamine 2 receptor and alter cAMP synthesis and PKA-mediated mutant ataxin-1 phosphorylation. Mutant ataxin-1 phosphorylation is known to stabilize mutant ataxin-1 to form intranuclear aggregates, Stars represent therapeutic targets of different exemplary TPs.

SEQ ID NO: 1 is a unit of an elastin-like polypeptide that includes repeating units of the amino acid sequence VPGXG, where each X is independently selected from valine, glycine, and alanine such that the Xs are provided in a 5:3:2 ratio.

SEQ ID NO: 2 an embodiment of an elastin-like polypeptide that includes repeating units of the amino acid sequence VPGXG, where each X is independently selected from valine, glycine, and alanine such that the Xs are provided in a 5:3:2 ratio.

SEQ ID NO: 3 is a unit of an elastin-like polypeptide that includes repeating units of the amino acid sequence VPGXG, where each X is independently selected from valine, glycine, and alanine such that the Xs are provided in a 1:7:8 ratio.

SEQ ID NO: 4 an embodiment of an elastin-like polypeptide that includes repeating units of the amino acid sequence VPGXG, where each X is independently selected from valine, glycine, and alanine such that the Xs are provided in a 1:7:8 ratio.

SEQ ID NO: 5 is an embodiment of an elastin-like polypeptide that includes repeating units of the amino acid sequence VPGXG, where each X is independently selected from valine, glycine, and alanine such that the Xs are provided in a 3:1:1 ratio.

SEQ ID NO: 6 is an embodiment of an amino acid including a SynB1 cell penetrating polypeptide and an elastin-like polypeptide, including repeating units of the amino acid sequence VPGXG, where each X is independently selected from valine, glycine, and alanine such that the Xs are provided in a 5:3:2 ratio.

SEQ ID NO: 7 is another embodiment of an amino acid including a SynB1 cell penetrating polypeptide and an elastin-like polypeptide, including repeating units of the amino acid sequence VPGXG, where each X is independently selected from valine, glycine, and alanine such that the Xs are provided in a 1:7:8 ratio.

SEQ ID NO: 8 is a Tat cell penetrating polypeptide.
SEQ ID NO: 9 is a Penetratin cell penetrating polypeptide.
SEQ ID NO: 10 is a Bac cell penetrating polypeptide.
SEQ ID NO: 11 is a SynB1 cell penetrating polypeptide.
SEQ ID NO: 12 is a poly-arginine cell penetrating polypeptide including seven (7) arginines.
SEQ ID NO: 13 is a poly-arginine cell penetrating polypeptide including eight (8) arginines.
SEQ ID NO: 14 is a poly-arginine cell penetrating polypeptide including nine (9) arginines.
SEQ ID NO: 15 is a poly-arginine cell penetrating polypeptide including ten (10) arginines.
SEQ ID NO: 16 is a poly-arginine cell penetrating polypeptide including eleven (11) arginines.
SEQ ID NO: 17 is a VP22 cell penetrating polypeptide.
SEQ ID NO: 18 is a Transportan cell penetrating polypeptide.
SEQ ID NO: 19 is a MAP cell penetrating polypeptide.
SEQ ID NO: 20 is a pVEC cell penetrating polypeptide.
SEQ ID NO: 21 is a MTS cell penetrating polypeptide.
SEQ ID NO: 22 is a hCT-derived cell penetrating polypeptide.
SEQ ID NO: 23 is a MPG cell penetrating polypeptide.
SEQ ID NO: 24 is a Buforin 2 cell penetrating polypeptide.
SEQ ID NO: 25 is a PEP-1 cell penetrating polypeptide.
SEQ ID NO: 26 is a Magainin 2 cell penetrating polypeptide.
SEQ ID NO: 27 is an Oct6 cell penetrating polypeptide.
SEQ ID NO: 28 is a M918 cell penetrating polypeptide.
SEQ ID NO: 29 is an R18 therapeutic polypeptide.
SEQ ID NO: 30 is a PKA inhibitor (PKI) therapeutic polypeptide.
SEQ ID NO: 31 is a TRTK12 therapeutic polypeptide.
SEQ ID NO: 32 is the AXH domain of ataxin-1.
SEQ ID NO: 33 is a ASIC inhibitory Psalmotoxin 1 polypeptide.
SEQ ID NO: 34 is cannabinoid receptor agonist polypeptide. (CB1V).
SEQ ID NO: 35 is cannabinoid receptor agonist polypeptide. (CB1R).
SEQ ID NO: 36 is a dopamine receptor peptide (D2R-IC3-N25) carrier polypeptide.
SEQ ID NO: 37 is a dopamine receptor peptide (D2R-IC3-M28) carrier polypeptide.
SEQ ID NO: 38 is a dopamine receptor peptide (D2R-IC3-C30) carrier polypeptide.
SEQ ID NO: 39 is a dopamine receptor peptide (D2R-IC3-C58) carrier polypeptide.
SEQ ID NO: 40 is a dopamine receptor peptide (D2R-IC3) carrier polypeptide.

DESCRIPTION OF EXEMPLARY EMBODIMENTS

The presently-disclosed subject matter includes a composition for targeted delivery of a therapeutic compound to a particular region of the brain or spinal cord (e.g., cerebellum, hippocampus, frontal cortex, substansia nigra, striatum, and spinal cord, e.g., motor neurons of spinal cord) of a subject for treatment of neurodegenerative diseases, and a method for use thereof. Examples of relevant neurodegenerative diseases include, but are not limited to CNS diseases involving cerebellum, cerebellar ataxias, and spinocerebellar ataxias (SCAs), including spinocerebellar ataxia 1 (SCA1), spinocerebellar ataxia 2 (SCA2), spinocerebellar ataxia 3 (SCA3), and spinocerebellar ataxia 6 (SCA6). Further examples of neurodegenerative diseases of relevance include, but are not limited to, Alzheimer's disease, and Down syndrome, traumatic brain injury. In some embodiments, the region of the brain that is targeted is the cerebellum. In other embodiments, other brain regions and/or regions of the spinal cord can be targeted, e.g., temporal lobe in temporal lobe epilepsy or frontal cortex in depression.

As used herein, the term "subject" refers to a target of administration. The subject of the herein disclosed methods can be a human or non human animal. Thus, veterinary therapeutic uses are provided in accordance with the presently disclosed subject matter. As such, the presently disclosed subject matter provides for administration to mammals such as humans and non-human primates, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; rabbits, guinea pigs, and rodents. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

In some embodiments, the composition comprises: a therapeutic compound and a thermal targeting polypeptide (TTP). In some embodiments, the composition further comprises a cell penetrating polypeptide (CPP). In some embodiments, the composition further comprises a carrier polypeptide (CP). In some embodiments, the therapeutic compound can be selected from a therapeutic polypeptide (TP), a drug, an antibiotics, and a nucleotide molecule (e.g., siRNA). In some embodiments, the composition can be administered to a subject for delivery to a region of the brain or spinal cord to which local hyperthermia has been applied. In some embodiments, the composition can be administered to a subject for delivery to the cerebellum, to which local hyperthermia has been applied.

The earliest morphologic change seen in SCA1 Purkinje cells (PCs) is the presence of cytoplasmic vacuoles rich in proteins that normally localized to Bergmann glia (BG). These vacuoles are toxic, as PC with vacuoles exhibit abnormal development of dendritic spines. The present inventors observed that the treatment of SCA1 transgenic (Tg) mice with the neurotrophic factor IGF-I improves the SCA1 phenotype, and the present inventors proposed peptide therapies for treatment for this disorder. Described herein are compositions and methods that can target SCA PCs using therapeutic peptides (TPs) that directly influence PC growth and signaling, alter mutant ataxin-1 protein phosphorylation, and/or modulate PC-Bergmann glia (BG) interactions.

Therapeutic Polypeptides (TPs) are promising because they can be designed to inhibit specific molecular interactions; however, their efficacy in vivo is limited by poor pharmacokinetic parameters. To improve their pharmacokinetics and bio-distribution, as described herein, the present inventors have selected TPs and fused them to a thermal targeting polypeptide (TTP). The resulting composition can be targeted to the cerebellum of a subject by applying local hyperthermia.

As used herein, the term "polypeptide" means any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted.

With regard to the thermal targeting polypeptide (TTP) of the composition, as used herein, TTP refers to a polypeptide that can preferentially direct the composition to the target (cerebellum) to which local hyperthermia has been applied. At a characteristic temperature called the transition temperature ($T_t$), the TTP hydrophobically collapses and aggregates. This property can be exploited for thermally targeted delivery of the TTP-containing composition.

The composition of the presently-disclosed subject matter can be administered (e.g., intravenously (IV), intranasally (IN), intraperitoneally (IP)) to a subject. In some embodiments, when hyperthermia has not been applied to the target, the composition will have a lower blood concentration and will be rapidly cleared under physiological conditions, wherein $T<T_t$, where T is the temperature of the target, and $T_t$ is the transition temperature of the TTP. When heat is applied to the target, i.e., when $T>T_t$, than the composition will aggregate and accumulate at the heated site, i.e., the target to which local hyperthermia has been applied.

Embodiments of the composition will pass the blood brain barrier (BBB), accumulate in cells (PCs), and can improve motor coordination and/or cerebellar pathology in an animal (e.g., subject; SCA1 mouse model).

In some embodiments, the TTP can include an elastin-like polypeptide (ELP). In some embodiments, the ELP is an approximately 60 kilodalton protein composed of repeated units of the amino acid sequence VPGXG. In some embodiments, the ELP can comprise the amino acid sequence $(VPGXG)_n WP$ or $(VPGXG)_n$, where each X is independently selected from valine, glycine, and alanine, as described herein. In some embodiments, n is about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 230, 231, 232, 233, 234, 235, 236, 237, 238, 239, or 240.

In some embodiments, the composition of the presently-disclosed subject matter comprises the following:

[Cell Penetrating Peptide]–(VPGXG)$_n$–[Therapeutic Polypeptide]

where n represents the number units of VPGXG repeats (for example, where n=30, there are thirty (30) units of VPGXG repeats to yield the following amino acid sequence VPGXG VPGXG VPGXG VPGXG VPGXG VPGXG VPGXG VPGXG VPGXG VPGXG VPGXG VPGXG VPGXG VPGXG VPGXG VPGXG VPGXG VPGXG VPGXG VPGXG VPGXG VPGXG VPGXG VPGXG VPGXG VPGXG VPGXG VPGXG VPGXG VPGXG).

In some embodiments, the TTP can include an elastin-like polypeptide (ELP). In some embodiments, the ELP is an approximately 60 kilodalton protein composed of repeated units of the amino acid sequence VPGXG, where X is Val, Gly, and Ala in a 5:3:2 ratio (referred to herein as ELP1).

In some embodiments, the TTP is an approximately 63 kilodalton protein composed of repeated units of the amino acid sequence VPGXG, where X is Val, Gly, and Ala in a 1:7:8 ratio, respectively (referred to herein as ELP2).

In some embodiments, the TTP is an approximately 20, 40, 60, 80, 120, or 160 kilodalton protein composed of repeated units of the amino acid sequence VPGXG, where X is Val, Gly, and Ala in a 3:1:1 ratio, respectively.

In some embodiments, the TTP is an ELP having a $T_t$=40-42° C. In some embodiments, the TTP is an ELP as described in U.S. Patent Application Publication No. 2005/0255554 of A. Chilkoti, which is incorporated herein by this reference, together with all polypeptide sequences and information regarding ELPs as disclosed therein.

In some embodiments, the compositions of the presently-disclosed subject matter include a cell penetrating polypeptide. As used herein, the term "cell penetrating polypeptide" (CPP) refers to a polypeptide that facilitates transport of the composition through a cell membrane or facilitates the delivery of the polypeptide across the blood brain barrier (BBB). Cell penetrating peptides can be short polypeptides capable of mediating delivery of molecules across the plasma (cell) membrane. In some embodiments, CPPs can be comprised of mostly basic amino acids, hydrophobic amino acids, or an amphipathic sequence. In some embodiments, the CPP can be a TAT polypeptide from HIV-1, apegelin-based peptide SynB1, a bactenecin-derived Bac peptide, or an Antennapedia-derived penetratin peptide. The CPP can be selected, for example, to achieve a desired level of accumulation of the composition in the cerebellar tissue of a subject receiving the composition. Examples of CPPs that can be used in accordance with the presently-disclosed subject matter include, but are not limited to, those set forth in Table 1.

TABLE 1

| CPP Name | Sequence | SEQ ID NO: |
|---|---|---|
| TAT | YGRKKRRQRRR | 8 |
| Penetratin (Antp) | RQIKIWFQNRRMKWKK | 9 |
| Bac | RRIRPRPPRLPRPRPRPLPFPRPG | 10 |
| SynB1 | RGGRLSYSRRRFSTSTGR | 11 |
| Poly-arginine | e.g., (R)$_{7-11}$ | 12, 13, 14, 15, 16 |
| VP22 | DAATATRGRSAASRPTQRPRAP ARSASRPRRPVQ | 17 |
| Transportan | GWTLNSAGYLLGKINLKALAALAKKIL | 18 |
| MAP | KLALKLALKALAALKLA | 19 |
| pVEC | LLIILRRRIRKQAHAHSK | 20 |
| MTS | AAVALLPAVLLALLP | 21 |
| hCT derived | LGTYTQDFNKFHTFPQTAIGVGAP | 22 |
| MPG | GALFLGFLGAAGSTMGAWSQPKKKRKV | 23 |
| Buforin 2 | TRSSRAGLQFPVGRVHRLLRK | 24 |
| PEP-1 | KETWWETWWTEWSQPKKKRKV | 25 |
| Magainin 2 | GIGKFLHSAKKFGKAFVGEIMNS | 26 |
| Oct6 | GRKRKKRT | 27 |
| M918 | VTVLFRRLRIRRASGPPRVRV | 28 |

In some embodiments, the composition further includes a carrier polypeptide (CP). In some embodiments, the CP can be disposed between the cell penetrating polypeptide (CPP) and the thermal targeting polypeptide (TTP), as follows:

CPP-CP-TTP-TC.

In some embodiments, the CP can be provided between the TTP and the therapeutic compound, as follows:

CPP-TTP-CP-TC.

Without wishing to be bound by theory or mechanism, to target Purkinje cells of the cerebellum and enhance peptide delivery, it is contemplated that the carrier polypeptide could be selected to be a dopamine receptor polypeptide (D2R). In some embodiments, the carrier polypeptide could be an amino acid sequence taken from the IC3 loop region peptide sequences. (Dempsey and Shaw, Biochemistry 2011, 50, 9056-9065). Without wishing to be bound by theory or mechanism, S100B binding to the D2R is localized to the C-terminus of the IC3 loop and is calcium independent binding (contrast with TRTK binding to S100B, which is calcium dependent).

Without wishing to be bound by theory or mechanism, in some embodiments of the presently-disclosed subject matter that include a carrier polypeptide, the carrier polypeptide can target the composition to the targeting region. As such, in some embodiments, the TTP plus heat provides once source of targeting action, while the carrier polypeptide can provide another source of targeting action.

Furthermore, and without wishing to be bound by theory or mechanism, in some embodiments, the carrier polypeptide can provide a therapeutic benefit. For example, in treating Parkinson disease, an IC3 sequence (as described herein) can bind dopamine transporter (DAT) and and enhance presynaptic levels of dopamine by inhibiting dopamine binding to DAT. In addition, within the cytosol an ELP-IC3 component of embodiments of the composition can interact with transported DAT and inhibit DAT binding to dopamine receptors, which could be useful in cases of dopamine receptor sensitization and regulation.

Examples of such carrier polypeptides which can be used in connection the presently-disclosed subject matter can comprise the D2R polypeptides set forth in SEQ ID NOS: 36-40. In some embodiments the carrier polypeptide can be selected from a fragment of the amino acid sequence of SEQ ID NO: 40. In some embodiments the carrier polypeptide can comprise a fragment of the amino acid sequence of SEQ ID NO: 40 including 15 or more amino acids and extending from amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, or 119 and extending to 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, and 129.

In some embodiments, other appropriate amino acid sequences can be used; for example, the carrier polypeptide can comprise a fragment of any one of SEQ ID NOS: 36-40, wherein the fragment begins with methionine, asparagine, or cystein, and is about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, or 58 amino acids in length.

In some embodiments, the D2R polypeptides can be provided between the cell penetrating peptide and the thermal targeting polypeptide (e.g., CPP-D2R-TTP-TC). In some embodiments, the D2R polypeptides can be provided between the thermal targeting polypeptide and the therapeutic compound (e.g., CPP-TTP-D2R-TC). Without wishing to be bound by theory or mechanism, it has been shown that S100B interacts with D2R, downregulates receptor activity and localizes to PC vacuoles, but all that happens in the cytosolic side. The D2R polypeptides can bind to S100B extracellularly or at S100B release sites. It is contemplated that such embodiments of the presently-disclosed subject matter have the advantage of being able to deliver cargo to all other dopamine neurons, e.g., SN in Parkinson's Disease.

As noted herein above, in some embodiments of the composition, the therapeutic compound is a therapeutic polypeptide (TP). As used herein, the term "therapeutic polypeptide" refers to a polypeptide capable of acting upon a target and affecting treatment of a neurodegenerative disease of interest. For example, in some embodiments, the therapeutic polypeptide is a polypeptide that is capable of influencing Purkinje cell (PC) growth and/or signalling, stimulating transcriptional activity of wildtype ataxin-1, inhibiting mutant ataxin-1 protein phosphorylation, and/or modulating Purkinje cell (PC)-Bergmann glia (BG) interactions. In some embodiments, the therapeutic polypeptide is known to be useful for the treatment of a neurodegenerative disease, but has limited utility, for example, due to poor bioavailability when administered alone. In this regard, the presently-disclosed subject matter can be used to salvage promising therapeutic polypeptides that were abandoned due to complications such as limited bioavailability upon administration.

As used herein, the terms "treatment" or "treating" relate to any treatment of a neurodegenerative disease of interest (e.g., spinocerebellar ataxias (SCAs)), including but not limited to prophylactic treatment to prevent development or reduce severity of the disease. As such, the terms treatment or treating include, but are not limited to: preventing a neurodegenerative disease of interest or the development of a neurodegenerative disease of interest; inhibiting the progression of a neurodegenerative disease of interest; arresting or preventing the development of a neurodegenerative disease of interest; reducing the severity of a neurodegenerative disease of interest; ameliorating or relieving symptoms associated with a neurodegenerative disease of interest; and causing a regression of the neurodegenerative disease of interest or one or more of the symptoms associated with the neurodegenerative disease of interest.

A therapeutic polypeptide can be designed and/or selected for efficacy, e.g., a known efficacy. As will be recognized by those skilled in the art, in some embodiments, the selected therapeutic polypeptide (TP) can attached to the TTP. In some embodiments, the composition can further include a CCP. For example, as shown in FIG. 1, an exemplary composition includes a CCP, a TTP that is an ELP, and a therapeutic polypeptide. In some embodiments, the composition can further include a carrier polypeptide (CP). In some embodiments, multiple TPs can be selected for use in the presently-disclosed composition.

Examples of TPs that can be used in the presently-disclosed subject matter include, but are not limited to: IGF-I, which is a neurotrophic factor for PCs; FGF7, which has receptors on BGs and enhances cell adhesion and signaling; a PKA inhibitory polypeptide (PKI), which blocks PKA, preventing its stabilization and nuclear accumulation; a PKA substrate peptide, which competes with mutant ataxin-1, preventing PKA stabilization and nuclear accumulation; TRTK-12, a peptide which binds S100B and interferes with S100B binding to PC receptors and/or induces vacuole formation; R18, a 14-3-3 nonphospharylated inhibitor polypeptide; a polypeptide having the sequence of an AXH domain of ataxin-1 or fragment thereof (See the amino acid sequence disclosed in, C. de Chiara, C. Giannini, S. Adinolfi, J. de Boer, S. Guida, A. Ramos, C. Jodice, D. Kioussis, A. Pastore, The AXH molecule: an independently folded domain common to ataxin-1 and HBP1. FEBS Letters, Vol. 551:1, pp. 107-112, where are all incorporated herein by this reference); and an ASIC inhibitory Psalmotoxin 1 polypeptide; a cannabinoid receptor agonist polypeptide. Further examples of TPs that can be used in the presently-disclosed subject matter include, but are not limited to the polypeptides comprising the amino acid sequences set forth in SEQ ID NOS: 29-35. In some embodiments, the TP can have an amino acid sequence comprising the amino acid sequence of SEQ ID NO: 32 or a fragment thereof. In some embodiments, the TP can have an amino acid sequence comprising residues 7-126 of SEQ ID NO: 32 or a fragment thereof. In some embodiments, the TP can have an amino acid sequence comprising the amino acids of residues 750-689 of normal human ataxin 1 (See, de Chiara, et al., FEBS Letters, Vol. 551:1, pp. 107-112).

In some embodiments, the TP can be a fragment of Psalmotoxin 1. In some embodiments, the TP can be a fragment of the polypeptide of SEQ ID NO: 33. In some embodiments, the fragment can be about 10, 11, 12, 13, 14, or 15 amino acids in length. In some embodiments, the fragment can be about 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 amino acids in length.

Figure 1B:
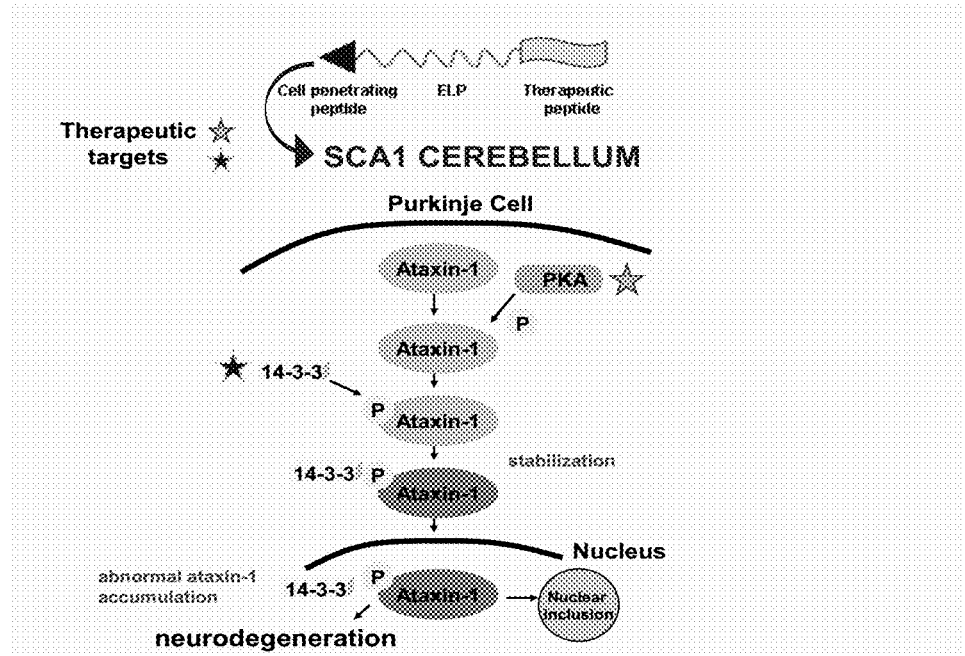
FIG. 1B is another Schematic diagram, which shows ataxin-1 accumulation in SCA1 PCs and the therapeutic targets of the compositions of the presently-disclosed subject matter.

In some embodiments, the TP can be selected such that ataxin-1 is directly targeted. With reference to FIG. 1A, mutant ataxin-1 is phosphorylated by protein kinase A (PKA) and stabilized by binding of the 14-3-3 protein to resist degradation. This leads to a toxic accumulation of ataxin-1 in the nuclei of, for example, SCA1 PCs. With reference to FIG. 1B, the over-expressed mutant ataxin-1 makes nuclear inclusions both in cell culture and an animal (mouse) model. Therefore, SCA1 PCs can be targeted with therapeutic peptides (TPs) that will directly influence ataxin-1 phosphorylation, stabilization, and aggregation. Further examples of TPs that can be used in the presently-disclosed subject matter include, but are not limited to the following. A PKA inhibitory peptide can be used, which binds to the active site of, and a substrate peptide that competes with, ataxin-1 (See, Hilhorst, et al. (2009)). Further, two peptides can be used, which will interact with 14-3-3 and modulate its binding to mutant ataxin-1 (See, Mackie and Aitken (2005)).

The presently-disclosed subject matter further includes a pharmaceutical composition, including the composition as described herein, and also including at least one component selected from the group consisting of: a pharmaceutically acceptable carrier, a pharmaceutically acceptable adjuvant, and/or a diluent.

The presently-disclosed subject matter further includes a method of treating a neurodegenerative disease in a subject, which includes administering to the subject an effective amount of the composition or pharmaceutical composition as described herein. In some embodiments of the method, the composition is thermally targeted to a region of interest in the brain or spinal cord of the subject. In some embodiments of the method, the composition is thermally targeted to the cerebellum of the subject. In some embodiments the composition is thermally targeted to the region of interest by applying heat to the region of interest. In some embodiments, the neurodegenerative disease is selected from: Alzheimer's disease, amyotrophic lateral sclerosis, cerebellar ataxias, depression, Down syndrome, epilepsy, Huntington disease, Parkinson's disease, spinocerebellar ataxias, essential tremor, autism, west nile neuropathy and traumatic brain injury. In some embodiments, the neurodegenerative disease is a cerebellar ataxias. In some embodiments, the neurodegenerative disease is a spinocerebellar ataxia (SCA). In some embodiments, the SCA is SCA1.

The presently-disclosed subject matter further includes a method of targeting a therapeutic compound to a desired region of a brain or spinal cord of a subject, including administering to the subject an effective amount of a composition of the presently-disclosed subject matter and applying heat to a desired region of the brain or spinal cord. In some embodiments the subject is identified as having or being at risk of having a condition of interest. In some embodiments the method includes identifying a condition of interest in the subject, or a risk thereof, prior to administration of the composition. In some embodiments the condition of interest is selected from: Alzheimer's disease, amyotrophic lateral sclerosis, cerebellar ataxias, depression, Down syndrome, epilepsy, Huntington disease, Parkinson's disease, spinocerebellar ataxias, and traumatic brain injury.

Targeting a composition to a region of interest, or applying heat to a region of interest, can be accomplished using various tools known to those of ordinary skill in the art, including, but not limited to: microwave, radiofrequency, high intensity focused ultrasound, laser, etc. In some embodiments, the thermal targeting and/or application of heat can be accomplished using a Laser Head of Mettler Laser System 540 (Mettler Electronics, Anaheim, Calif., USA).

The presently-disclosed subject matter further includes systems and kits for targeting a therapeutic compound to a desired region of a brain or spinal cord of a subject, comprising a composition or pharmaceutical composition as described herein, and further optionally including include means for administering the composition or pharmaceutical composition. As will be recognized by those skilled in the art upon review of this application, means for administration will be apparent depending on the desired mode of administration. For example, for administration by injection, a syringe could be included. For other examples, for topical administration, a patch could be included; for oral administration, a consumable liquid or container appropriate for holding a consumable liquid could be included to aide the oral administration; for nasal delivery, a nasal spray device or cotton swab could be included to aide the nasal administration; etc. Embodiments of the systems and kits can additionally include means for applying heat to a target site, as described hereinabove.

As will become apparent to those skilled in the art upon studying the present application, the compositions disclosed herein have one or more of the following advantages: (1) The compositions are thermally responsive and can be targeted to a desired region of the brain or spinal cord by applying local hyperthermia; (2) The thermal targeting polypeptide (TTP) component of the compositions can be expressed in *E. coli*, and large quantities can be purified by simple thermal cycling, which strategy is not possible when using drugs linked to polymers that must be chemically synthesized; (3) Because the TTP component of the composition is genetically encoded, the coding sequence can be readily modified, which allows easy modification of the transition temperature ($T_t$) or addition of drug reactive groups; (4) In addition to being targeted to specific location by focused hyperthermia, an additional level of specificity can be achieved by targeting disease-causing proteins often functioning aberrantly in polyglutamine diseases involving cerebellum; (5) The presently-disclosed subject matter can be used to deliver a therapeutic molecule across the BBB and reach appropriate molecular target in a thermally targeted manner.

Because the composition of the presently-disclosed subject matter provides for the enhanced bioavailability of the therapeutic compound, the technology is useful for salvaging active agents that have shown great potential for efficacy, but which have undesirable side effects when administered generally to a subject. It is recognized that the present technology can allow for lower doses of the active agent to be administered to affect a result, relative to general administration of an untargeted active agent.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Example 1

SCA1 was used in this study as a neurodegenerative disease model. Spinocerebellar ataxia-1 (SCA1) is a devastating neurological disorder resulting from CAG repeat expansion in the ataxin-1 gene. The polyglutamine expanded mutant ataxin-1 primarily targets Purkinje cells (PCs) of the cerebellum. The exact mechanism of PC degeneration in SCA1 is poorly understood, but it is known that the earliest morphologic change seen in SCA1 PCs is the development of cytoplasmic vacuoles that contain Bergmann glial (BG) proteins, especially S100B. These vacuoles are toxic, resulting in the abnormal development of dendritic spines. In addition, vacuoles may form in response to a stress signal of PCs. Further, S100B released by BG or from the vacuoles may modulate Akt phosphorylation of mutant ataxin-1. Akt is known to stabilize mutant ataxin-1 to aggregate in the nucleus of PCs.

An objective is to target SCA1 PCs with therapeutic peptides (TPs) that will directly influence ataxin-1 aggregation and toxicity. Though TPs are designed to inhibit specific molecular interactions, their efficacy in vivo is limited by poor pharmacokinetic parameters. To improve their pharmacokinetics and bio-distribution, TPs will be fused to a thermally responsive polypeptide-based carrier. This polypeptide can be targeted to the cerebellum of Tg mice by applying local hyperthermia. The amino acid sequence of the thermally responsive polypeptide is based on elastin-like polypeptide (ELP) biopolymers, which are soluble in aqueous solution below physiological temperature, but aggregate when the temperature is raised above 41° C. A cell-penetrating peptide (CPP) will be conjugated to the ELP to enhance delivery of the polypeptide across the blood brain barrier (BBB) and to facilitate cell entry. The TAT and SynB1 peptides will be used in this study: To the CPP-ELP, two different TPs will be conjugated: (1) a peptide which inhibits Akt activity by directly binding to the active site and (2) a peptide which binds and inhibits S100B. TPs will be administered intranasally (IN) and intravenously (IV) and, by applying local hyperthermia, it will be demonstrated that these polypeptides can be targeted to the cerebellum and improve motor coordination and cerebellar pathology in a SCA1 mouse model.

To investigate the role of S100B in SCA1 pathology, a selective thermally responsive S100B inhibitory peptide was designed, Synb1-ELP-TRTK. The exemplary therapeutic polypeptide was developed using three key elements: (1) an elastin-like polypeptide (ELP), a thermal targeting polypeptide, (2) TRTK12 peptide, a known S100B inhibitory peptide, and (3) a cell penetrating peptide, Synb1, to enhance the intracellular delivery. Using fluorescent quenching techniques, it was shown that the Synb1-ELP-TRTK peptide has a similar S100B binding affinity as compared to the TRTK12 peptide alone. In addition, in vitro studies revealed that Synb1-ELP-TRTK treatment reduces S100B uptake in SHSY5Y cells. Further, to deliver therapeutic peptides to the SCA1 cerebellum, mice were treated with fluorescent labeled Synb1-ELP and it was observed that the labeled polypeptide can be localized to the cerebellum by IP injection. Overall, these data show that thermal targeting of Synb1-ELP-TRTK to the cerebellum to reduce S100B neurotoxicity.

Example 2

Figure 2:
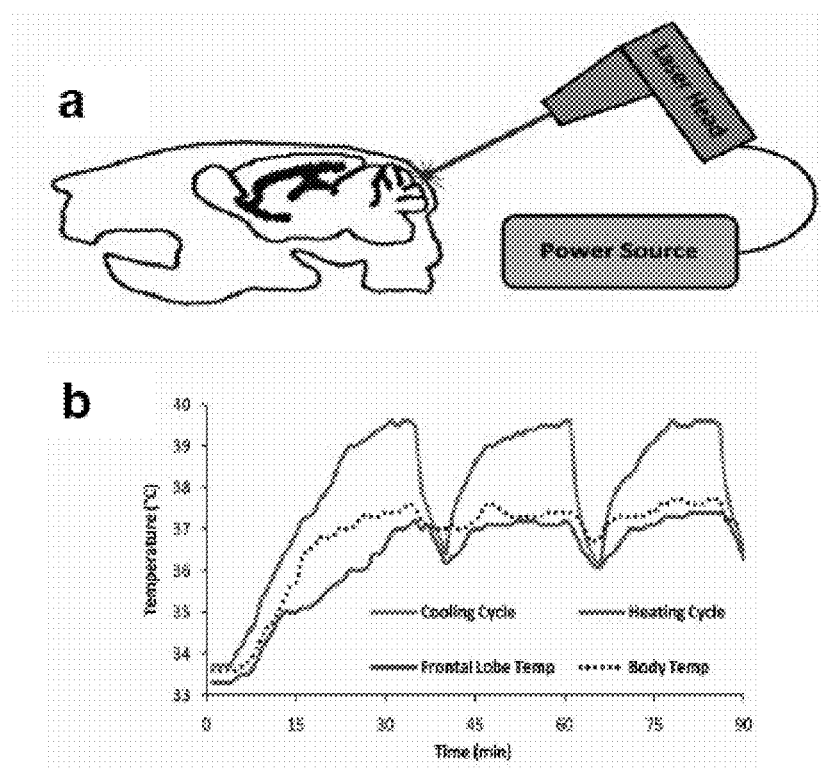
FIG. 2A is Schematic diagram of a mouse skull and brain demonstrating the use of laser system to heat the cerebellum. The laser head is attached to a power source that controls laser output.
FIG. 2B shows the results of a thermal cycling procedure, where the mouse cerebellum was targeted and changes in temperature of the cerebellum, frontal lobe and body temperature were monitored during a thermal cycling procedure.

Innovative non-invasive procedure of inducing hyperthermia in different regions of the brain. An embodiment of the method disclosed herein was conducted using the Laser Head of Mettler Laser System 540 (Mettler Electronics, Anaheim, Calif., USA). The Mettler 540 Laser System and the Mettler 540 Laser Applicator is a safe light/heat therapy device currently used in clinics on humans. This Laser device has a Wavelength of 785 nm with a Power of 80 mW. Elliptical beam spot is 2.8 mm×1.1 mm (elliptical beam area of =9.2 mm$^2$) at the laser head aperture. Eye protection is recommended (e.g., Uvex glasses with a minimum of 80% attenuation in the wavelength range of 780 nm to 860 nm that were supplied with the Mettler 540 system). General anesthesia techniques (isoflurane or ketamine) are used to anethesize the animals. Next, the animals have their hair gently removed from the back of the head just above the cerebellum (FIG. 2A). Then, the cerebellum is heated to a temperature no higher than 40° C. using the Mettler 540 Laser Applicator. The goal is to heat the cerebellum for three heating cycles maintaining a temperature range from 39-40° C. for 20 minutes during each cycle. Between each heating cycle, there is 10 minute cooling period where the laser is turned off and the cerebellar temperature drops. This heating technique effectively accumulate the therapeutic ELP based peptides at the cerebellum. Similar procedure could be used to apply heat to the other brain and spinal cord regions. After the treatment, the animal are allowed to recover from anesthesia.

With reference to FIG. 2B, a male 3 wk old FVB mouse was anesthetized with isoflurane. Then, the animal's head was shaved to expose the scalp for proper light penetration. A small hole was punctured in the skull behind the right ear using a 25 gauge needle. Next, a temperature sensitive probe was gently inserted midway into the cerebellum. Also, a small hole was punctured in the skull just above the right frontal lobe and another temperature probe was gently inserted. The top of the head directly above the cerebellum was heated with a 8 mW 785 nm Mettler class 3B laser using a thermal cycling procedure of: 30 minutes of heating followed by 5 minutes followed by two additional cycles of 20 minutes of heating and 5 minutes of cooling. The graph of FIG. 2B shows the temperature of the cerebellum during Cooling Cycles in blue and Heating Cycles in red. Shown as the black dotted line, is the body temperature taken with a rectal thermometer over the course of the 90 minute experiment. The Frontal Lobe temperature taken over the course of the 90 minute experiment is shown by the gray line. Interestingly, over the thermal cycling procedure a cerebellum temperature greater than 39° C. was able to be reached during each heating cycle, while maintaining a lower 2 degree difference in the frontal lobe temperature and the body temperature. This evidence supports the idea that the cerebellum can be thermally targeted for ELP delivery while limiting the thermal effect to other regions of the brain.

Figure 3:
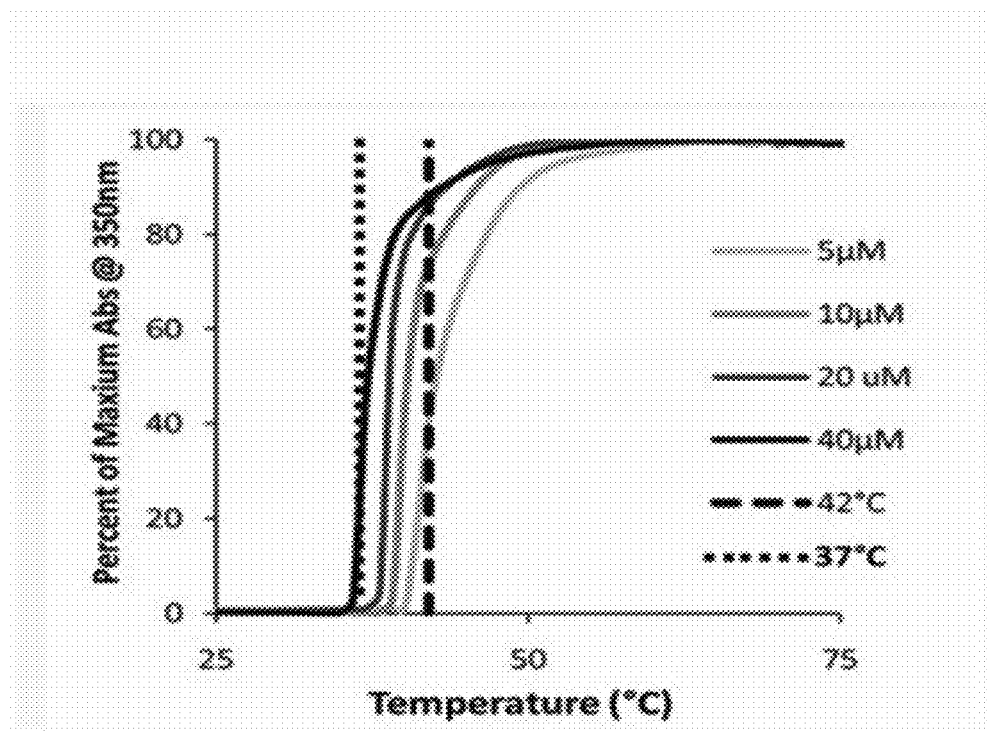
FIG. 3 shows the transition of Synb1-ELP-GGC aggregation from 25° to 75°.
Figure 4:
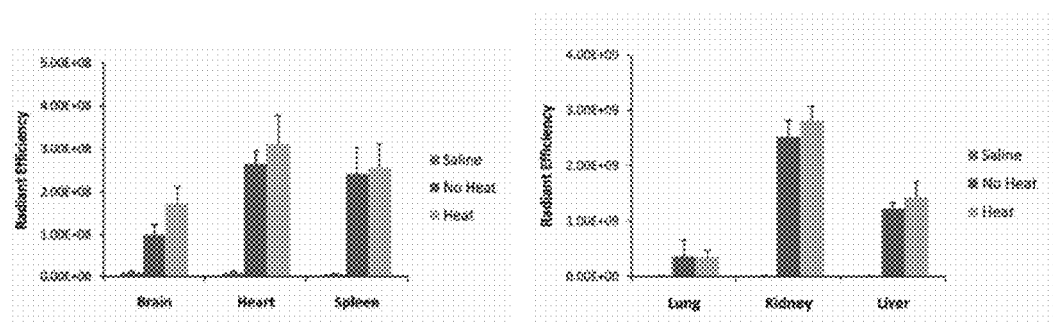
FIG. 4 shows the Synb1-ELP-GGC average radiant efficiency of the brain, heart, spleen (left panel; and lungs, kidney, and liver (right panel) ±SE taken from a control animal, an unheated animal, and an animal where the cerebellum was heated by thermal cycling, n=3.

ELP based polypeptides are designed to be soluble at body temperature (37° C.), and to aggregate and concentrate at a transition temperature between 39-42° C. Heating ELP fused peptides above 37° C. cause a transition in protein solubility (FIG. 3) which helped concentrate ELPs to a particular location in vivo. The biodistribution of Synb1-ELP-GGC (Synb1-ELP-Gly-Gly-Cys) in the brain, heart, spleen (FIG. 4 (left panel)), lung, kidney, and liver (FIG. 3 (right panel)) from control animals, unheated animals, and animals where the cerebellum was heated by thermal cycling were observed. It was found that heating the brain had no significant effect on Synb1-ELP-GGC levels in the various organs analyzed. However, there appears to be an increase in the total brain uptake in animals where the cerebellum was heated compared to unheated animals; however, the increase was not significant (FIG. 4). The increase in brain uptake is most likely due to the enhanced localization of Synb1-ELP-GGC to the cerebellum induced by the focused hyperthermia. The results are a unique finding, as ELP peptide transport into the brain has never been studied. Overall, it was found that thermal targeting by applying local focused hyperthermia significantly increased Synb1-ELP-GGC localization to the cerebellum. This is the first evidence demonstrating that ELP-based therapeutics can be thermally targeted to a particular region of the brain to combat neurodegenerative diseases as well as other CNS diseases. The ELP delivery system can be modified to accommodate a large repertoire of cargo, including peptides, drugs, or DNA, to treat a multitude of CNS diseases making a huge impact on the neurodegenerative field (Bidwell and Raucher, 2005, 2009; Bidwell et al., 2007; Chen et al., 2008; MacKay et al., 2009; Raucher et al., 2009).

Figure 5:
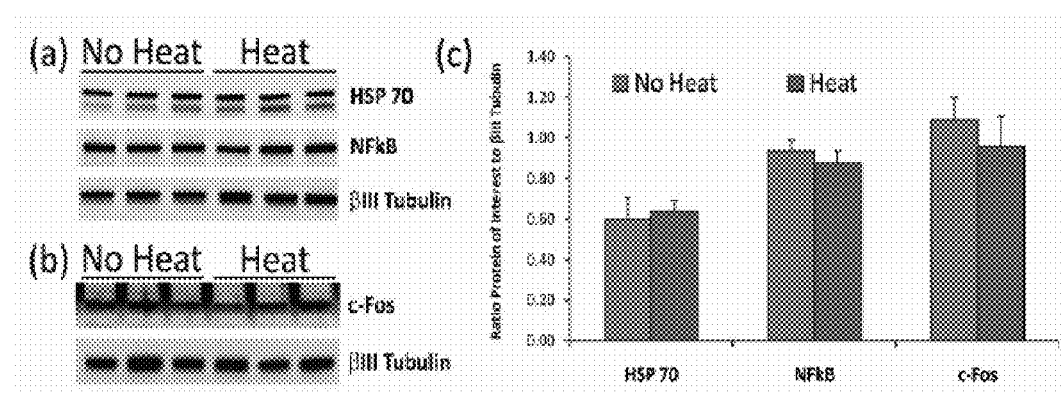
FIG. 5 includes the following: (a) Western blot of HSP70, NFkB and βIII Tubulin using cytosolic cerebellar fractions of Heat and No Heat treated mice. (b) Western blot of c-Fos and βIII Tubulin using nuclear cerebellar fractions of Heat and No Heat treated mice. (c) The graph displays the MEAN intensity values of protein of interest relative to βIII Tubulin±STDEV. There was no significant change in the cerebellar HSP70, NFkB or c-Fos protein levels after thermal cycling.

To test if thermal cycling procedures causes brain injury, changes in the level of damage-associated proteins HSP70, NFkB and c-Fos in 3 week old (wildtype FVB) mice were determined. These animals were anesthetized with isoflurane and their cerebella heated (Heat) or not heated (No Heat). 24 hr post heating, the animals were euthanized and their cerebellar tissue processed for Western blot analysis. It was found that heating the cerebellum with the laser system had no effect on the levels of HSP70, NFkB and c-Fos (FIG. 5), which are protein markers for cellular stress, apoptosis and brain damage respectively.

Example 3

Figure 6:
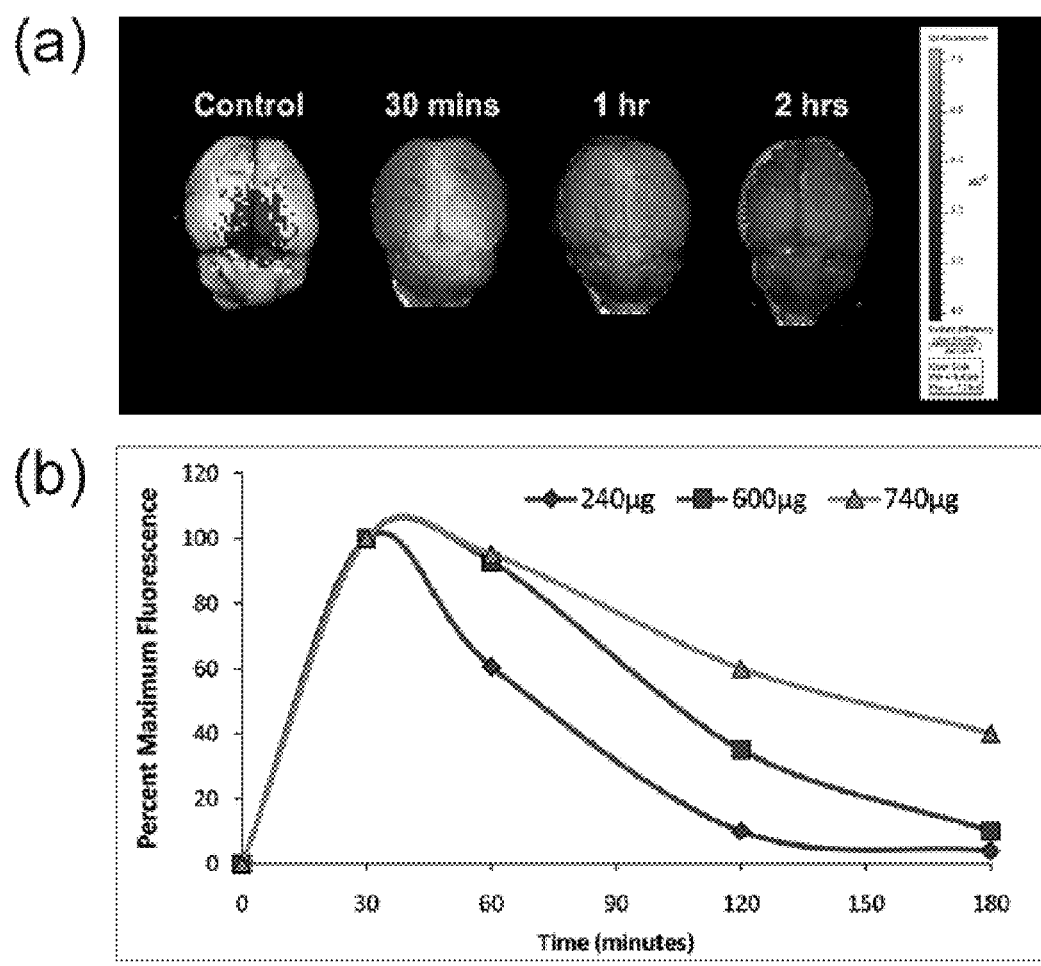
FIG. 6A shows Radiant Efficiency of Synb1-ELP-GGC uptake in the brain over time after IN dose, where green is a high level of uptake, red is a mid level and blue is a low level of uptake.
FIG. 6B shows the total brain distribution of Synb1-ELP-GGC fluorescence after IN dose of 240, 600, and 740 µg over time, (n=3 mice per time point).

An intranasal (IN) route of administering compositions of the presently-disclosed subject matter was studied. With reference to FIG. 6A, FVB two week old mice were anesthetized with ketamine and given 600 g of fluorescent labeled Synb1-ELP-GGC by IN route, the control peptide commonly used to monitor ELP localization and delivery in vivo. Displayed is the Radiant Efficiency of Synb1-ELP-GGC uptake in the brain over time after IN dose, where green is a high level of uptake, red is a mid level and blue is a low level of uptake. With reference to FIG. 6B, the total Brain distribution of Synb1-ELP-GGC fluorescence after IN dose of 240, 600, and 740 μg over time is shown, (n=3 mice per time point).

Example 4

Figure 7:
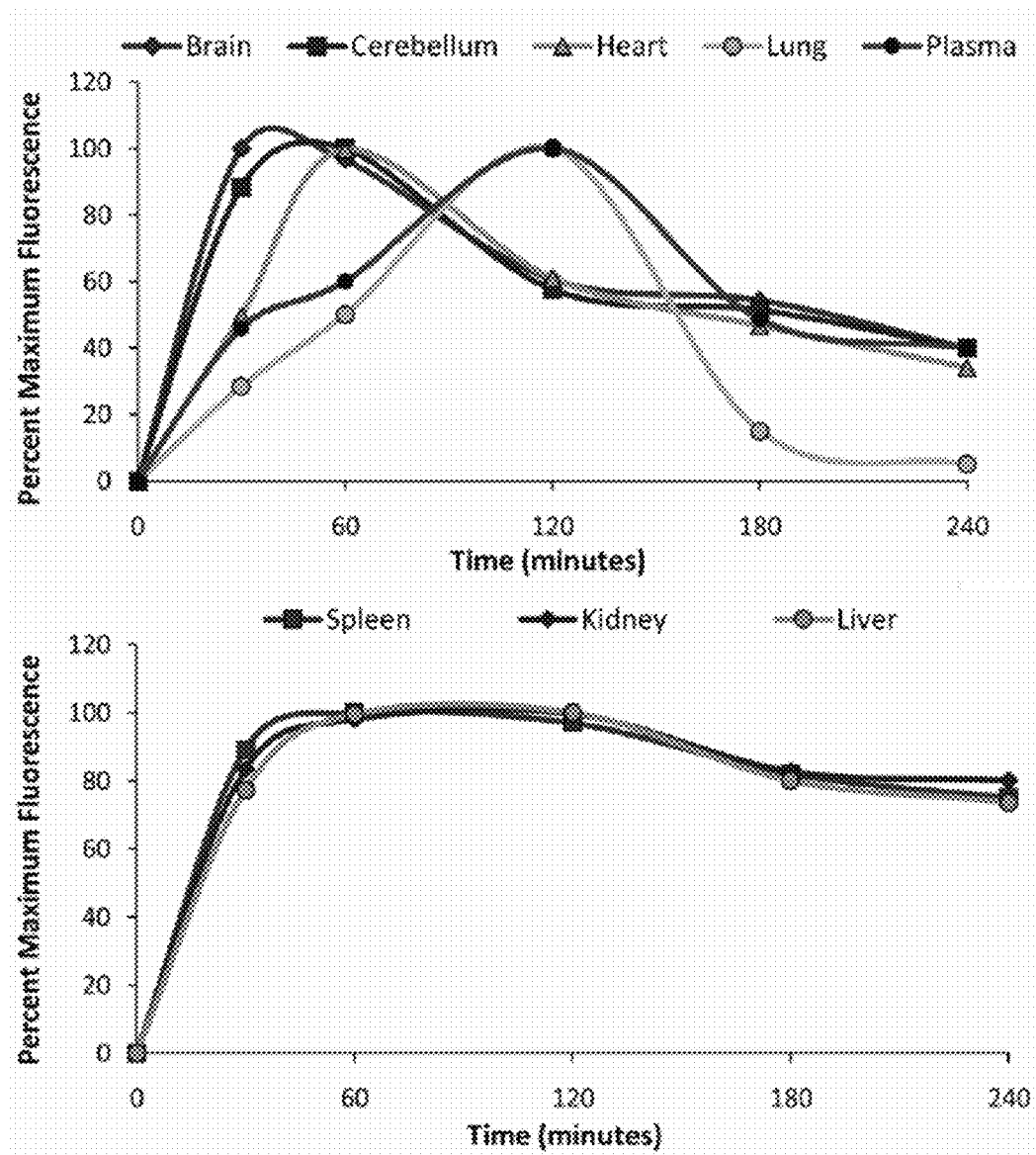
FIG. 7 shows Synb1-ELP kinetics in Brain, Cerebellum, Heart, Lungs and Plasma (top panel), and Synb1-ELP kinetics of the Spleen, Liver and Kidney (bottom panel).

Plasma kinetics of compositions of the presently-disclosed subject matter was studied. With reference to FIG. 7, 3 week old FVB mice were anesthetized with ketamine and given 600 μg of fluorescent labeled Synb1-ELP by intranasal route (IN), the control peptide commonly used to monitor ELP localization and delivery in vivo. At various time points organs and blood plasma were taken and measured. Shown in the Top graph is the Synb1-ELP kinetics in Brain, Cerebellum, Heart, Lungs and Plasma. Shown is the Bottom graph is the Synb1-ELP kinetics of the Spleen, Liver and Kidney.

Example 5

The mutant ataxin-1 is phosphorylated by protein kinase A (PKA) and stabilized by binding of the 14-3-3 protein to resist degradation. This leads to a toxic accumulation of ataxin-1 in the nuclei of SCA1 PCs. The over-expressed mutant ataxin-1 makes nuclear inclusions both in cell culture and a mouse model. Therefore, to decrease ataxin-1 toxicity another approach would be to target SCA1 PCs with therapeutic peptides (TPs) that will directly influence ataxin-1 phosphorylation, stabilization and aggregation.

To the CPP-ELP different therapeutic polypeptides are conjugated. To target PKA, a PKA inhibitory peptide which binds to the active site and a substrate peptide that competes with ataxin-1 are designed. Further, peptides which will interact with 14-3-3 and modulate its binding to mutant ataxin-1 are designed.

Administration can be achieved intranasally, intravenously or intraperitoneally, and the ability of these compositions to pass the BBB, accumulate in Purkinje cells, and improve motor coordination and cerebellar pathology in a SCA1 mouse model can be assessed.

Therapeutic polypeptides include: 14-3-3 nonphosphorylated inhibitory peptide R18 (FHCVPRDLSWLDLEANM-CLP (SEQ ID NO: 29)) with a 6-amino acid spacer sequence WPGSGG fused to R18 (SEQ ID NO: 41) and ELP (e.g., Synb1-ELP-WPGSGG-R18), which interacts with 14-3-3 and probably modulates 14-3-3 binding to mutant ataxin-1; PKA Inhibitor (6-22) polypeptide (TYADFIASGRTGR-RNAI (SEQ ID NO: 30)-NH$_2$) with a 6-amino acid spacer sequence WPGSGG fused to PKI (SEQ ID NO: 41) and ELP (e.g., Synb1-ELP-WPGSGG (SEQ ID NO: 41)-PKI), which is a potent and competitive inhibitor of protein kinase A (PKA), having an amino acid sequence corresponding to residues 6-22 of human cAMP-dependent protein kinase inhibitor alpha and is amidated at the C-terminus; and normal ataxin-1 polypeptide, which will block mutant ataxin-1 mediated loss of D2R protein expression in a cell culture model.

Figure 8:
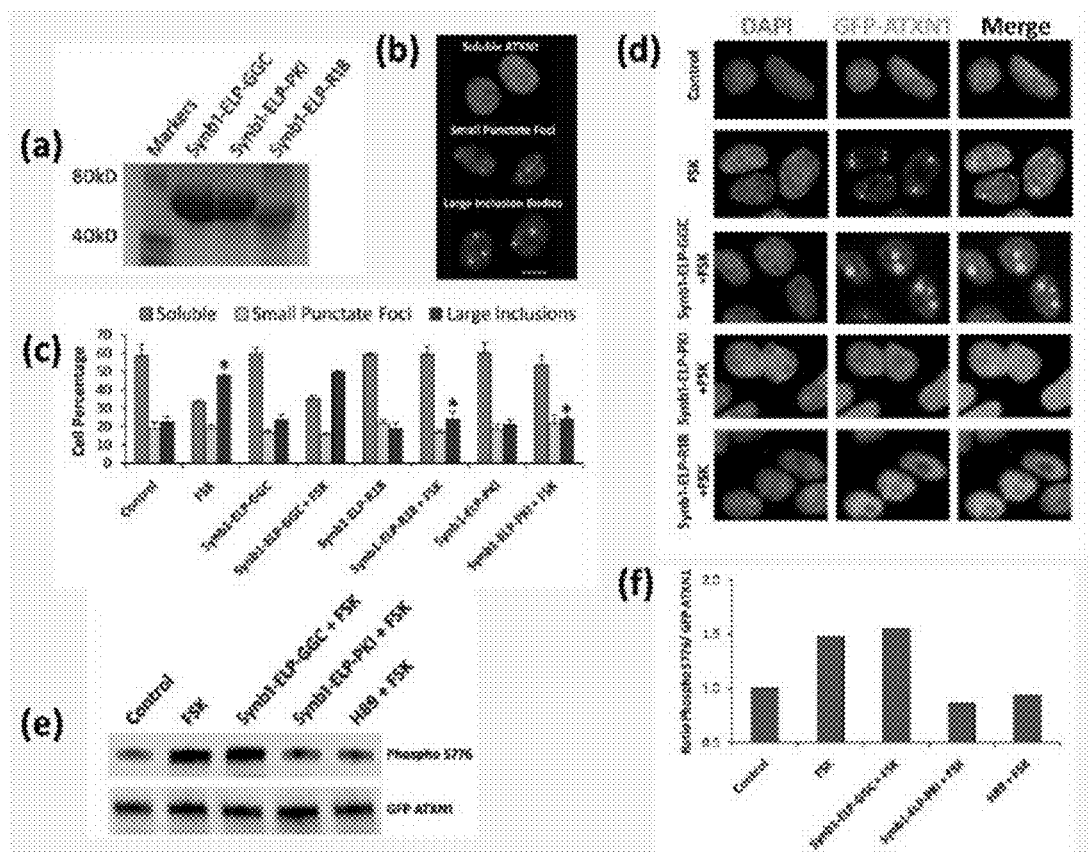
FIG. 8 includes the following: (a) Synb1-ELP PKI and R18 peptides where expressed in XL1 Blue *E. coli*. Shown are the purified ELP peptides: Synb1-ELP-GGC (control peptide), Synb1-ELP-WPGSGG (SEQ ID NO: 41)-PKI and Synb1-ELP-WPGSGG (SEQ ID NO: 41)-R18. ELP peptides have MW around 60 kD. (b) HEK cells expressing GFP-ATXN1 [82Q] display three phenotypes, soluble nuclear staining, small punctate foci, and large nuclear inclusions, scale bar 10 µm. Stable GFP-ATXN1[82Q] HEK cells were placed on slides and pretreated with 50 µM SynB1-ELP-GGC, Synb1-ELP-WPGSGG (SEQ ID NO: 41)-R18 or Synb1-ELP-WPGSGG (SEQ ID NO: 41)-PKI for 2 hrs. The slides were treated with 60 µM Forskolin (FSK) for 4 hrs and then fixed with 4% PFA. FSK is known to increase cAMP production and increase PKA activity. (c) Shows the effect on different ELP peptides on FSK stimulated inclusion formation. The data is MEAN±SE of the % cells expressing the various three phenotypes. Statistics were performed using the student's t-test. *FSK vs Synb1-ELP-WPGSGG (SEQ ID NO: 41)-R18+FSK or Synb1-ELP-WPGSGG (SEQ ID NO: 41)-PKI+ FSK, *P<0.05. (d) Epi-fluorescence of HEK cells expressing GFP-ATXN1[82Q] under the reported treatment conditions, where DAPI nuclear stain is shown in blue and GFP-ATXN1 [82Q] in green. (e) GFP-ATXN1[82Q] cells were placed on 12-well plates and pretreated with 50 μM Synb1-ELP-GGC, Synb1-ELP-WPGSGG (SEQ ID NO: 41)-PKI or 10 μM H89, a known PKA inhibitor for 2 hrs. Next, the cells were treated with 60 μM FSK for 4 hrs and then lysed for Western blotting. 10 μgs of protein was loaded into each well and ran on 4-20% acrylamide gel and transferred to PVDF membrane. The Western blot was analyzed with GFP and Phospho S776 ATXN1 antibodies. Data shows the effect of Synb1-ELP-WPGSGG (SEQ ID NO: 41)-PKI on ATXN1 S776 phosphorylation. (f) Protein band density was taken using Image J software. The graph shows the Ratio of Phospho S776 ATXN1 to GFP ATXN1.

To produce PKI and R18 ELP peptides, DNA corresponding to PKI and R18 were cloned into Synb1-ELP vectors, then check by DNA sequencing. The proteins were expressed in XL1 Blue E. coli cells (FIG. 8A). To determine if the PKA and 14-3-3 inhibitory peptides can block mutant ataxin-1 aggregation in vitro, the effects of Synb1-ELP-WPGSGG (SEQ ID NO: 41)-R18 and Synb1-ELP-WPGSGG (SEQ ID NO: 41)-PKI peptides on mutant ataxin-1 inclusion formation were observed. Data in FIGS. 8D and 8C demonstrates that both Synb1-ELP-WPGSGG (SEQ ID NO: 41)-R18 and Synb1-ELP-WPGSGG (SEQ ID NO: 41)-PKI peptides significantly reduce mutant ataxin-1 aggregation/inclusion formation by inhibiting the PKA-14-3-3-ataxin-1 pathway in HEK cells expressing GFP-ATXN1[82Q]. In addition, Western blot data revealed that Synb1-ELP-WPGSGG(SEQ ID NO: 41)-PKI treatment reduced ATXN1 S776 phosphorylation in HEK GFP-ATXN1[82Q] cells; H89, a known PKA inhibitor was used as the positive control (FIGS. 7e and f). Taken together, these data support efficacy of thermally targeting CCP-ELPs to the cerebellum in an animal. These data further support the efficacy of blocking of PKA-14-3-3-ataxin-1 pathway in vitro by Synb1-ELP-WPGSGG (SEQ ID NO: 41)-R18 and Synb1-ELP-WPGSGG (SEQ ID NO: 41)-PKI.

Example 6

Figure 9:
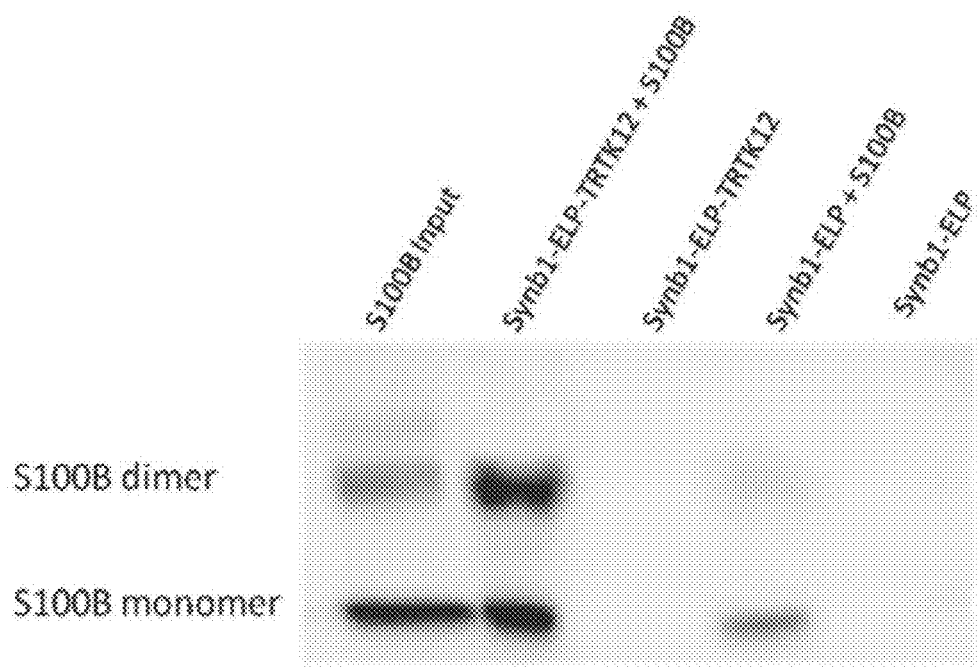
FIG. 9 is a blot showing that CPP-ELP-TRTK12 interacts with S100B protein in vitro. Solutions containing 60 μM Synb1-ELP-TRTK12 or Synb1-ELP were mixed with or without 1 μM S100B in PBS for 30 min at 37° C. The solutions were then incubated in a hot water bath maintained at 50° C. for 5 minutes to induce SynB1-ELP-TRTK12 aggregation. After heating, the solutions were centrifugated at 14,000 rpm to recover the ELP polypeptide aggregates (pellets). The ELP polypeptide pellets were washed 3 times with PBS and reheated and pelleted between washes. To assess ELP polypeptide-S100B interactions, the remaining ELP pellets were subjected to western blotting using a S100B antibody. The Synb1-ELP-TRTK12 polypeptide showed strong interaction with S100B dimer and monomer as compared to the control Synb1-ELP polypeptide.

Targeted Delivery of S100B Inhibitory Peptide to SCA1 Mouse Cerebellum. SCA1 PCs were targeted with a TP (TRTK-12) that can directly interact with the BG S100B protein. A composition of the presently-disclosed subject matter was prepared, including TRTK-12 at the C-terminus of a CPP-ELP. With reference to FIG. 9, it is shown that SynB1-ELP-TRTK12 interacts strongly with S100B protein in vitro.

Example 7

A minimum of five 2 wks old SCA1/+mice were treated IP with vehicle (saline), ELP-GGC or ELP-TRTK peptides multiple times (total 10 doses) every other day for 3 wks. Some animals were subjected to hyperthermia. After completion of the treatments, animals were subjected to behavioral tests.

Bar cross test. The bar-crossing apparatus for testing balance and fine motor coordination consisted of a horizontal U-shaped platform made of wood supported on 30 cm legs. The two parallel 30-cm-long bars of the U were wide enough (18 mm) for the mice to walk easily, whereas the piece connecting them, the challenge bar, was also 30 cm long but only 2 mm wide. Animals were placed on one of the wide bars and allowed to move about on the apparatus for 5 min. After the spontaneous activity portion of the bar cross test, animal were subjected to a forced task. In this task, the mice were placed in the middle of the challenge bar in order to force a crossing attempt. A maximum of 120 sec was allowed for mice to stay on the bar, and the latency to fall (on a padded surface; height=30 cm) or cross (Cross) successfully was measured in seconds. The surface of the apparatus was cleaned with mild soap solution and air-dried between mice. Animal performances on the bar cross apparatus were videotaped and later manually scored for the following spontaneous motor behaviors [Vig et al 2011]: Locomotion Time, duration of motor activity; Passivity, duration of inactivity; Slips, frequency of animal having one or more legs unexpectedly slip off the wide bar; Sniff Up, frequency of pointing nose upward while making movements of nasal passages; Sniff Down, frequency of placing head below the platform while making movements of nasal passages; Tests were performed on mice between 10:00 A.M. and 4:00 P.M., and were conducted only once after 3 weeks of TP or vehicle treatment and 4 days of rotarod test.

Figure 10A:
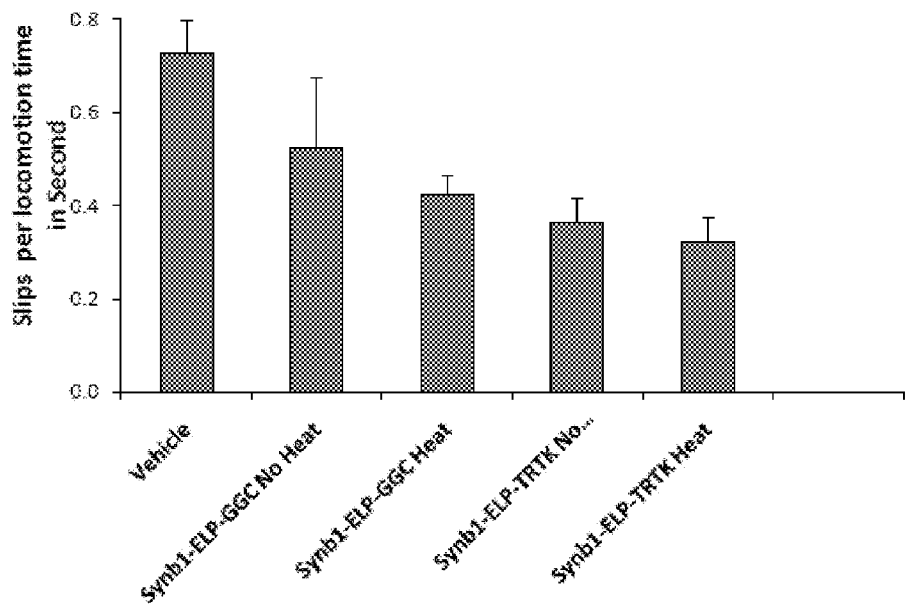
FIG. 10 includes the results of a bar cross test, showing slip frequency (FIG. 10A) and sniff up and sniff down frequency (FIG. 10 B) in control animals and animals receiving compositions of the presently-disclosed subject matter, with and without heat.
Figure 10B:
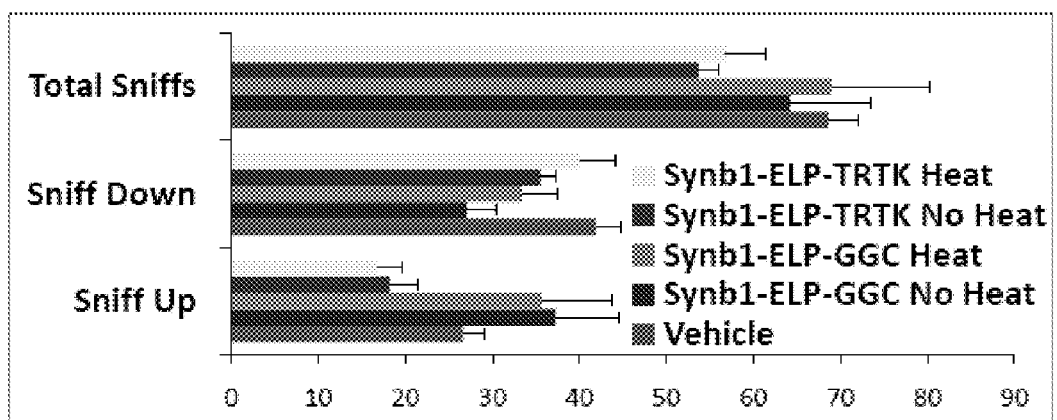

The bar cross test assessed the fine motor coordination and balance capabilities of vehicle or TP treated mice. SCA1/+ animals usually show hyperactivity and slip frequently with higher Sniff Up and down frequency as compared to age matched wildtype animals as reported earlier (Vig et al 2011). The CPP-ELP-TRTK treatments suppresses these activities as shown in FIG. 10.

Example 8

IgG levels in plasma of mice treated withof SynB1-ELP-GGC (100 mg/kg) and SynB1-ELP-TRTK (100 mg/kg) were obtained. Mice were treated multiple times without induction of hyperthermia. IgG levels were measured using ELISA. Samples were diluted 1:50,000 and compared against a standard curve generated using a mouse IgG standard. The following data show that multiple ELP treatments do not induce a significant immune response in the mice.

|  | OD Value | St Dev |
| --- | --- | --- |
| ELP-TRTK (no heat) | 0.255167 | 0.052972 |
| ELP-GGC (no heat) | 0.277333 | 0.037048 |
| Saline (no heat) | 0.235833 | 0.083247 |

Example 9

S100B, a glial secreted protein is believed to play a major role in neurodegeneration in Alzheimer's disease, Down syndrome, traumatic brain injury and spinocerebellar ataxia type 1 (SCA1). SCA1 is a trinucleotide repeat disorder in which the expanded polyglutamine mutation in the protein ataxin-1 primarily targets Purkinje cells (PCs) of the cerebellum. Currently, the exact mechanism of S100B mediated PC damage in SCA1 is not clear. However, herein it is shown that S100B may act via the activation of the RAGE signaling pathway resulting in oxidative stress mediated injury to mutant ataxin-1 expressing neurons. To combat S100B mediated neurodegeneration, a selective thermally responsive S100B inhibitory peptide, Synb1-ELP-TRTK was designed. The therapeutic polypeptide was developed using three key elements: (1) the elastin-like polypeptide (ELP), a thermally responsive polypeptide, (2) the TRTK12 peptide, a known S100B inhibitory peptide (3) a cell penetrating peptide, Synb1, to enhance the intracellular delivery. Binding studies revealed that the peptide, Synb1-ELP-TRTK, interacts with its molecular target, S100B and maintains a high S100B binding affinity as comparable with the TRTK12 peptide alone. In addition, in vitro studies revealed that Synb1-ELP-TRTK treatment reduces S100B uptake in SHSY5Y cells. Furthermore, the Synb1-ELP-TRTK peptide decreased S100B induced oxidative damage to mutant ataxin-1 expressing neurons. To test the delivery capabilities of ELP based therapeutic peptides to the cerebellum; mice were treated with fluorescently labeled Synb1-ELP and observed that thermal targeting enhanced peptide delivery to the cerebellum. The framework for thermal based therapeutic targeting to regions of the brain, particularly the cerebellum, is described here. Overall, the data suggest that thermal targeting of ELP based therapeutic peptides to the cerebellum is a novel treatment strategy for cerebellar neurodegenerative disorders.

Introduction

Spinocerebellar ataxia type 1 (SCA1) belongs to a group of CAG repeat neurodegenerative diseases. In SCA1, the expanded poly-glutamine containing protein ataxin-1 causes progressive ataxia resulting from the loss of cerebellar Purkinje cells (PCs) and neurons in the brainstem (Koeppen, 2005, Orr and Zoghbi, 2007, Matilla-Duenas et al., 2008). Overexpression of the human mutant ataxin-1 gene in PCs of SCA1 transgenic (Tg) mice results in a phenotype very similar to SCA1 patients (Burright et al., 1995). In SCA1 Tg mice, the earliest morphologic change is the appearance of cytoplasmic PC vacuoles containing the Bergmann glial (BG) protein S100B (Skinner et al., 2001, Vig et al., 2006, Vig et al., 2009). Recently, it was reported that these PC vacuoles develop both in SCA1 Tg mice and SCA1 patients, where the vacuolar formation is associated with abnormal PC morphology (Skinner et al., 2001, Vig et al., 2006, Vig et al., 2009). The S100B protein belongs to the EF-hand family of calcium binding proteins and acts as a neurotrophic or neurotoxic signaling molecule for neighboring neurons (Winningham-Major et al., 1989, Donato, 1991, Reeves et al., 1994, Barger et al., 1995, Whitaker-Azmitia et al., 1997, Donato, 1999, Huttunen et al., 2000, Donato, 2001, Rothermundt et al., 2003, Zimmer et al., 2005, Donato et al., 2009, Sorci et al., 2010). Many studies suggest that increased levels of S100B in the disease prone regions are a major causative factor for neurodegeneration in a variety of neurological disorders (Griffin et al., 1989, Kato et al., 1990, Rothermundt et al., 2003, Vig et al., 2011). S100B interacts with multiple protein targets including p53, nuclear Dbf2-related kinases, receptor for advanced glycation end products (RAGE), protein kinase C, neuromodulin, and myo-inositol-monophosphatase-1 (Donato, 1999, McClintock and Shaw, 2000, Wilder et al., 2006, Vig et al., 2009). S100B is also a known RAGE ligand, and stimulation of S100B-RAGE signaling increases the production of reactive oxygen species (ROS), causing oxidative damage to neurons (Adami et al., 2004, Donato et al., 2009, Sorci et al., 2010). Currently, it is not clear how S100B mediates the SCA1 pathology; however, herein a neuro-damaging role for S100B is defined, along an oxidative damage pathway in the SCA1 disease. To combat the neuro-damaging effects of S100B in the SCA1 pathology, a therapeutic polypeptide wasusing three key elements: (1) the elastin-like polypeptide (ELP), a thermally responsive polypeptide, (2) the TRTK12 peptide, a known S100B inhibitory peptide, (3) a cell penetrating peptide, Synb1, to enhance intracellular deliver. ELP is a thermally responsive polypeptide derived from mammalian elastin and is composed of multiple Val-Pro-Gly-X-Gly pentapeptide repeats, where X is any amino acid except proline (Li et al., 2001, Bidwell and Raucher, 2005, Bidwell et al., 2007, Dreher et al., 2007, Bidwell and Raucher, 2009, Raucher et al., 2009). ELP based polypeptides are designed to be soluble at temperatures below 38° C., and to aggregate and concentrate at a transition temperature between 39-42° C. (Li et al., 2001, Bidwell and Raucher, 2005, Bidwell et al., 2007, Dreher et al., 2007, Bidwell and Raucher, 2009, Raucher et al., 2009). The ELP based delivery mechanism works by active thermal targeting using externally focused hyperthermia directed at tissues with a large vasculature structure, such as cancerous tumors (Dreher et al., 2007). The Synb1 peptide is derived from naturally occurring protegrin peptides and mediates the delivery of peptides or compounds across the blood brain barrier (Rousselle et al., 2000, Sarantseva et al., 2009). On the C-terminus, the therapeutic peptide is fused to the S100B inhibitory peptide, TRTK12. The peptide TRTK12 has been shown to have a high binding affinity for S100B with the capability to block S100B interaction with S100B target proteins (Ivanenkov et al., 1995, Bianchi et al., 1996, McClintock and Shaw, 2000, Frizzo et al., 2004, Charpentier et al., 2010). Previously, it was shown that the TRTK12 peptide is therapeutic to SCA1 mice, where animals given TRTK12 displayed a significant improvement in ataxic behavior (Vig et al., 2011). Herein it is demonstrated that the ELP based technology can thermally target therapeutics to areas of the brain (e.g., cerebellum) to combat multiple CNS disorders, especially the cerebellar ataxias.

Materials and Methods
Materials

Fugene 6 transfection reagent and green fluorescent protein (GFP) antibody were purchased from Roche (Indianapolis, Ind., USA). S100B antibody was purchased from Abcam (Cambridge, Mass., USA). S100B protein was purchased from Sigma-Aldrich. RAGE and Synaptophycin antibodies were purchased from Santa Cruz Biotechnology (Santa Cruz, Calif., USA). TRTK12 peptide was purchased from AnaSpec (San Jose, Calif., USA). Fetal bovine serum (FBS) was purchased from HyClone (Logan, Utah, USA).

Polypeptide Production

ELP was modified by addition of the Synb1 peptide (RGGRLSYSRRRFSTSTGR(SEQ ID NO: 11)) and TRTK12 peptide (TRTKIDWNKILS (SEQ ID NO: 31)) or GGC peptide to produce Synb1-ELP-TRTK or Synb1-ELP-GGC by molecular cloning in a pET25b+ expression vector by recursive directional ligation and selected by ampicillin resistance as previously described (Meyer and Chilkoti, 1999). Constructs were verified by DNA sequencing. CPP-ELP-GGC polypeptides are commonly used as CPP-ELP control peptides (Massodi et al., 2009, Moktan et al., 2010), where GGC stands for the last three amino acids (glycine, glycine and cysteine) of the CPP-ELP; also CPP-ELP-GGC polypeptides are commonly labeled on the C terminal cysteine residue with a fluorescent dye to monitor the impact of the CPP on fluorescent ELP localization in cell culture (Massodi et al., 2009, Moktan et al., 2010). ELP constructs were expressed using the pET25 expression system and purified by inverse transition cycling as described previously (Meyer and Chilkoti, 1999, Bidwell and Raucher, 2005). A turbidity assay was used to determine the transition temperature (Tt), where concentrations of Synb1-ELP-TRTK and Synb1-ELP-GGC from 5 µM to 40 µM were placed in DMEM media containing 10% fetal bovine serum as described previously (Bidwell and Raucher, 2005, Bidwell et al., 2010). The polypeptide solutions were heated at a rate of 1° C./min in a multi-cell holder in a UV-VIS spectrophotometer (Cary 100, Varian instrument). Turbidity was monitored by measuring the absorbance change at 350 nm every minute. This absorbance data was converted to a percentage of maximum absorbance as described previously (Bidwell and Raucher, 2005). The Tt was defined as 50% of the maximum of polypeptide aggregation.

Thermal Pull-Down Assay

Solutions containing 60 µM Synb1-ELP-TRTK or Synb1-ELP-GGC were mixed with or without 1 µM S100B in PBS for 30 minutes at 37° C. The ELP peptides were then purified using thermal cycling and washing with PBS. Thermal cycling consists of heating an ELP solution to 42° C. followed by centrifugation at 13 k rpm for 2 minutes. The resulting ELP pellet was then resuspended in cold PBS. The thermal cycling procedure was repeated for a total of five times to remove unbound S100B. To assess any ELP peptide S100B interactions, the purified ELP pellets were subjected to western blotting using an S100B antibody.

Binding Studies

The tryptophan fluorescence of 5.0 µM Synb1-ELP-TRTK, 5.0 µM Synb1-ELP-GGC and 5.0 µM TRTK12 were measured using an Aminco Bowman Series 2 fluorescent spectrophotometer with and Excitation wavelength of 295 nm and an Emission wavelength of 350 nm in 25 mM TrisHCL and 0.1 mM $CaCl_2$ at 12° C. (to avoid aggregation of ELP) or in a solution of containing 25 mM TrisHCL, 0.1 mM $CaCl_2$ and 1 mM EGTA at 12° C. S100B was titrated from 100 nM up to 3.0 µM into the various peptide solutions and changes in tryptophan fluorescence were recorded into an Excel file and graphs produced. A Fluorescence % was plotted against free S100B concentration using GraphPad Prism software. A Fluorescence % was calculated as follows: [(Maximum fluorescence−Observed fluorescence)/(Maximum fluorescence−Minimum Fluorescence)]×100%. Where the maximum fluorescence is the fluorescence of 5.0 µM Synb1-ELP-TRTK or 5.0 µM TRTK12 before titration of S100B and the minimum fluorescence is the fluorescence of 5.0 µM Synb1-ELP-TRTK or 5.0 µM TRTK12 fully saturated with bound S100B. GraphPad Prism software was used to calculate Kd and $R^2$ values for the binding studies.

Cell Culture Studies

SHSY5Y cells (Invitrogen, Carlsbad, Calif., USA) were maintained in DMEM/F12 media (Fisher, Houston, Tex., USA) supplemented with 15% FBS, penicillin-streptomycin (Sigma), and grown in an incubator at 37° C. in the presence of 5% $CO_2$. S100B was labeled with Alexa 488 labeling kit (Invitrogen) to produce 488-S100B. WT SHSY5Y cells were placed on 2-well slides or 12-well plates (Fisher) at concentration of 100,000 cells per well and treated with 50 µM Synb1-ELP-TRTK or Synb1-ELP-GGC for 1 hr at 37° C. Next, cells were washed then treated with 1 µM 488-S100B for 3 hrs and S100B uptake was analyzed by Epi-fluorescence or by Beckman Cytometric FC 500 flow cytometer as previously described (Bidwell et al., 2009). For flow cytometry experiments, 488-S100B uptake was measured by quenching extracellular fluorescence by coating the cells with Trypan Blue (Fisher) as described previously (Bidwell et al., 2009). Experiments were repeated at least three times and statistics taken. SHSY5Y stable cell lines were produced by transfecting with either GFP-ATXN1[82Q] or GFP-ATXN1[30Q] vectors (described previously (Hearst et al., 2010)) using Fugene 6 transfection reagent and selected by G418 (G418 sulfate 600 µg/ml, Sigma) resistance as previously described (Hearst et al., 2010). Cells were grown in 15% FBS in F-12/DMEM media plated on 2 well Lab-Tek CC2 chamber slides (Fisher). Cells were subjected to treatment with 25 nM TPA (Sigma) for 3 days to produce differentiated SHSY5Y cell lines as described previously (Presgraves et al., 2004, Cheung et al., 2009). Next slides were fixed and probed with the primary GFP, RAGE and Synaptophycin antibodies and fluorescent secondary antibodies Alexa 488 and Alexa 546 (Invitrogen) followed by DAPI (Invitrogen) staining as previously described (Hearst et al., 2010). Cells were observed on an Olympus BX60 epifluorescence microscope. Changes in neurite length after S100B treatment were measured using ImageJ software. Statistical significance was calculated using student's t-test where n=100 per group, where P<0.05 is consider significant. Experiments were repeated for a total of three times to gather statistical significance.

Oxyblot Experiments

GFP-ATXN1[82Q] or GFP-ATXN1[30Q] stable cells were placed on 12-well plates at a concentration of 60,000 cells per well. Cells were treated with 25 nM TPA for 3 days to produce differentiated SHSY5Y cell lines. Next, the cells were pretreated with 50 µM Synb1-ELP-TRTK for 1 hr then treated with 5 µM S100B for 2 hrs or treated with 150 µM $H_2O_2$ (Fisher) for 2 hrs, where control cells were treated with serum free media for 3 hrs. Then the cells were lysed in 1% BME (Sigma) and RIPA buffer (50 mM Tris-HCl, pH 7.5, 150 mM NaCl, 1 mM EDTA, 1% sodium deoxycholate and 1% NP-40, Sigma). Cell lysates were analyzed with the Oxyblot kit according to manufacturer's protocol (Roche) and with a β-tubulin antibody (Sigma), where 5 µgs of protein was loaded in each well of 4-20% acrylamide gel (Bio-Rad Laboratories, Hercules, Calif., USA). Optical densities of the protein bands were taken using ImageJ software. Graphs were produced in Excel and show the optical density ratio of oxidized protein/β-tubulin normalized to the control. Experiments were repeated for a total of three times to gather statistical significance, n=3. Statistics were taken using student's t-test, where P<0.05 is consider significant.

In Vivo Studies

Wild-type (WT, FVB) mice were obtained from Jackson Labs, Bar Harbor, Me., USA. All animal protocols were approved by Institutional Animal Care and Use Committee (IACUC) at the University of Mississippi Medical Center. The 3 week old animals were anesthetized with isoflurane (Butler Animal Health Supply, Dublin, Ohio, USA) and a temperature probe was gently inserted into the cerebellum and the frontal lobe to monitor temperature changes under the thermal cycling procedure. The thermal cycling procedure consisted of 30 minutes of heating and 5 minutes of cooling followed by two additional cycles of 20 minutes of heating and 5 minutes of cooling. The cerebellum was heated with the Mettler Laser-Systim 540® Laser System using the 785 nm Single AlGaAs Diode Class 3B laser applicator with an elliptical beam area of 9.2 $mm^2$ (Mettler Electronics, Anaheim, Calif., USA). Synb1-ELP-GGC protein was labeled with Alexa 750 maleimide labeling kit (Invitogen) to produce fluorescent labeled Synb1-ELP-GGC. After anesthesia with isoflurane, 3 week old FVB mice were injected IP with 100 mg/kg fluorescent labeled protein or 200 µL saline as the control. 2 hrs post heating, the animals were euthanized by $CO_2$ inhalation and their brains, heart, spleen, right lung, right kidney and liver removed. The fluorescent distribution of the brain and other organs were visualized with IVIS Live Animal Imager (Caliper Life Sciences, Hopkinton, Mass., USA) using an Excitation wavelength of 745 nm and an Emission wavelength of 800 nm. Radiant Efficiency is a common unit used to measure Epi-fluorescence changes in vivo (Shcherbo et al., 2010). The average Radiant Efficiency of the cerebellum ±SE was calculated by taking an ROI of the cerebellum and using Living Image software (Caliper). The average Radiant Efficiency of the brains, heart, spleen, right lung, right kidney and liver ±SE was calculated by taking an ROI of the organ and using the IVIS software. The experiments were repeated three times with a total of three animals per treatment group, n=3. Statistics were taken using student's t-test, where P<0.05 is considered significant.

Results

The Design of an ELP Based S100B Inhibitory Peptide

Peptide based drugs are gaining popularity as promising new therapeutics due to the ease of peptide design and the high specificity of peptides for their molecular targets (Bidwell and Raucher, 2005, Bidwell et al., 2007, Dreher et al., 2007, Bidwell and Raucher, 2009, Raucher et al., 2009, Bidwell and Raucher, 2010). In this study, an S100B inhibitory polypeptide, Synb1-ELP-TRTK, was designed. The therapeutic peptide was designed to take advantage of the unique properties of each of its three fused peptides, (1) the ELP, a thermally responsive polypeptide, (2) the TRTK12 peptide, a known S100B inhibitory peptide, (3) a cell penetrating peptide, Synb1, to enhance intracellular delivery (FIG. 11A). In previous studies, the delivery of ELP conjugated therapeutic peptides has been successfully demonstrated (Bidwell and Raucher, 2005, Bidwell et al., 2007, Dreher et al., 2007, Bidwell and Raucher, 2009, Raucher et al., 2009, Bidwell and Raucher, 2010). The ELP thermally responsive element allows for simple peptide purification by inverse transition cycling, where ELP conjugated polypeptides aggregate and precipitate at a transition temperature between 39 to 42° C. (FIGS. 11B and 11C) (Li et al., 2001, Bidwell and Raucher, 2005, Bidwell et al., 2007, Dreher et al., 2007, Bidwell and Raucher, 2009, MacKay et al., 2009, Raucher et al., 2009, Bidwell and Raucher, 2010). Taking advantage of the ELP thermal responsive element of the therapeutic peptide, the first thermal pull-down assay to test the interaction between Synb1-ELP-TRTK and the S100B protein was developed (FIG. 11D). It was found that when precipitated by thermal cycling, Synb1-ELP-TRTK bound both S100B monomers and dimers (FIG. 11E). The dimeric S100B protein has been previously shown not to disassociate under standard SDS-PAGE conditions (Donato, 1999). However, the control peptide, Synb1-ELP-GGC, which lacks the TRTK12 peptide, showed little to no interaction with the S100B protein (FIG. 11E). These data suggest that the therapeutic peptide Synb1-ELP-TRTK directly interacts with its molecular target, the S100B protein. Furthermore, the pull-down technique can be used as an alternative to standard pull-down assays using Pro-A or Pro-G beads or further modified by the addition of ELP to accommodate other proteins of interest.

Synb1-ELP-TRTK S100B Binding Affinity

Figure 12:
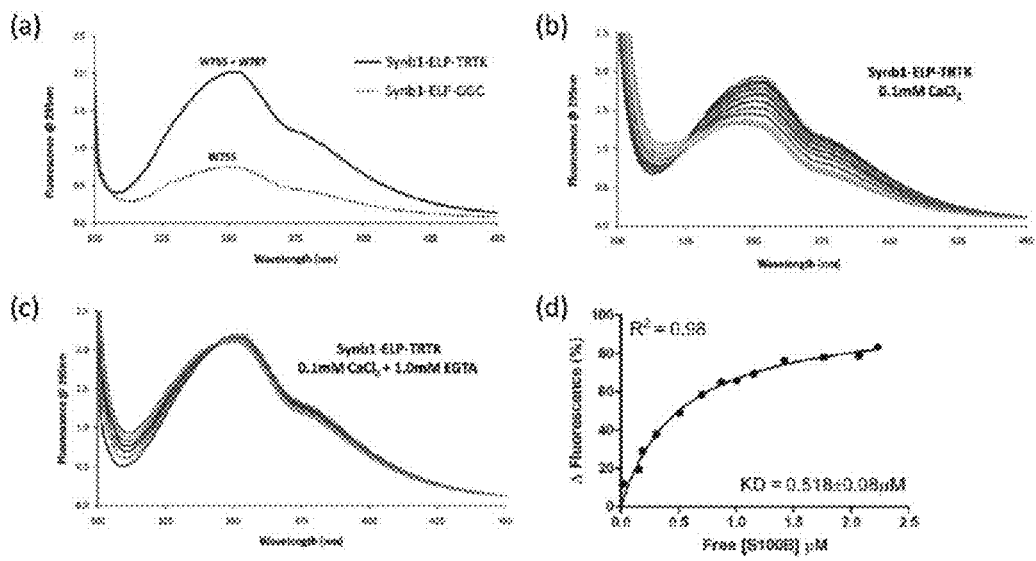
FIG. 12: (a) Shown is the tryptophan fluorescence of 5.0 μM Synb1-ELP-TRTK containing W755 and W767 and the tryptophan fluorescence of 5.0 μM Synb1-ELP-GGC containing only W755. Both peptides displayed maximum fluorescence at 350 nm. (b) Shown is the effect on tryptophan fluorescence of 5.0 μM Synb1-ELP-TRTK observed upon addition of S100B from 100 nM to 3.0 μM in the presence to $CaCl_2$. (c) Shown is the effect on tryptophan fluorescence of 5.0 μM Synb1-ELP-TRTK observed upon addition of S100B from 100 nM to 3.0 μM in the presence to $CaCl_2$ and EGTA. (d) Shown is Δ Fluorescence % of Synb1-ELP-TRTK plotted against free S100B concentration with a Kd of 0.518±0.08 μM and an $R^2$ of 0.98 and a Bmax of 100.
Figure 13:
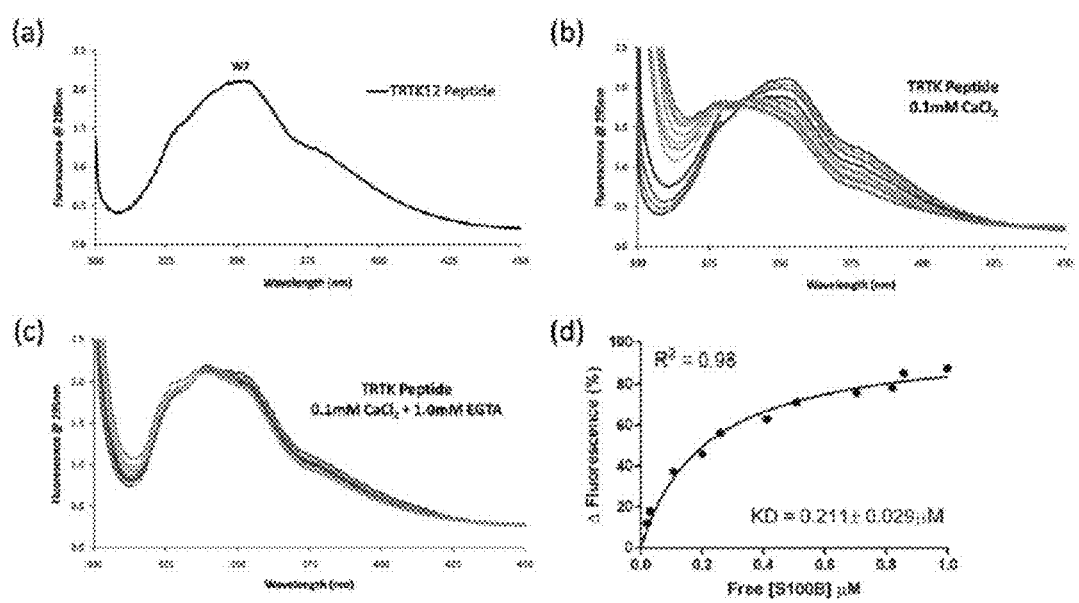
FIG. 13: (a) The graph shows tryptophan fluorescence of 5.0 μM TRTK12 containing W7 with a maximum fluorescence at 350 nm. (b) Shown is the effect on tryptophan fluorescence of 5.0 μM TRTK12 observed upon addition of S100B from 100 nM to 2.5 μM in the presence to $CaCl_2$. (c) Shown is the effect on tryptophan fluorescence of 5.0 μM TRTK12 observed upon addition of S100B from 100 nM to 2.5 μM in the presence to $CaCl_2$ and EGTA. (d) Shown is Δ Fluorescence % of TRTK12 plotted against free S100B concentration with a Kd of 0.211±0.029 μM and an $R^2$ of 0.98 and a Bmax of 100.

Alterations in the binding affinity of a peptide due to its fusion to ELP have never been studied previously. Since the therapeutic peptide Synb1-ELP-TRTK interacted with the S100B protein, using fluorescent spectroscopic techniques, it was further investigated whether the binding affinity of Synb1-ELP-TRTK for S100B differed from that of the native TRTK12. Fluorescent spectroscopy is a sensitive tool used to monitor changes in the local environment of tryptophan residues that occur during a protein-ligand binding event; furthermore, changes in tryptophan fluorescence can be used to calculate binding affinity (Weljie and Vogel, 2000, Bocedi et al., 2004). Previous work has shown that S100B binding reduces tryptophan fluorescence of TRTK12 and like peptides (Ivanenkov et al., 1995). The tryptophan fluorescence of 5.0 µM Synb1-ELP-TRTK and 5.0 µM Synb1-ELP-GGC were measured using a fluorescent spectrophotometer with an Excitation wavelength of 295 nm and an Emission wavelength of 350 nm in 25 mM TrisHCL and 0.1 mM $CaCl_2$ at 12° C. At 295 nm, tryptophan emission spectrum is dominant over the weaker tyrosine and phenylalanine fluorescence (Vivian and Callis, 2001). Synb1-ELP-TRTK contains two tryptophan residues (W755 and W767), while Synb1-ELP-GGC contains only one tryptophan residue (W755). W755 has very little fluorescence at 350 nm which may be due to the 150 neighboring VPGXG repeats of ELP (FIG. 12A). In Synb1-ELP-TRTK, W767, the major binding residue of the S100B binding peptide TRTK12, in combination with W755 shows a large fluorescence emission at 350 nm (FIG. 12A). A decrease in the tryptophan fluorescence intensity of Synb1-ELP-TRTK was observed upon addition of S100B from 100 nM to 3.0 µM (FIG. 12B). This may be due to changes induced by the S100B interaction leading to less exposure of the tryptophan residues to the solvent solution and burial of W767 into the hydrophobic S100B binding site. S100B is a dimeric protein with two TRTK12 binding sites, where the binding is calcium dependent (Zimmer and Weber, 2010). Titration of S100B into a solution containing 25 mM TrisHCL, 0.1 mM $CaCl_2$ and 1 mM EGTA displayed no effect in quenching the tryptophan fluorescence of Synb1-ELP-TRTK at 350 nm (FIG. 12C). Fluorescent quenching can be used to study protein-ligand binding when the formation of the protein-ligand complex leads to a change in fluorescence of the complex (Weljie and Vogel, 2000, Bocedi et al., 2004). Using this fluorescence quenching technique, it is assumed that protein-ligand complex formation is relative to the change in fluorescence. Therefore, Synb1-ELP-TRTK S100B binding was monitored by the percent change in tryptophan fluorescence (Δ Fluorescence %) plotted against free S100B concentration (FIG. 12D) with a Kd of 0.518±0.08 µM and an $R^2$ of 0.98. Next, the same fluorescence techniques were repeated to acquire the binding affinity of the TRTK12 peptide alone to S100B. As expected, the major binding residue W7 of the TRTK12 peptide, displayed strong tryptophan fluorescence intensity at 350 nm (FIG. 13A). Titration of S100B into a solution containing 5.0 µM TRTK12 showed a decrease in the tryptophan fluorescence intensity of TRTK12 upon addition of S100B from 100 nM to 2.5 µM (FIG. 13B). Also, depletion of calcium inhibited this S100B binding process and had little effect on the tryptophan fluorescence intensity of TRTK12 at 350 nm (FIG. 13C). TRTK12-S100B binding was monitored by the A Fluorescence % plotted against free S100B concentration (FIG. 13D) with a Kd of 0.211±0.029 µM and an $R^2$ of 0.98. The results are supported by earlier reports that found that the TRTK12 peptide had an S100B binding affinity between 200-300 nM (Wright et al., 2009). Overall, the binding data indicated that the addition of Synb1-ELP to the TRTK12 peptide, to created Synb1-ELP-TRTK, had a 2 fold impact on S100B binding affinity compared to the TRTK12 peptide alone; where Synb1-ELP-TRTK maintains a high S100B binding affinity.

Synb1-ELP-TRTK Blocks S100B Uptake in SHSY5Y Cells

Figure 14:
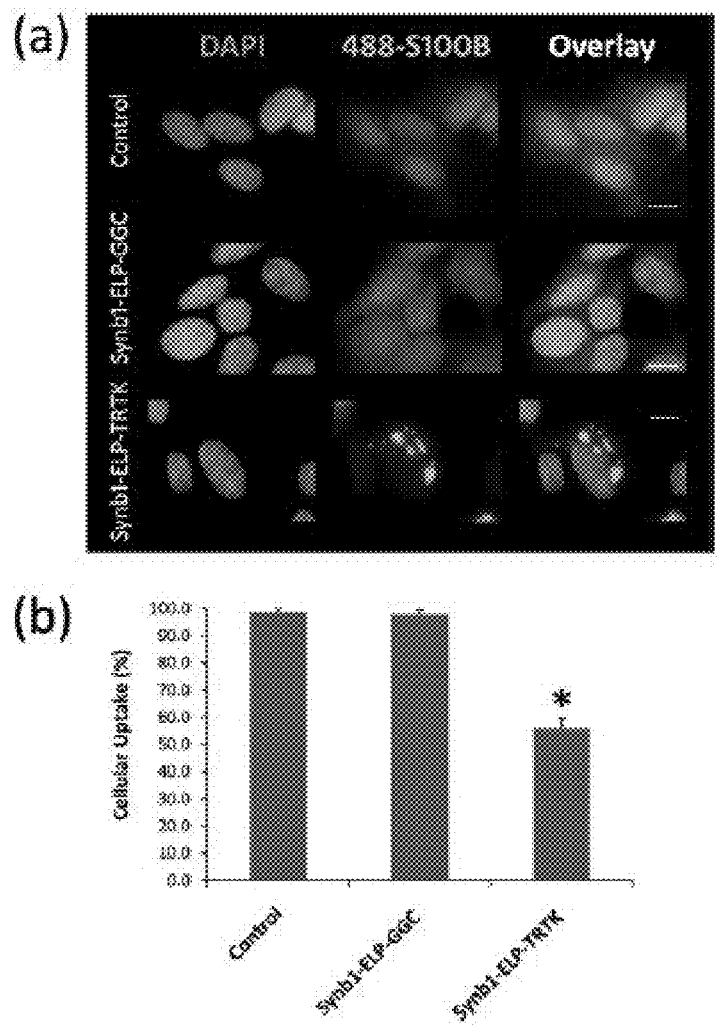
FIG. 14: (a) WT SHSY5Y cells were placed on chamber slides and pretreated with 50 μM Synb1-ELP-TRTK or Synb1-ELP-GGC for 1 hr at 37° C. Next, cells were washed then treated with 1 μM 488-S100B for 3 hrs followed by washing, fixation and DAPI staining. Shown is DAPI nuclear stain in blue and 488-S100B in green. Scale bar: 10 μm. (b) SHSY5Y cells were placed on 6-well plates and pretreated with 50 μM Synb1-ELP-TRTK12 or Synb1-ELP-GGC for 1 hr at 37° C. then treated with 1 μM 488-S100B for 3 hrs, then cells were removed and 488-S100B uptake was measured using flow cytometry. Data is shown as MEAN±STDEV of the % Uptake relative to the control. Statistics were taken using student's t-test. *P<0.05.

S100B is a known RAGE ligand, where S100B uptake is mediated through RAGE receptor binding (Leclerc et al., 2007, Perrone et al., 2008). The neuroblastoma, SHSY5Y cell line is a well known RAGE expressing cell line and has been widely used to study S100B-RAGE signaling (Leclerc et al., 2007). Treatment of SHSY5Y cells with fluorescent labeled S100B, 488-S100B, displayed a localization of S100B in both the cytoplasm and the nucleus (FIG. 14A). It was contemplated that Synb1-ELP-TRTK could block S100B-RAGE signaling and reduce S100B uptake in SHSY5Y cells, which was studied by pretreating SHSY5Y cells with Synb1-ELP-GGC or Synb1-ELP-TRTK for 1 hr followed by 488-S100B treatment. Synb1-ELP-GGC pretreatment had no effect on 488-S100B uptake, however, Synb1-ELP-TRTK pretreatment reduced 488-S100B cellular uptake and localized 488-S100B to large extracellular aggregates (FIG. 14A). These results reconfirmed earlier reports that Synb1-ELP based peptides show both extracellular and intracellular localization in cultured cells (Bidwell et al., 2010). Using flow cytometry techniques under the same experimental conditions, the epi-fluorescence results were further validated. Flow cytometric analysis revealed that Synb1-ELP-TRTK pretreatment significantly reduced 488-S100B uptake in SHSY5Y cells compared to Control and Synb1-ELP-GGC pretreated cells (FIG. 14B). This data suggest that the therapeutic peptide Synb1-ELP-TRTK can be used to block S100B-RAGE signaling.

S100B Causes Damaged to Neurons Expressing Mutant Ataxin-1

S100B acts both as a neurotrophic and a neurotoxic signaling molecule, where its toxicity is based on its concentration in the extracellular environment (Donato, 1991, 1999, 2001, Donato et al., 2009). High levels of S100B through S100B-RAGE signaling causes the production of ROS and downstream oxidative stress (Rothermundt et al., 2003, Donato et al., 2009, Sorci et al., 2010). S100B-RAGE signaling has also been shown to produce ROS in SHSY5Y cells (Leclerc et al., 2007). Studies were designed to determine whether SHSY5Y cells expressing the mutant form of ataxin-1, ATNX1 [82Q], would be more susceptible to oxidative stress through S100B-RAGE signaling compare to SHSY5Y cells expressing normal ataxin-1, ATXN1[30Q]. A recent report found that the super oxide dismutase (SOD) enzyme is sequestered to mutant ataxin-1 inclusion bodies and suggests that polyglutamine-expanded ataxin-1 increases the levels of reactive oxygen species by reducing the functional activity of SOD (Kim et al., 2003b). Loss of SOD function in mutant ataxin-1 expressing cells is further supported by reports demonstrating that ATXN1[82Q] expressing cells are more susceptible to oxidative damaged compared to ATXN1[30Q] expressing cells (Kim et al., 2003a, Kim et al., 2003b, Ryu et al., 2010). Stable expressing GFP-ATXN1[82Q] and GFP-ATXN1 [30Q] SHSY5Y cell lines were produced by G418 selection. Once established, GFP-ATXN1[82Q] and GFP-ATXN1 [30Q] SHSY5Y cell lines were further differentiated into neurons by TPA treatment. TPA has been used to differentiate SHSY5Y cells into neurons, where differentiated SHSY5Y cells grow long neuronal processes or neurites and express the synaptic vesicle protein, synaptophysin (Presgraves et al., 2004, Cheung et al., 2009). After TPA treatment both of GFP-ATXN1[82Q](FIG. 15A) and GFP-ATXN1[30Q](not shown) SHSY5Y cell lines expressed the synaptophysin protein and grew long neuronal processes. Also, both GFP-ATXN1[82Q](FIG. 15B) and GFP-ATXN1[30Q](not shown) SHSY5Y cell lines expressed the RAGE receptor after TPA treatment. Knowing that both differentiated GFP-ATXN1[82Q] and GFP-ATXN1[30Q] SHSY5Y cell expressed RAGE, the impact of S100B was tested on cells with neurites. It was found that after S100B treatment, ATXN1[82Q]-expressing neurons showed a significant reduction in the percentage of cells with neurites compared to untreated ATXN1[82Q] expressing neurons (FIG. 15C). Further, S100B treatment significantly reduced neurite length in ATXN1[82Q] expressing neurons compared to untreated ATXN1[82Q] expressing neurons (FIG. 15D). However, S100B treatment had no significant effect on ATXN1[30Q] expressing cells compared to untreated cells (FIGS. 15C and 15D). The loss of SOD function due to ATXN1[82Q] expression and the ROS production activated by S100B-RAGE signaling, may cause increased oxidative damage in ATXN1 [82Q] expressing neurons activating the neurodegenerative processes. The Oxyblot technique has been used to detect the level of oxidized protein in cultured SHSY5Y cell resulting from ROS production (Jiang et al., 2004, Takano et al., 2007). Using this technique, TPA differentiated GFP-ATXN1[82Q] and GFP-ATXN1[30Q] SHSY5Y cell with S100B were treated and S100B's impact on the level of oxidized proteins compared to the level of β-tubulin protein was analyzed. It was found that differentiated GFP-ATXN1[82Q] cells displayed a greater level of oxidized proteins when treated with S100B compared to GFP-ATXN1[30Q] cells (FIGS. 16A and 16B). Furthermore, Synb1-ELP-TRTK pretreatment significantly blocked S100B's impact on the level of oxidized proteins in ATXN1[82Q] cells (FIG. 16A). $H_2O_2$ induced oxidative damage was used as a positive control to ensure the Oxyblot technique was working properly. It was found that mutant ataxin-1 expressing cells are more sensitive to $H_2O_2$ compared to normal ataxin-1 expressing cells; this confirmed earlier reports that ATXN1[82Q] expressing cells display higher oxidative damage compared to ATXN1[30Q] cells when exposed to $H_2O_2$ (FIG. 16A) (Kim et al., 2003a, Kim et al., 2003b, Ryu et al., 2010). Previously, it has been shown that TRTK12 peptide improves SCA1 PC morphology in cerebellar slice cultures (Vig et al., 2011). The fact that RAGE is highly expressed in PCs of the cerebellum, along with the findings that ATXN1[82Q] expressing neurons are more sensitive to S100B-RAGE signaling, as well as the beneficial effects of TRTK12 on SCA1 PCs in slice culture, defines a role for S100B as a toxic signaling protein in the SCA1 neurodegenerative pathway. Therefore, using therapeutic peptides, such as Synb1-ELP-TRTK to block S100B induced neurotoxic effects is a novel SCA1 treatment strategy.

Thermal Cycling Increases Localization of Fluorescent Labeled Synb1-ELP to the Cerebellum Research has shown that hyperthermic targeting of the ELP biopolymer to tumor vasculature is a very effective methodology to concentrate the macromolecular drug carrier, ELP, to specific biological locations (Meyer et al., 2001, Liu et al., 2006, Dreher et al., 2007). Furthermore, thermal cycling has been shown to be more efficient than continuous heating to increase the accumulation and delivery of ELP to tumors in mice models (Dreher et al., 2007). To test the feasibility of heating the mouse cerebellum without drastically heating other areas of the brain, a temperature probe was inserted into the cerebellum as well as the frontal lobe and monitored temperature changes under a thermal cycling procedure (FIG. 17A). The thermal cycling procedure consisted of 30 minutes of heating and 5 minutes of cooling followed by two additional cycles of 20 minutes of heating and 5 minutes of cooling; where a 785 nm laser pointed at the cerebellum was used as the heating source. During the thermal cycling procedure, the temperature of the cerebellum reached a maximum temperature of 40° C. remaining 2 degrees above the frontal lobe temperature as well as the body temperature (FIG. 17A).

Next, the localization and accumulation of Synb1-ELP-GGC (the control peptide, lacking the TRTK12 modification) was monitored in the brain under heated and unheated conditions. The Synb1-ELP-GGC peptide contains only one cysteine residue found at the end of the C-terminus. Synb1-ELP-GCC was labeled on the C-terminal cysteine residue with Alexa 750 fluorescent dye according to the manufacture's protocol. Three, 3 week old FVB WT mice were anesthetized with isoflurane and given an IP injection of 100 mg/kg fluorescent labeled Synb1-ELP-GGC suspended in a saline solution or saline alone. One hour post injection, the cerebellum of one animal was externally heated (using the thermal cycling procedure above) while the other animals were left unheated. 2 hrs post heating, the animals were euthanized by $CO_2$ inhalation and their brains and organs removed. The brains were then lined up and photographed with the IVIS Animal Imager with an Excitation wavelength of 745 nm and an Emission wavelength of 800 nm (FIG. 17B). Shown is the image displaying a photograph of the brains and the fluorescent uptake of labeled Synb1-ELP-GGC. The Overlay image shows that thermal cycling is an effective targeting method to increase localization of Synb1-ELP-GGC to the cerebellum. The Epifluorescent color scale measures Radiant Efficiency, where blue coloration is low fluorescence, red is mid level fluorescence and green is high fluorescence (FIG. 17B). Next, the IVIS software was used to measure the change in Radiant Efficiency of the cerebellum after thermal targeting of Synb1-ELP-GGC to the cerebellum compared to unheated and saline treated animals. A significant increase in the Radiant Efficiency of the cerebellum was found after a thermal cycling procedure compared to the unheated and the control cerebellums (FIG. 17C). Next, the bio-distribution of Synb1-ELP-GGC was looked at in the brain, heart, spleen (FIG. 17D), lung, kidney and liver (FIG. 17E) from control animals, unheated animals and animals where the cerebellum was heated by thermal cycling. It was found that heating the brain had no significant effect on Synb1-ELP-GGC levels in the various organs analyzed. However, there appears to be an increase in the total brain uptake in animals where the cerebellum was heated compared to unheated animals; however the increase was not significant (FIG. 17D). The increase in brain uptake is most likely due to the enhanced localization of Synb1-ELP-GGC to the cerebellum induced by the focused hyperthermia. Our results are a unique finding, as ELP peptide transport into the brain has never been studied. Overall, it was found that thermal targeting by applying local focused hyperthermia significantly increased Synb1-ELP-GGC localization to the cerebellum. This is the first evidence demonstrating that ELP based therapeutics can be thermally targeted to a particular region of the brain to combat neurodegenerative diseases.

Discussion

Figure 11:
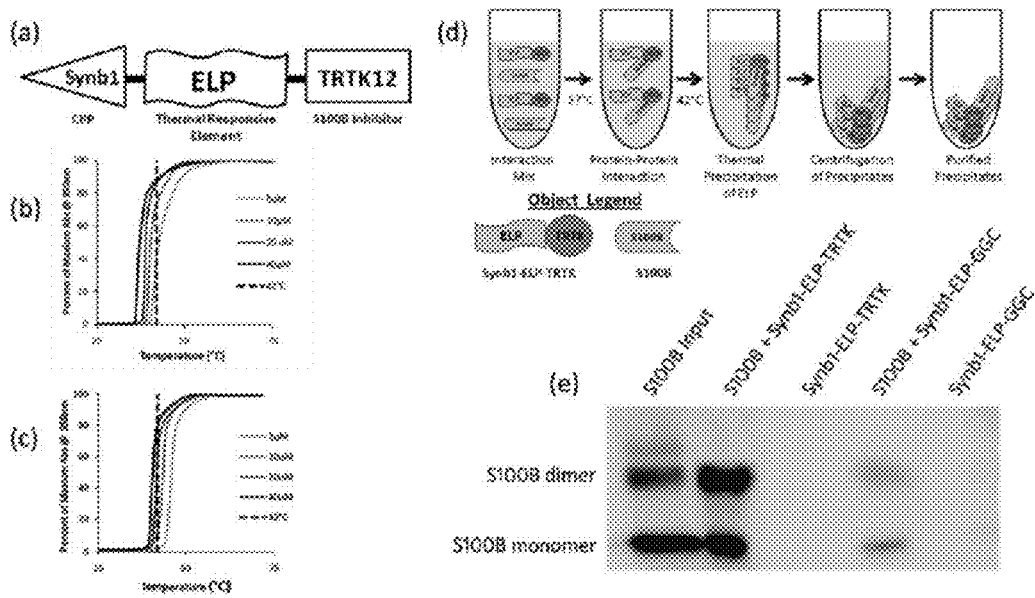
FIG. 11 (*a*) Displayed is a diagram of the therapeutic polypeptide Synb1-ELP-TRTK. Displayed are the three key elements: (1) ELP, a thermally responsive peptide, (2) TRTK12 peptide, a known S100B inhibitory peptide, (3) a cell penetrating peptide, Synb1, to enhance intracellular delivery. Shown are the turbidity assay results of various concentrations of (b) Synb1-ELP-GGC and (c) Synb1-ELP-TRTK heated from 25° C. to 75° C. The peptides Synb1-ELP-GGC and Synb1-ELP-TRTK, shows a transition temperature between 39 to 42° C. (d) Shown is the thermal pull-down assay procedure, where a solution containing S100B and Synb1-ELP-TRTK protein are allowed to interact at 37° C. in a microcentrifuge tube. Next, the solution is heated to 42° C., where the ELP peptide under goes a heat induced conformational change causing the ELP peptides to aggregate and precipitate. Finally, these ELP precipitates are spun at high speed in a centrifuge to from a pellet containing the ELP peptide and its interacting partners, in this case Synb1-ELP-TRTK and S100B. Once the supernatant is removed the protein pellet can be analyzed by western blotting techniques to reveal protein-protein interactions. (e) Shown are the results from the thermal pull-down assay. Solutions containing 60 μM Synb1-ELP-TRTK or Synb1-ELP-GGC (control peptide) were mixed with or without 1 μM S100B and subjected to thermal pull-down assay procedure and analyzed by western blotting using an S100B antibody. Synb1-ELP-TRTK peptide showed a direct interaction with S100B while Synb1-ELP-GGC showed little to no interaction with S100B.
Figure 16:
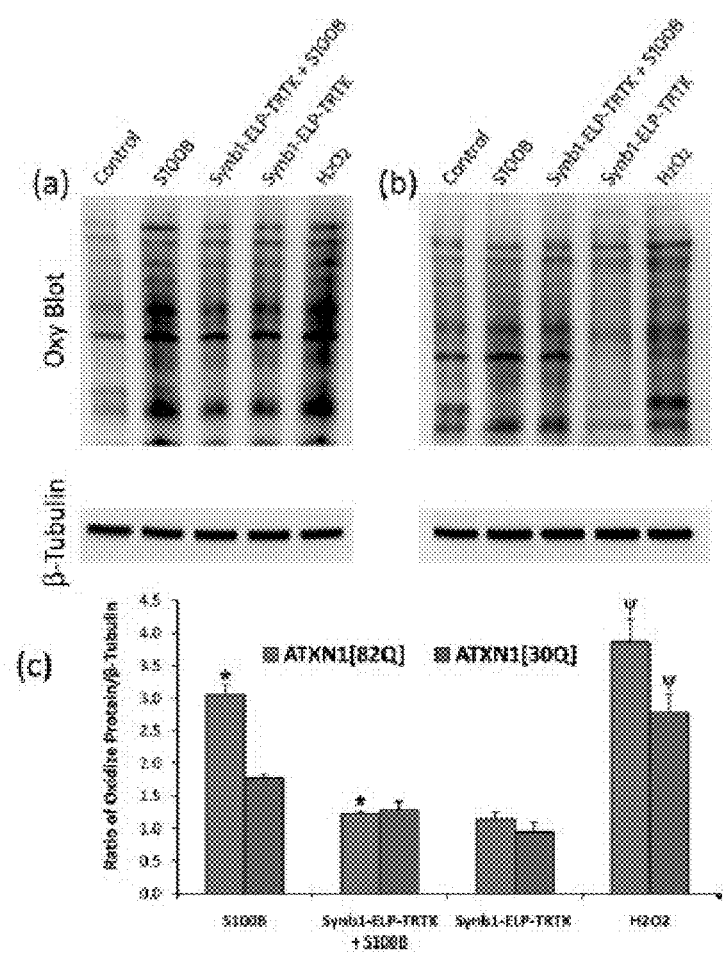
FIG. 16: (a) GFP-ATXN1[82Q] and (b) GFP-ATXN1 [30Q] SHSY5Y stable cells were placed on 12-well plates and subjected to treatment with 25 nM TPA for 3 days to produce differentiated SHSY5Y cell lines. Next, the cells were pretreated with 50 μM Synb1-ELP-TRTK for 1 hr then treated with 5 μM S100B for 2 hrs or treated with 150 μM $H_2O_2$ for 2 hrs, where control cells were treated with serum free media for 3 hrs. Then the cells were lysed and analyzed with the Oxyblot kit and a β-tubulin antibody. Shown is the resulting oxyblot/western blot data. (c) Optical densities of the protein bands were taken using ImageJ software. Graphs shown the ratio of oxidized protein/β-tubulin protein normalized to the control. Statistics were taken using the student's t-test. * GFP-ATXN1[82Q]: S100B vs Synb1-ELP-TRTK+ S100B, P<0.05. ψ GFP-ATXN1[82Q]: $H_2O_2$ vs GFP-ATXN1[30Q]: $H_2O_2$, P<0.05.
Figure 17:
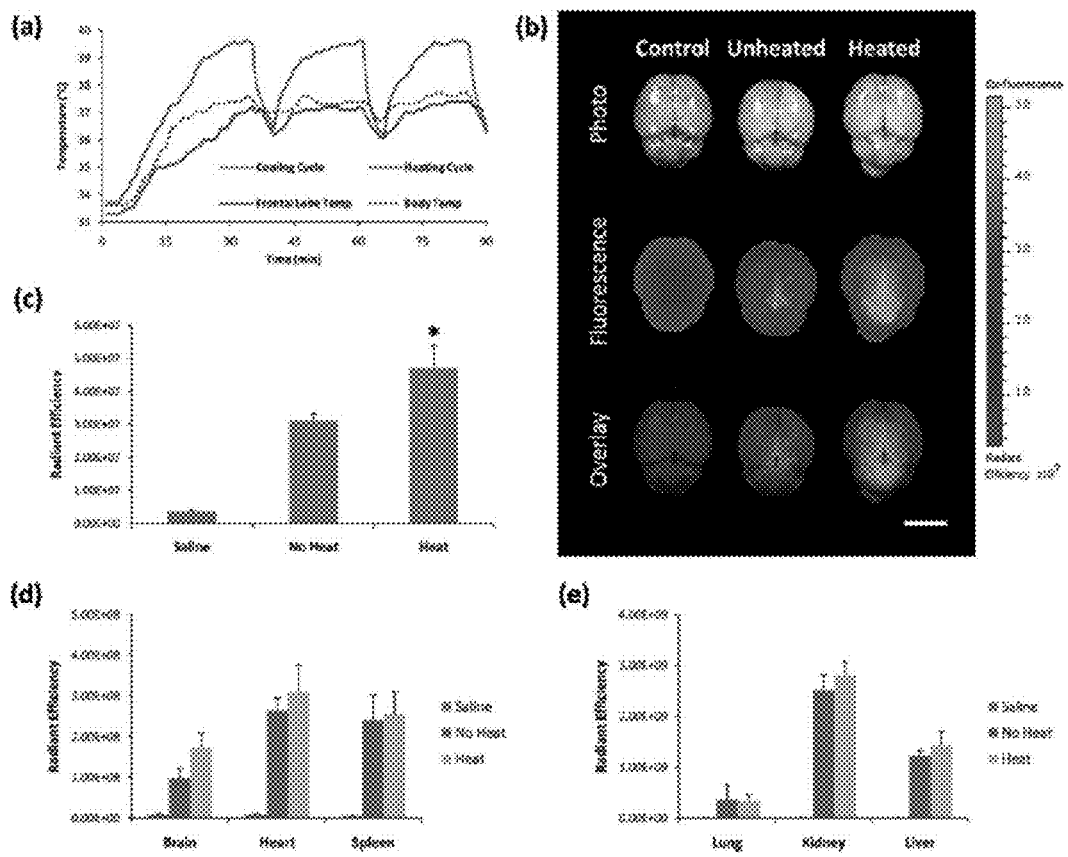
FIG. 17: (a) The graph shows the temperature of the cerebellum during Cooling Cycles in blue and Heating Cycles in red. Shown as the black dotted line, is the body temperature taken with a rectal thermometer over the course of the 90 minute experiment. The Frontal Lobe temperature taken over the course of the 90 minute experiment is shown by the gray line. (b) Shown is the scanned IVIS image displaying a photograph of the brains and the fluorescent uptake of fluorescent labeled Synb1-ELP-GGC taken from a control animal, an unheated animal and an animal where the cerebellum was heated by thermal cycling. Scale bar: 4.0 mm. (c) The graph shows the Synb1-ELP-GGC Average Radiant Efficiency of the cerebellum ±SE taken from a control animal, an unheated animal and an animal where the cerebellum was heated by thermal cycling. Statistics were taken using the student's t-test. *No Heat vs Heat, P<0.05, n=3. (d) The graph shows the Synb1-ELP-GGC Average Radiant Efficiency of the brain, heart, spleen, (e) lungs, kidney and liver±SE taken from a control animal, an unheated animal and an animal where the cerebellum was heated by thermal cycling, n=3.

It has been recently reported that the S100B inhibitory peptide, TRTK12, modulates mutant ataxin-1 mediated PC morphology in slice cultures and improves behavioral abnormalities in SCA1 mice (Vig et al., 2011). The TRTK12 peptide was developed from the high specificity, S100B binding protein CapZ (Charpentier et al., 2010). The possibility of TRTK12 non-specific interactions is limited by the extensive biophysical characterization of the TRTK12-S100B interaction using solution NMR and X-ray crystallography techniques (Inman et al., 2002, Charpentier et al., 2010). To further amplify the therapeutic benefits and enhance TRTK12 delivery to the cerebellum, the first thermally responsive S100B inhibitory peptide, Synb1-ELP-TRTK, was designed. The peptide interacts with its molecular target S100B (FIG. 11). Though the S100B binding affinities of both Synb1-ELP- TRTK and TRTK12 peptide (alone) are in the nanomolar range (FIGS. 12 and 13), it is believed that the Synb1-ELP-TRTK polypeptide has an added advantage over TRTK12 alone, due to its enhanced intracellular accumulation from the CPP Synb1 and from the thermal response of ELP. To support the argument that the TRTK12 peptide of the Synb1-ELP-TRTK polypeptide maintains its biological function, it was shown that Synb1-ELP-TRTK reduces S100B-RAGE mediated uptake (FIG. 14) as well as S100B induced oxidative damage in mutant ataxin-1 expressing cells (FIG. 16). Furthermore, it was shown that thermal targeting of Synb1-ELP-GGC by applying local hyperthermia to the cerebellum after systemic administration of the polypeptide is a novel treatment strategy to increase therapeutic peptide uptake and delivery to the cerebellum (FIG. 17).

Figure 15:
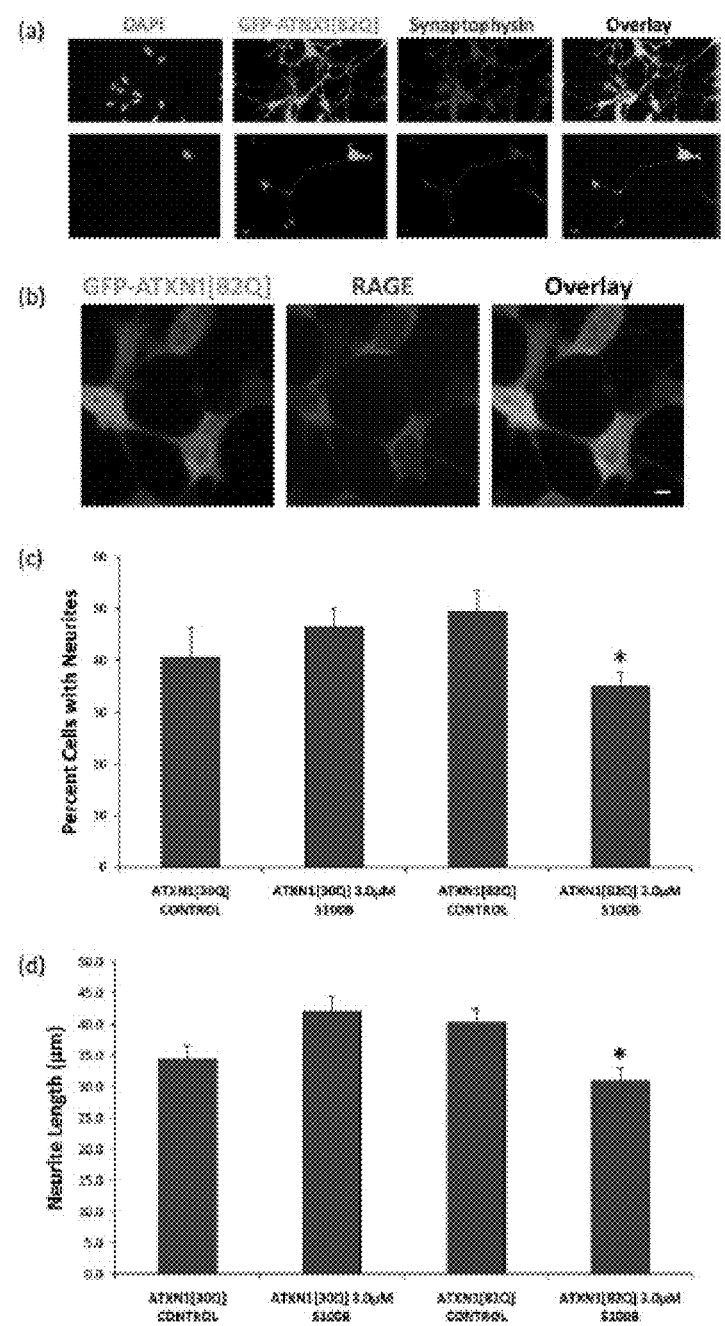
FIG. 15: GFP-ATXN1[82Q] SHSY5Y stable cells were placed on 2-well slides and subjected to treatment with 25 nM TPA for 3 days to produce differentiated SHSY5Y cells. Next, slides were fixed and probed with (a &b) GFP, (a) Synaptophycin and (b) RAGE antibodies and fluorescent secondary antibodies Alexa 488 and Alexa 546 followed by DAPI staining. Scale Bars: 10 m. Differentiated SHSY5Y cells were treated with 3.0 μM S100B for 48 hrs and neurite changes were visualized under the microscope. (c) Data is shown as MEAN±STDEV of the percentage of cells with neurites, n=100. (d) Data is shown as MEAN±SE of neurite length, n=100. Statistics were taken using student's t-test. *P<0.05.
Figure 18:
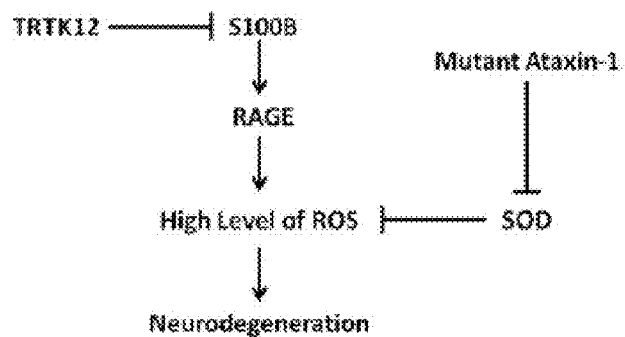
FIG. 18: The diagram depicts the S100B signaling pathway in SCA1. S100B activates the RAGE receptor producing ROS. Under normal conditions SOD inhibits high levels of ROS. However, due to expression of the mutant ataxin-1 protein, SOD function is reduced allowing ROS to accumulate, causing neurodegeneration in SCA1. This S100B induced oxidative damage pathway can be inhibited by TRTK12, Synb1-ELP-TRTK or like peptides.

In this study, the role of BG in the SCA1 pathogenesis is further characterized and it is shown that S100B-RAGE signaling directly influences degeneration of mutant ataxin-1 expressing neurons by an oxidative stress mechanism (FIGS. 15, 16 & 18). The RAGE receptor is highly expressed in PCs of the cerebellum; and due to the loss of SOD function, mutant ataxin-1 expressing neurons are more susceptible to oxidative damage through S100B-RAGE signaling (Kim et al., 2003a, Kim et al., 2003b, Vig et al., 2006, Ryu et al., 2010). Thus, signaling mechanisms that stimulate ROS production in SCA1 PCs are major contributing factors in oxidative stress mediated neurodegeneration. Reports indicate that S100B transport is mediated by a RAGE dependent uptake mechanism both in vitro and in vivo (Vig et al., 2006, Perrone et al., 2008). The presence of S100B vacuoles in degenerating SCA1 PCs along with the improvements in SCA1 mice by TRTK12 treatment is striking evidence indicating the neurotoxic effects of S100B signaling (Vig et al., 2006, Vig et al., 2009, Vig et al., 2011). S100B is a damage associated protein, where S100B-RAGE signaling causes the production of ROS and oxidative stress (Rothermundt et al., 2003, Donato et al., 2009, Sorci et al., 2010). Furthermore, S100B has been reported to play a neurodegenerative role in brain injury, Alzheimer's disease as well as Down syndrome (Griffin et al., 1989, Kato et al., 1990, Rothermundt et al., 2003, Mori et al., 2010). S100B has been shown to increase tau protein hyper-phosphorylation and exacerbates cerebral amyloidosis in the Alzheimer's disease mouse model (Esposito et al., 2008, Mori et al., 2010). Interestingly, S100B ablation has been shown to improve Alzheimer's disease pathology in Tg mice (Roltsch et al., 2010). Since S100B-specific inhibitors are not currently available, the use of S100B peptide based inhibitors is a novel treatment strategy for reducing S100B mediated effects in a number of neurodegenerative diseases where high S100B levels contribute to pathology.

This work also presents the novel strategy of utilizing the thermally responsive Elastin-like polypeptide for thermally targeted delivery of agents to the cerebellum to treat neurological disorders. Thermal targeting of ELP to tumors has shown promising results (Meyer et al., 2001, Liu et al., 2006, Dreher et al., 2007), and a thermal cycling protocol similar to that used in this work has been shown to be beneficial compared to long sessions of constant hyperthermia (Dreher et al., 2007). These previous studies have demonstrated that ELP has characteristics, including a long plasma half-life, resistance to proteolysis, tumor targeting (Liu et al., 2006), and the ability to escape the vasculature and enter tumor cells (Bidwell and Raucher, 2010), that are desirable in a drug delivery agent. However, there has been no demonstration of the use of ELP for thermally targeted delivery to the brain. The results shown here indicate that brain delivery is feasible, and the technology necessary for delivery of hyperthermia to the brain currently exists in the clinical setting in the form of MRI—guided high intensity focused ultrasound (Ram et al., 2006, Martin et al., 2009, Hertzberg et al., 2010). Future work will examine the ability of ELP to deliver the TRTK12 peptide to PCs in vivo, and will define the efficacy of this approach for treatment of SCA1 using a Tg mouse model. If efficacious, this approach can be taken beyond TRTK12 peptide delivery and SCA1. The ELP delivery system can be modified to accommodate a large repertoire of cargo, including peptides, drugs, or DNA to treat a multitude of CNS diseases making a huge impact on the neurodegenerative field (Bidwell and Raucher, 2005, Bidwell et al., 2007, Chen et al., 2008, Bidwell and Raucher, 2009, MacKay et al., 2009, Raucher et al., 2009).

Throughout this document, various references are mentioned. All such references are incorporated herein by reference. Also incorporated by reference are U.S. patent application Ser. No. 12/162,283 to Raucher et al. for Thermally Targeted Delivery of Doxorubicin by Elastin-Like Polymers; Ser. No. 12/422,970 to Raucher, et al. for Targeted Delivery of Therapeutic Polypeptides by Thermally-Responsive Polymers; Ser. No. 12/422,975 to Raucher, et al. for Inhibition of Metastasis by Cell-Penetrating Peptides; and Ser. No. 12/964,099 to Raucher, et al. for Composition for Targeted Delivery of an Active Agent and Method for Use Thereof. Also incorporated by reference are the references set forth in the following list:

REFERENCES

1. Abdipranoto A, et al. (2008). The role of neurogenesis in neurodegenerative diseases and its implications for therapeutic development. *CNS Neurol Disord Drug Targets*. April; 7(2): 187-210.
2. Adami C, et al. (2004). S100B-stimulated NO production by BV-2 microglia is independent of RAGE transducing activity but dependent on RAGE extracellular domain. *Biochim Biophys Acta* 1742:169-177.
3. Adenot, M, et al (2007). Applications of a blood-brain barrier technology platform to predict CNS penetration of various chemotherapeutic agents. 2. Cationic peptide vectors for brain delivery. Chemotherapy, 53(1):73-6.
4. Allen T M. (1998). Liposomal drug formulation: rationale for development and what we can expect in the future. Drugs. 56:747-756.
5. Barger S W, et al. (1995). S100 beta protects hippocampal neurons from damage induced by glucose deprivation. *Brain Res* 677(1):167-170.
6. Bianchi R, et al. (1996). S-100 (alpha and beta) binding peptide (TRTK-12) blocks S-100/GFAP interaction: identification of a putative S-100 target epitope within the head domain of GFAP. Biochim Biophys Acta 1313:258-267.
7. Bidwell G L, 3rd, et al. (2009). Targeting a c-Myc inhibitory polypeptide to specific intracellular compartments using cell penetrating peptides. *J Control Release* 135:2-10.
8. Bidwell G L, 3rd, et al. (2006). Enhancing the antiproliferative effect of topoisomerase II inhibitors using a polypeptide inhibitor of c-Myc, *Biochem Pharmacol* 71:248-256
9. Bidwell G L, 3rd, et al. (2007). Development of elastin-like polypeptide for thermally targeted delivery of doxorubicin. *Biochem Pharmacol* 73:620-631.

10. Bidwell G L, 3rd, et al. (2005) Application of thermally responsive polypeptides directed against c-Myc transcriptional function for cancer therapy. *Mol Cancer Ther* 4:1076-1085.
11. Bidwell G L, 3rd et al. (2009) Therapeutic peptides for cancer therapy. Part I—peptide inhibitors of signal transduction cascades. *Expert Opin Drug Deliv* 6:1033-1047.
12. Bidwell G L, 3rd, et al. (2010) Cell penetrating elastin-like polypeptides for therapeutic peptide delivery. *Adv Drug Deliv Rev* 62:1486-1496.
13. Bidwell G L, 3rd, et al. (2010) A thermally targeted peptide inhibitor of symmetrical dimethylation inhibits cancer-cell proliferation. *Peptides* 31:834-841.
14. Bocedi A, et al. (2004) Binding of anti-HIV drugs to human serum albumin. *IUBMB Life* 56:609-614.
15. Brozzi, F., et al., (2009) S100B Protein Regulates Astrocyte Shape and Migration via Interaction with Src Kinase: IMPLICATIONS FOR ASTROCYTE DEVELOPMENT, ACTIVATION, AND TUMOR GROWTH. *J Biol Chem.*, 284(13):8797-811.
16. Burright E N, (1995) SCA1 transgenic mice: a model for neurodegeneration caused by an expanded CAG trinucleotide repeat. *Cell* 82:937-948.
17. Cassidy J, et al. (1989). Activity of N-(2-hydroxypropyl) methacrylamide copolymers containing daunomycin against a rat tumour model. *Biochem. Pharmacol.* 38(6): 875-879.
18. Charpentier T H, et al. (2010). The effects of CapZ peptide (TRTK-12) binding to S100B-Ca2+ as examined by NMR and X-ray crystallography. *J Mol Biol* 396:1227-1243.
19. Chen, H. K., et al. (2003). Interaction of Akt-phosphorylated ataxin-1 with 14-3-3 mediates neurodegeneration in spinocerebellar ataxia type 1. *Cell*, 2003. 113(4)457-68.
20. Chen T H, et al. (2008). Intelligent biosynthetic nanobiomaterials (IBNs) for hyperthermic gene delivery. *Pharm Res* 25:683-691.
21. Cheung Y T, et al. (2009). Effects of all-trans-retinoic acid on human SH-SY5Y neuroblastoma as in vitro model in neurotoxicity research. *Neurotoxicology* 30:127-135.
22. Custer S K, et al. (2006). Bergmann glia expression of polyglutamine-expanded ataxin-7 produces neurodegeneration by impairing glutamate transport. *Nat Neurosci* 9(10): 1302-11.
23. C. de Chiara, C. Giannini, S. Adinolfi, J. de Boer, S. Guida, A. Ramos, C. Jodice, D. Kioussis, A. Pastore, The AXH molecule: an independently folded domain common to ataxin-1 and HBP1. *FEBS Letters*, Vol. 551:1, pp. 107-112
24. Dewhirst M W, et al. (1997). Hyperthermic treatment of malignant diseases: current status and a view toward the future. *Semin. Oncol.* 24(6):616-625.
25. Donato R (1991). Perspectives in S-100 protein biology. Review article. *Cell Calcium* 12:713-726.
26. Donato R (1999). Functional roles of S100 proteins, calcium-binding proteins of the EF-hand type. *Biochim Biophys Acta* 1450(3):191-231.
27. Donato R (2001). S100: a multigenic family of calcium-modulated proteins of the EF-hand type with intracellular and extracellular functional roles. *Int J Biochem Cell Biol* 33:637-668.
28. Donato R, et al. (2009). S100B's double life: intracellular regulator and extracellular signal. *Biochim Biophys Acta* 1793:1008-1022.
29. Dreher M R, et al. (2007) Thermal cycling enhances the accumulation of a temperature-sensitive biopolymer in solid tumors. *Cancer Res* 67(9):4418-4424.
30. Drin G, et al. (2002). Peptide delivery to the brain via adsorptive-mediated endocytosis: advances with SynB vectors. *AAPS PharmSci*, 4(4):E26.
31. Duncan R, et al. (1998). Preclinical toxicology of a novel polymeric antitumour agent: HPMA copolymer-doxorubicin (PK1). *Hum. Exp. Toxicol.* 17(2):93-104.
32. Emamian E S, et al. (2003). Serine 776 of ataxin-1 is critical for polyglutamine-induced disease in SCA1 transgenic mice. *Neuron*, 38(3):375-87.
33. Esposito G, et al. (2008). S100B induces tau protein hyperphosphorylation via Dickopff-1 up-regulation and disrupts the Wnt pathway in human neural stem cells. *J Cell Mol Med* 12:914-927.
34. Falk M H et al., (2001) Hyperthermia in oncology. *Int J Hyperthermia*, 17(1):1-18.
35. Frizzo J K, et al. (2004). S100B-mediated inhibition of the phosphorylation of GFAP is prevented by TRTK-12. *Neurochem Res* 29:735-740.
36. Goold R, et al. (2007). Down-regulation of the dopamine receptor D2 in mice lacking ataxin 1. *Hum Mol Genet*, 16(17):2122-34.
37. Griffin W S, et al. (1989). Brain interleukin 1 and S-100 immunoreactivity are elevated in Down syndrome and Alzheimer disease. *Proc Natl Acad Sci USA* 86(19):7611-7615.
38. Hearst S M, et al. (2011). The Design and Delivery of a Thermally Responsive Peptide to Inhibit S100B-Mediated Neurodegeneration, *Neuroscience* 197: 369-380.
39. Hearst S M, et al. (2010). Dopamine D2 receptor signaling modulates mutant ataxin-1 S776 phosphorylation and aggregation. *J Neurochem* 114:706-716.
40. Hertzberg Y, et al. (2010). Ultrasound focusing using magnetic resonance acoustic radiation force imaging: application to ultrasound transcranial therapy. *Med Phys* 37:2934-2942.
41. Hilhorst R, et al. (2009) Peptide microarrays for detailed, high-throughput substrate identification, kinetic characterization, and inhibition studies on protein kinase A. *Anal Biochem,* 387(2):150-61.
42. Hunter T. (2000). Signaling—2000 and beyond. *Cell,* 100(1):113-27.
43. Huttunen H J, et al. (2000). Coregulation of neurite outgrowth and cell survival by amphoterin and S100 proteins through receptor for advanced glycation end products (RAGE) activation. *J Biol Chem* 275(51):40096-40105.
44. Inman K G, et al. (2002). Solution NMR structure of S100B bound to the high-affinity target peptide TRTK-12. *J Mol Biol* 324:1003-1014.
45. Ivanenkov V V, (1995). Characterization of S-100b binding epitopes. Identification of a novel target, the actin capping protein, CapZ. *J Biol Chem* 270:14651-14658.
46. Jagannathan J, et al. (2009). High-intensity focused ultrasound surgery of the brain: part 1—A historical perspective with modern applications. *Neurosurgery,* 64(2):201-10; discussion 210-1.
47. Jaaskelainen J (2003). Non-invasive transcranial high intensity focused ultrasound (HIFUS) under MRI thermometry and guidance in the treatment of brain lesions. *Acta Neurochir Suppl* 88:57-60.
48. Jiang H, et al. (2004). Parkin protects human dopaminergic neuroblastoma cells against dopamine-induced apoptosis. *Hum Mol Genet* 13:1745-1754.
49. Jones M, J. L. (1999). Polymeric micelles: a new generation of colloidal drug carriers. *Eur. J. Pharm. Biopharm.* 48:101-111.

50. Kandel E S, et al, (1999). The regulation and activities of the multifunctional serine/threonine kinase Akt/PKB. *Exp Cell Res,* 253(1):210-29.

51. Kato K, et al. (1990). Enhancement of S-100 beta protein in blood of patients with Down's syndrome. *J Mol Neurosci* 2(2):109-113.

52. Kim S J, et al. (2003). Oxidative stimuli affect polyglutamine aggregation and cell death in human mutant ataxin-1-expressing cells. *Neurosci Lett* 348:21-24.

53. Kim S J, et al. (2003). Polyglutamine-expanded ataxin-1 recruits Cu/Zn-superoxide dismutase into the nucleus of HeLa cells. *Biochem Biophys Res Commun* 307:660-665.

54. Kissel M, et al. (2001). Synthetic macromolecular drug carriers: biodistribution of PNAPM copolymers and their accumulation in solid rat tumors, *PDA J Pharm Sci Technol* 55:191-201.

55. Koeppen A H (2005). The pathogenesis of spinocerebellar ataxia. *Cerebellum* 4(1):62-73.

56. Kong G, et al. (1999). Hyperthermia and liposomes, *Int J Hyperthermia* 15(5):345-370.

57. Langer R. (1998). Drug delivery and targeting. *Nature (Lond.).* 392 (Suppl.):5-10.

58. Leclerc E, et al. (2007). S100B and S100A6 differentially modulate cell survival by interacting with distinct RAGE (receptor for advanced glycation end products) immunoglobulin domains. *J Biol Chem* 282:31317-31331.

59. Li B, et al. (2001). Hydrophobic hydration is an important source of elasticity in elastin-based biopolymers. *J Am Chem Soc* 123:11991-11998.

60. Liu W, et al. (2006) Tumor accumulation, degradation and pharmacokinetics of elastin-like polypeptides in nude mice. *J Control Release* 116(2):170-178.

61. Liu Y, et al. (2008) Novel interaction of the dopamine D2 receptor and the $Ca^{2+}$ binding protein S100B: role in D2 receptor function. *Mol Pharmacol,* 74(2): 371-8.

62. Lordkipanidze T, et al., (2005) Purkinje cell dendrites grow in alignment with Bergmann glia, *Glia* 51 229-234.

63. MacKay J A, et al. (2009). Self-assembling chimeric polypeptide-doxorubicin conjugate nanoparticles that abolish tumours after a single injection. *Nat Mater* 8:993-999.

64. Mackie S, et al, (2005). Novel brain 14-3-3 interacting proteins involved in neurodegenerative disease. *Febs J,* 272(16):4202-10.

65. Maeda H, et al. (1992). Conjugates of anticancer agents and polymers: advantages of macromolecular therapeutics in vivo. *Bioconjug. Chem.* 3(5):351-362.

66. Martin E, et al. (2009). High-intensity focused ultrasound for noninvasive functional neurosurgery. *Ann Neurol* 66:858-861.

67. Massodi, et al. (2005). Evaluation of cell penetrating peptides fused to elastin-like polypeptide for drug delivery, *J Control Release* 108:396-408.

68. Massodi I, et al. (2009). Application of thermally responsive elastin-like polypeptide fused to a lactoferrin-derived peptide for treatment of pancreatic cancer. *Molecules* 14:1999-2015.

69. Matilla-Duenas A, et al. (2008) Clinical, genetic, molecular, and pathophysiological insights into spinocerebellar ataxia type 1. *Cerebellum* 7:106-114.

70. McClintock K A, et al. (2000). A logical sequence search for S100B target proteins. *Protein Sci* 9:2043-2046.

71. Meyer D E, et al. (1999). Purification of recombinant proteins by fusion with thermally-responsive biopolypeptides. *Nat Biotechnol* 17:1112-1115.

72. Meyer D E, et al. (2001) Targeting a Genetically Engineered Elastin-like Polypeptide to Solid Tumors by Local Hyperthermia. *Cancer Res* 61:1548-1554.

73. Minko T, et al. (1998). HPMA copolymer bound adriamycin overcomes MDR1 gene encoded resistance in a human ovarian carcinoma cell line. *J Control Release.* July 31 54(2):223-233.

74. Moktan S, et al. (2010). A thermally responsive biopolymer conjugated to an acid-sensitive derivative of paclitaxel stabilizes microtubules, arrests cell cycle, and induces apoptosis. *Invest New Drugs.*

75. Mori T, et al. (2010) Overexpression of human S100B exacerbates cerebral amyloidosis and gliosis in the Tg2576 mouse model of Alzheimer's disease. *Glia* 58:300-314.

76. Neve K A, et al. (2004) Dopamine receptor signaling. *J Recept Signal Transduct Res,* 24(3):165-205.

77. Nishida H, et al. (2007). Direct astrocytic contacts regulate local maturation of dendritic spines, *J Neurosci* 27:331-340.

78. Ohkawa K, et al. (1993) Bovine serum albumin-doxorubicin conjugate overcomes multidrug resistance in a rat hepatoma. *Cancer Res.* 53(18):4238-4242.

79. Orr H T, et al., (2007) Trinucleotide repeat disorders. *Annu Rev Neurosci* 30:575-621.

80. Perrone L, et al. (2008). RAGE recycles at the plasma membrane in S100B secretory vesicles and promotes Schwann cells morphological changes. *J Cell Physiol* 217: 60-71.

81. Presgraves S P, et al. (2004). Terminally differentiated SH-SY5Y cells provide a model system for studying neuroprotective effects of dopamine agonists. *Neurotox Res* 5:579-598.

82. Ram Z, et al. (2006). Magnetic resonance imaging-guided, high-intensity focused ultrasound for brain tumor therapy. *Neurosurgery* 59:949-955; discussion 955-946.

83. Raucher D, et al. (2009). Therapeutic peptides for cancer therapy. Part II—cell cycle inhibitory peptides and apoptosis-inducing peptides. *Expert Opin Drug Deliv* 6:1049-1064.

84. Reeves R H, et al. (1994) Astrocytosis and axonal proliferation in the hippocampus of S100b transgenic mice. *Proc Natl Acad Sci USA* 91(12):5359-5363.

85. Roltsch E, et al. (2010). PSAPP mice exhibit regionally selective reductions in gliosis and plaque deposition in response to S100B ablation. *J Neuroinflammation* 7:78.

86. Rothermundt M, et al., (2003). S100B in brain damage and neurodegeneration. *Microsc Res Tech* 60(6):614-632.

87. Rousselle C, et al. (2000). New advances in the transport of doxorubicin through the blood-brain barrier by a peptide vector-mediated strategy. *Mol Pharmacol* 57:679-686.

88. Ryser H J, et al. (1978). Conjugation of methotrexate to poly(L-lysine) increases drug transport and overcomes drug resistance in cultured cells. *Proc. Natl. Acad. Sci. USA.* 75(8):3867-3870.

89. Ryu J, et al. (2010). Oxidative stress-enhanced SUMOylation and aggregation of ataxin-1: Implication of JNK pathway. *Biochem Biophys Res Commun* 393:280-285.

90. Sarantseva S V, et al. (2009). [Protein transduction domain peptide mediates delivery to the brain via the blood-brain barrier in *Drosophila*]. *Biomed Khim* 55:41-49.

91. Schwarze S R, et al. (1999) In vivo protein transduction: delivery of a biologically active protein into the mouse. *Science,* 285(5433):1569-72.

92. Seymour L W, et al. (1987). Daunomycin- and adriamycin-N-(2-hydroxypropyl)methacrylamide copolymer conjugates; toxicity reduction by improved drug-delivery. *Cancer. Treat. Rev.* 14(3-4):319-327.
93. Shcherbo D, et al. (2010). Near-infrared fluorescent proteins. *Nat Methods* 7:827-829.
94. Skinner P J, et al. (2001). Altered trafficking of membrane proteins in purkinje cells of SCA1 transgenic mice. *Am J Pathol* 159:905-913.
95. Sorci G, et al. (2010). S100B Protein, A Damage-Associated Molecular Pattern Protein in the Brain and Heart, and Beyond. *Cardiovasc Psychiatry Neurol* 2010.
96. St'astny M, et al. (1999). A possibility to overcome P-glycoprotein (PGP)-mediated multidrug resistance by antibody-targeted drugs conjugated to N-(2-hydroxypropyl) methacrylamide (HPMA) copolymer carrier. *Eur. J. Cancer.* 35(3):459-466.
97. Takahashi, et al. (2002) Clinical application of hyperthermia combined with anticancer drugs for the treatment of solid tumors, *Surgery* 131:S78-84.
98. Takano K, et al. (2007). A dibenzoylmethane derivative protects dopaminergic neurons against both oxidative stress and endoplasmic reticulum stress. *Am J Physiol Cell Physiol* 293:C1884-1894.
99. Takakura Y, et al. (1990) Disposition characteristics of macromolecules in tumor-bearing mice. *Pharm. Res.* 7(4): 339-346.
100. Torchilin V P. (1998). Polymer-coated long-circulating microparticulate pharmaceuticals. *J. Microencapsul.* 15:1-19.
101. Urry D. W. (1992). Free energy transduction in polypeptides and proteins based on inverse temperature transitions. *Prog. Biophys. Mol. Biol.* 57(1):23-57.
102. Urry D W, et al., (1991). Temperature of Polypeptide Inverse Temperature Transition Depends on Mean Residue Hydrophobicity. *J. Am. Chem. Soc,* 113:4346-4348.
103. Vig P J, et al. (2011) Glial S100B Protein Modulates Mutant Ataxin-1 Aggregation and Toxicity: TRTK12 Peptide, a Potential Candidate for SCA1 Therapy. *Cerebellum.*
104. Vig P J, et al. (2006). Glial S100B Positive Vacuoles In Purkinje Cells: Earliest Morphological Abnormality In SCA1 Transgenic Mice. *J Neurol Sci Turk* 23:166-174.
105. Vig P J, et al. (2009). Bergmann glial S100B activates myo-inositol monophosphatase 1 and Co-localizes to purkinje cell vacuoles in SCA1 transgenic mice. *Cerebellum* 8:231-244.
106. Vig P J, et al, (1994). Decreased insulin-like growth factor I-mediated protein tyrosine phosphorylation in human olivopontocerebellar atrophy and lurcher mutant mouse, *J Neurol Sci* 124:38-44.
107. Vig P J, et al, (1999). The effects of calbindin D-28K and parvalbumin antisense oligonucleotides on the survival of cultured Purkinje cells, *Res Commun Mol Pathol Pharmacol* 103:249-259.
108. Vig P J, et al, (1998) Reduced immunoreactivity to calcium-binding proteins in Purkinje cells precedes onset of ataxia in spinocerebellar ataxia-1 transgenic mice. *Neurology,* 50(1):106-13.
109. Vig P J, et al, (2000). Relationship between ataxin-1 nuclear inclusions and Purkinje cell specific proteins in SCA-1 transgenic mice, *J Neurol Sci* 174:100-110.
110. Vig P J, et al, (1996). Decreased parvalbumin immunoreactivity in surviving Purkinje cells of patients with spinocerebellar ataxia-1, *Neurology* 47(1):249-253.
111. Vig P J, et al, (2006). Glial S100B Positive Vacuoles In Purkinje Cells: Earliest Morphological Abnormality In SCA1 Transgenic Mice, *J Neurol Sci Turk* 23(3)166-174.
112. Vig P J S (2009). S100B-A common connection between depression and cerebellar disorders, *Bioscience Hypothesis* 2 (2009) 343-344.
113. Vig P J S, et al. (2009). Glial response to polyglutamine-mediated stress, *Biosci Hypotheses* 2 (2009) 148-150.
114. Vig P J S, (2011). Suppression of Calbindin-D28K Expression Exacerbates SCA1 phenotype in a Disease Mouse Model. *Cerebellum,* 2011 (Published online, Nov. 11, 2011).
115. Vivian J T, et al. (2001). Mechanisms of tryptophan fluorescence shifts in proteins. *Biophys J* 80:2093-2109.
116. Weljie A M, et al. (2000). Tryptophan fluorescence of calmodulin binding domain peptides interacting with calmodulin containing unnatural methionine analogues. *Protein Eng* 13:59-66.
117. Whitaker-Azmitia P M (1997). Transgenic mice overexpressing the neurotrophic factor S-100 beta show neuronal cytoskeletal and behavioral signs of altered aging processes: implications for Alzheimer's disease and Down's syndrome. *Brain Res* 776(1-2)51-60.
118. Wilder P T, et al. (2006). Recognition of the tumor suppressor protein p53 and other protein targets by the calcium-binding protein S100B. *Biochim Biophys Acta* 1763(11):1284-1297.
119. Winningham-Major F, (1989) Neurite extension and neuronal survival activities of recombinant S100 beta proteins that differ in the content and position of cysteine residues. *J Cell Biol* 109:3063-3071.
120. Wright N T, et al. (2009). S100A1: Structure, Function, and Therapeutic Potential. *Curr Chem Biol* 3:138-145.
121. Yamaoka T, et a. (1994). Distribution and tissue uptake of poly(ethylene glycol) with different molecular weights after intravenous administration to mice. *J. Pharm. Sci.* 83(4):601-606.
122. Yeung T K, et al. (1991) Reduced cardiotoxicity of doxorubicin given in the form of N-(2-hydroxypropyl) methacrylamide conjugates: and experimental study in the rat. *Cancer Chemother. Pharmacol.* 29(2):105-111.
123. Zimmer D B, et al., (2005) S100-mediated signal transduction in the nervous system and neurological diseases. *Cell Mol Biol* (Noisy-le-grand) 51(2):201-214.
124. Zimmer D B, et al. (2010) The Calcium-Dependent Interaction of S100B with Its Protein Targets. Cardiovasc Psychiatry Neurol.
125. Zoghbi H Y et al., (2009) Pathogenic Mechanisms of a Polyglutamine-mediated Neurodegenerative Disease, Spinocerebellar Ataxia Type 1, *J Biol Chem* 284:7425-7429.
126. U.S. Patent Application Publication No. 2007/0135340 to Rosenthal, et al. for IGF-1 NOVEL PEPTIDES.
127. U.S. Patent Application Publication No. 2007/0265197 to Furgeson, et al. for ELASTIN-LIKE POLYMER DELIVERY VEHICLES.
128. U.S. Patent Application Publication No. 2005/0143310 to Hirashima, et al. for NOVEL REMEDIES FOR NEURODEGENERATIVE DISEASE.
129. U.S. Patent Application Publication No. 2003/0211990 to Sieg, et al. for NEURAL REGENERATION PEPTIDES AND METHODS FOR THEIR USE IN TREATMENT OF BRAIN DAMAGE

INCORPORATION BY REFERENCE

All publications, patents, and patent applications mentioned in this specification are herein incorporated by reference to the same extent as if each individual publication, patent, or patent application was specifically and individually indicated to be incorporated by reference.

What is claimed is:

1. A composition, comprising
   (a) a therapeutic compound, wherein the therapeutic compound comprises a therapeutic polypeptide useful for the treatment of a neurodegenerative disease;
   (b) a cell penetrating peptide (CPP);
   (c) a spacer comprising an amino acid sequence WPGSGG (SEQ ID NO: 41); and
   (d) a thermal targeting polypeptide (TTP), comprising an elastin-like polypeptide (ELP) comprising the sequence -(VPGXG(SEQ ID NO: 1))n-, wherein n is an integer from about 30 to about 240, and wherein the elastin-like polypeptide is fused to the therapeutic polypeptide.

2. The composition of claim 1, wherein the CPP is selected from the group consisting of: TAT, Penetratin (Antp), Bac, SynB1, Poly-arginine, VP22, Transportan, MAP, pVEC, MTS, hCT derived, MPG, Buforin 2, PEP-1, Magainin 2, Oct6, and M918.

3. The composition of claim 1, wherein the CPP is selected from a polypeptide comprising the polypeptides set forth in Table 1.

4. The composition of claim 3, wherein each X is independently selected from valine, glycine, and alanine such that the Xs are provided in a 5:3:2 ratio.

5. The composition of claim 3, wherein each X is independently selected from valine, glycine, and alanine such that the Xs are provided in a 1:7:8 ratio.

6. The composition of claim 3, wherein each X is independently selected from valine, glycine, and alanine such that the Xs are provided in a 3:1:1 ratio.

7. The composition of claim 1, and further comprising a carrier polypeptide.

8. The composition of claim 1, wherein the CPP comprises the amino acid sequence of RGGRLSYSRRRFSTSTGR (SEQ ID NO: 11).

9. The composition of claim 8, wherein the therapeutic polypeptide (TP) comprises the amino acid sequence of FHCVPRDLSWLDLEANMCLP (SEQ ID NO: 29).

10. The composition of claim 8, wherein the therapeutic polypeptide (TP) comprises the amino acid sequence of TYADFIASGRTGRRNAI (SEQ ID NO: 30).

11. The composition of claim 8, wherein the therapeutic polypeptide (TP) comprises the amino acid sequence of TRTKIDWNKILS (SEQ ID NO: 31).

12. The composition of claim 8, wherein the therapeutic polypeptide (TP) comprises the amino acid sequence of EDCIPKWKGCVNRHGDCCE-GLECWKRRRSFEVCVPKTPKT (SEQ ID NO: 33).

13. The composition of claim 8, wherein the therapeutic polypeptide (TP) comprises the amino acid sequence of an AXH domain of ataxin-1.

14. The composition of claim 8, wherein each X is independently selected from valine, glycine, and alanine such that the Xs are provided in a 5:3:2 ratio.

15. The composition of claim 8, wherein each X is independently selected from valine, glycine, and alanine such that the Xs are provided in a 1:7:8 ratio.

16. The composition of claim 8, wherein each X is independently selected from valine, glycine, and alanine such that the Xs are provided in a 3:1:1 ratio.

17. A method of targeting a therapeutic compound to a desired region of a brain or a spinal cord of a subject, comprising:
   administering to the subject an effective amount of a composition comprising
      a therapeutic compound, wherein the therapeutic compound comprises
         a therapeutic polypeptide useful for the treatment of a neurodegenerative disease;

a cell penetrating peptide (CPP);
a spacer comprising an amino acid sequence WPGSGG (SEQ ID NO: 41); and
a thermal targeting polypeptide (TTP), comprising an elastin-like polypeptide (ELP) comprising the sequence -(VPGXG(SEQ ID NO: 1))n-, wherein n is an integer from about 30 to about 240, and wherein the elastin-like polypeptide is fused to the therapeutic polypeptide; and
applying heat to a desired region of the brain or spinal cord.

18. The method of claim 17, wherein the composition is administered to the subject intranasally.

19. The method of claim 17, wherein the cell penetrating peptide (CPP) is SynB1.

20. A composition, comprising:
(a) a therapeutic polypeptide useful for the treatment of a neurodegenerative disease;
(b) a cell penetrating peptide (CPP);
(c) a spacer comprising an amino acid sequence WPGSGG (SEQ ID NO: 41);
(d) a thermal targeting polypeptide (TTP), comprising an elastin-like polypeptide (ELP) comprising the sequence -(VPGXG(SEQ ID NO: 1))n-, wherein n is an integer from about 30 to about 240; and
(e) a carrier polypeptide,
wherein the therapeutic polypeptide is conjugated to at least one of the carrier polypeptide and the thermal targeting polypeptide.

21. The composition of claim 20, wherein the carrier polypeptide is selected from a group consisting of SEQ ID NO: 36, SEQ ID NO: 37, SEQ ID NO: 38, SEQ ID NO: 39, and SEQ ID NO: 40.

* * * * *

SEQUENCE LISTING

<160> NUMBER OF SEQ ID NOS: 41

<210> SEQ ID NO 1
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1

Val Pro Gly Xaa Gly
1               5

<210> SEQ ID NO 2
<211> LENGTH: 758
<212> TYPE: PRT
<213> ORGANISM: Artificial Sequence
<220> FEATURE:
<223> OTHER INFORMATION: Synthesized

<400> SEQUENCE: 2

Met Ser Lys Gly Pro Gly Val Gly Val Pro Gly Val Gly Val Pro Gly
1               5                   10                  15

Gly Gly Val Pro Gly Ala Gly Val Pro Gly Val Gly Val Pro Gly Val
                20                  25                  30

Gly Val Pro Gly Val Gly Val Pro Gly Gly Val Pro Gly Val Gly Ala
                35                  40                  45

Val Pro Gly Gly Val Pro Gly Val Gly Val Pro Gly Val Gly Val
    50                  55                  60

Pro Gly Gly Gly Val Pro Gly Ala Gly Val Pro Gly Val Gly Val Pro
65                  70                  75                  80

Gly Val Gly Val Pro Gly Val Gly Val Pro Gly Gly Val Gly Val Pro Gly
                85                  90                  95

Ala Gly Val Pro Gly Gly Val Pro Gly Val Gly Val Pro Gly Val
                100                 105                 110

Gly Val Pro Gly Gly Gly Val Pro Gly Ala Gly Val Pro Gly Val Gly
                115                 120                 125

Val Pro Gly Val Gly Val Pro Gly Val Gly Val Pro Gly Gly Gly Val
        130                 135                 140

Pro Gly Ala Gly Val Pro Gly Gly Gly Val Pro Gly Val Gly Val Pro
145                 150                 155                 160

Gly Val Gly Val Pro Gly Gly Gly Val Pro Gly Ala Gly Val Pro Gly
                165                 170                 175

Val Gly Val Pro Gly Val Gly Val Pro Gly Val Gly Val Pro Gly Gly
                180                 185                 190

Gly Val Pro Gly Ala Gly Val Pro Gly Gly Val Pro Gly Val Gly
        195                 200                 205

Val Pro Gly Val Gly Val Pro Gly Gly Gly Val Pro Gly Ala Gly Val
        210                 215                 220

Pro Gly Val Gly Val Pro Gly Val Gly Val Pro Gly Val Gly Val Pro
225                 230                 235                 240

Gly Gly Gly Val Pro Gly Ala Gly Val Pro Gly Gly Gly Val Pro Gly
                245                 250                 255

Val Gly Val Pro Gly Val Gly Val Pro Gly Gly Gly Val Pro Gly Ala
                260                 265                 270

-continued

Gly Val Pro Gly Val Gly Val Pro Gly Val Gly Val Pro Gly Val Gly
            275                 280                 285
Val Pro Gly Gly Gly Val Pro Gly Ala Gly Val Pro Gly Gly Gly Val
        290                 295                 300
Pro Gly Val Gly Val Pro Gly Val Gly Val Pro Gly Gly Gly Val Pro
305                 310                 315                 320
Gly Ala Gly Val Pro Gly Val Gly Val Pro Gly Val Gly Val Pro Gly
            325                 330                 335
Val Gly Val Pro Gly Gly Gly Val Pro Gly Ala Gly Val Pro Gly Gly
        340                 345                 350
Gly Val Pro Gly Val Gly Val Pro Gly Val Gly Val Pro Gly Gly Gly
            355                 360                 365
Val Pro Gly Ala Gly Val Pro Gly Val Gly Val Pro Gly Val Gly Val
        370                 375                 380
Pro Gly Val Gly Val Pro Gly Gly Gly Val Pro Gly Ala Gly Val Pro
385                 390                 395                 400
Gly Gly Gly Val Pro Gly Val Gly Val Pro Gly Val Gly Val Pro Gly
            405                 410                 415
Gly Gly Val Pro Gly Ala Gly Val Pro Gly Val Gly Val Pro Gly Val
        420                 425                 430
Gly Val Pro Gly Val Gly Val Pro Gly Gly Gly Val Pro Gly Ala Gly
            435                 440                 445
Val Pro Gly Gly Gly Val Pro Gly Val Gly Val Pro Gly Val Gly Val
        450                 455                 460
Pro Gly Gly Gly Val Pro Gly Ala Gly Val Pro Gly Val Gly Val Pro
465                 470                 475                 480
Gly Val Gly Val Pro Gly Val Gly Val Pro Gly Gly Gly Val Pro Gly
            485                 490                 495
Ala Gly Val Pro Gly Gly Gly Val Pro Gly Val Gly Val Pro Gly Val
        500                 505                 510
Gly Val Pro Gly Gly Gly Val Pro Gly Ala Gly Val Pro Gly Val Gly
            515                 520                 525
Val Pro Gly Val Gly Val Pro Gly Val Gly Val Pro Gly Gly Gly Val
        530                 535                 540
Pro Gly Ala Gly Val Pro Gly Gly Gly Val Pro Gly Val Gly Val Pro
545                 550                 555                 560
Gly Val Gly Val Pro Gly Gly Gly Val Pro Gly Ala Gly Val Pro Gly
            565                 570                 575
Val Gly Val Pro Gly Val Gly Val Pro Gly Val Gly Val Pro Gly Gly
        580                 585                 590
Gly Val Pro Gly Ala Gly Val Pro Gly Gly Gly Val Pro Gly Val Gly
            595                 600                 605
Val Pro Gly Val Gly Val Pro Gly Gly Gly Val Pro Gly Ala Gly Val
        610                 615                 620
Pro Gly Val Gly Val Pro Gly Val Gly Val Pro Gly Gly Gly Val Pro
625                 630                 635                 640
Gly Gly Gly Val Pro Gly Ala Gly Val Pro Gly Gly Gly Val Pro Gly
            645                 650                 655
Val Gly Val Pro Gly Val Gly Val Pro Gly Gly Gly Val Pro Gly Ala
        660                 665                 670
Gly Val Pro Gly Val Gly Val Pro Gly Val Gly Val Pro Gly Val Gly
            675                 680                 685

-continued

```
Val Pro Gly Gly Val Pro Gly Ala Gly Val Pro Gly Gly Val
    690             695                 700

Pro Gly Val Gly Val Pro Gly Val Gly Val Pro Gly Gly Gly Val Pro
705                 710                 715                 720

Gly Ala Gly Val Pro Gly Val Gly Val Pro Gly Val Gly Val Pro Gly
            725                 730                 735

Val Gly Val Pro Gly Gly Val Pro Gly Ala Gly Val Pro Gly Gly
            740                 745                 750

Gly Val Pro Gly Trp Pro
        755
```

<210> SEQ ID NO 3
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (4)..(4)
<223> OTHER INFORMATION: Xaa can be any naturally occurring amino acid

<400> SEQUENCE: 3

```
Val Pro Gly Xaa Gly
1               5
```

<210> SEQ ID NO 4
<211> LENGTH: 808
<212> TYPE: PRT
<213> ORGANISM: Artificial Sequence
<220> FEATURE:
<223> OTHER INFORMATION: Synthesized

<400> SEQUENCE: 4

```
Met Ser Lys Gly Pro Gly Val Gly Val Pro Gly Ala Gly Val Pro Gly
1               5                   10                  15

Gly Gly Val Pro Gly Ala Gly Val Pro Gly Gly Val Pro Gly Ala
            20                  25                  30

Gly Val Pro Gly Gly Gly Val Pro Gly Ala Gly Val Pro Gly Gly Gly
        35                  40                  45

Val Pro Gly Ala Gly Val Pro Gly Gly Val Pro Gly Ala Gly Val
    50                  55                  60

Pro Gly Gly Gly Val Pro Gly Ala Gly Val Pro Gly Gly Gly Val Pro
65                  70                  75                  80

Gly Ala Gly Val Pro Gly Val Gly Val Pro Gly Ala Gly Val Pro Gly
            85                  90                  95

Gly Gly Val Pro Gly Ala Gly Val Pro Gly Gly Gly Val Pro Gly Ala
            100                 105                 110

Gly Val Pro Gly Gly Val Pro Gly Ala Gly Val Pro Gly Gly Gly
        115                 120                 125

Val Pro Gly Ala Gly Val Pro Gly Gly Val Pro Gly Ala Gly Val
    130                 135                 140

Pro Gly Gly Gly Val Pro Gly Ala Gly Val Pro Gly Gly Gly Val Pro
145                 150                 155                 160

Gly Ala Gly Val Pro Gly Val Gly Val Pro Gly Ala Gly Val Pro Gly
            165                 170                 175

Gly Gly Val Pro Gly Ala Gly Val Pro Gly Gly Gly Val Pro Gly Ala
            180                 185                 190

Gly Val Pro Gly Gly Gly Val Pro Gly Ala Gly Val Pro Gly Gly Gly
```

-continued

```
                195                 200                 205
Val Pro Gly Ala Gly Val Pro Gly Gly Val Pro Gly Ala Gly Val
210                 215                 220
Pro Gly Gly Gly Val Pro Gly Ala Gly Val Pro Gly Gly Gly Val Pro
225                 230                 235                 240
Gly Ala Gly Val Pro Gly Val Gly Val Pro Gly Ala Gly Val Pro Gly
                245                 250                 255
Gly Gly Val Pro Gly Ala Gly Val Pro Gly Gly Gly Val Pro Gly Ala
            260                 265                 270
Gly Val Pro Gly Gly Gly Val Pro Gly Ala Gly Val Pro Gly Gly Gly
        275                 280                 285
Val Pro Gly Ala Gly Val Pro Gly Gly Gly Val Pro Gly Ala Gly Val
290                 295                 300
Pro Gly Gly Gly Val Pro Gly Ala Gly Val Pro Gly Gly Gly Val Pro
305                 310                 315                 320
Gly Ala Gly Val Pro Gly Val Gly Val Pro Gly Ala Gly Val Pro Gly
                325                 330                 335
Gly Gly Val Pro Gly Ala Gly Val Pro Gly Gly Gly Val Pro Gly Ala
            340                 345                 350
Gly Val Pro Gly Gly Gly Val Pro Gly Ala Gly Val Pro Gly Gly Gly
        355                 360                 365
Val Pro Gly Ala Gly Val Pro Gly Gly Gly Val Pro Gly Ala Gly Val
370                 375                 380
Pro Gly Gly Gly Val Pro Gly Ala Gly Val Pro Gly Gly Gly Val Pro
385                 390                 395                 400
Gly Ala Gly Val Pro Gly Val Gly Val Pro Gly Ala Gly Val Pro Gly
                405                 410                 415
Gly Gly Val Pro Gly Ala Gly Val Pro Gly Gly Gly Val Pro Gly Ala
            420                 425                 430
Gly Val Pro Gly Gly Gly Val Pro Gly Ala Gly Val Pro Gly Gly Gly
        435                 440                 445
Val Pro Gly Ala Gly Val Pro Gly Gly Gly Val Pro Gly Ala Gly Val
450                 455                 460
Pro Gly Gly Gly Val Pro Gly Ala Gly Val Pro Gly Gly Gly Val Pro
465                 470                 475                 480
Gly Ala Gly Val Pro Gly Val Gly Val Pro Gly Ala Gly Val Pro Gly
                485                 490                 495
Gly Gly Val Pro Gly Ala Gly Val Pro Gly Gly Gly Val Pro Gly Ala
            500                 505                 510
Gly Val Pro Gly Gly Gly Val Pro Gly Ala Gly Val Pro Gly Gly Gly
        515                 520                 525
Val Pro Gly Ala Gly Val Pro Gly Gly Gly Val Pro Gly Ala Gly Val
530                 535                 540
Pro Gly Gly Gly Val Pro Gly Ala Gly Val Pro Gly Gly Gly Val Pro
545                 550                 555                 560
Gly Ala Gly Val Pro Gly Val Gly Val Pro Gly Ala Gly Val Pro Gly
                565                 570                 575
Gly Gly Val Pro Gly Ala Gly Val Pro Gly Gly Gly Val Pro Gly Ala
            580                 585                 590
Gly Val Pro Gly Gly Gly Val Pro Gly Ala Gly Val Pro Gly Gly Gly
        595                 600                 605
Val Pro Gly Ala Gly Val Pro Gly Gly Gly Val Pro Gly Ala Gly Val
610                 615                 620
```

-continued

```
Pro Gly Gly Gly Val Pro Gly Ala Gly Val Pro Gly Gly Gly Val Pro
625                 630                 635                 640

Gly Ala Gly Val Pro Gly Val Gly Val Pro Gly Ala Gly Val Pro Gly
                645                 650                 655

Gly Gly Val Pro Gly Ala Gly Val Pro Gly Gly Gly Val Pro Gly Ala
            660                 665                 670

Gly Val Pro Gly Gly Gly Val Pro Gly Ala Gly Val Pro Gly Gly Gly
        675                 680                 685

Val Pro Gly Ala Gly Val Pro Gly Gly Gly Val Pro Gly Ala Gly Val
    690                 695                 700

Pro Gly Gly Gly Val Pro Gly Ala Gly Val Pro Gly Gly Gly Val Pro
705                 710                 715                 720

Gly Ala Gly Val Pro Gly Val Gly Val Pro Gly Ala Gly Val Pro Gly
                725                 730                 735

Gly Gly Val Pro Gly Ala Gly Val Pro Gly Gly Gly Val Pro Gly Ala
            740                 745                 750

Gly Val Pro Gly Gly Gly Val Pro Gly Ala Gly Val Pro Gly Gly Gly
        755                 760                 765

Val Pro Gly Ala Gly Val Pro Gly Gly Gly Val Pro Gly Ala Gly Val
    770                 775                 780

Pro Gly Gly Gly Val Pro Gly Ala Gly Val Pro Gly Gly Gly Val Pro
785                 790                 795                 800

Gly Ala Gly Val Pro Gly Trp Pro
                805

<210> SEQ ID NO 5
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (4)..(4)
<223> OTHER INFORMATION: Xaa can be any naturally occurring amino acid

<400> SEQUENCE: 5

Val Pro Gly Xaa Gly
1               5

<210> SEQ ID NO 6
<211> LENGTH: 780
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
```

-continued

```
<222> LOCATION: (47)..(47)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
```

```
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (192)..(192)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (232)..(232)
<223> OTHER INFORMATION: Xaa can be any naturally occurring amino acid
<220> FEATURE:
<221> NAME/KEY: misc_feature
<222> LOCATION: (237)..(237)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
```

```
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (252)..(252)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (262)..(262)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (272)..(272)
<223> OTHER INFORMATION: Xaa can be any naturally occurring amino acid
<220> FEATURE:
<221> NAME/KEY: misc_feature
<222> LOCATION: (277)..(277)
<223> OTHER INFORMATION: Xaa can be any naturally occurring amino acid
<220> FEATURE:
<221> NAME/KEY: misc_feature
<222> LOCATION: (282)..(282)
<223> OTHER INFORMATION: Xaa can be any naturally occurring amino acid
<220> FEATURE:
<221> NAME/KEY: misc_feature
<222> LOCATION: (287)..(287)
<223> OTHER INFORMATION: Xaa can be any naturally occurring amino acid
<220> FEATURE:
<221> NAME/KEY: misc_feature
<222> LOCATION: (292)..(292)
<223> OTHER INFORMATION: Xaa can be any naturally occurring amino acid
<220> FEATURE:
<221> NAME/KEY: misc_feature
<222> LOCATION: (297)..(297)
<223> OTHER INFORMATION: Xaa can be any naturally occurring amino acid
<220> FEATURE:
<221> NAME/KEY: misc_feature
<222> LOCATION: (302)..(302)
<223> OTHER INFORMATION: Xaa can be any naturally occurring amino acid
<220> FEATURE:
<221> NAME/KEY: misc_feature
<222> LOCATION: (307)..(307)
<223> OTHER INFORMATION: Xaa can be any naturally occurring amino acid
<220> FEATURE:
<221> NAME/KEY: misc_feature
<222> LOCATION: (312)..(312)
<223> OTHER INFORMATION: Xaa can be any naturally occurring amino acid
<220> FEATURE:
<221> NAME/KEY: misc_feature
<222> LOCATION: (317)..(317)
<223> OTHER INFORMATION: Xaa can be any naturally occurring amino acid
<220> FEATURE:
<221> NAME/KEY: misc_feature
<222> LOCATION: (322)..(322)
<223> OTHER INFORMATION: Xaa can be any naturally occurring amino acid
<220> FEATURE:
<221> NAME/KEY: misc_feature
<222> LOCATION: (327)..(327)
<223> OTHER INFORMATION: Xaa can be any naturally occurring amino acid
<220> FEATURE:
<221> NAME/KEY: misc_feature
<222> LOCATION: (332)..(332)
<223> OTHER INFORMATION: Xaa can be any naturally occurring amino acid
<220> FEATURE:
<221> NAME/KEY: misc_feature
<222> LOCATION: (337)..(337)
<223> OTHER INFORMATION: Xaa can be any naturally occurring amino acid
<220> FEATURE:
<221> NAME/KEY: misc_feature
<222> LOCATION: (342)..(342)
```

```
<223> OTHER INFORMATION: Xaa can be any naturally occurring amino acid
<220> FEATURE:
<221> NAME/KEY: misc_feature
<222> LOCATION: (347)..(347)
<223> OTHER INFORMATION: Xaa can be any naturally occurring amino acid
<220> FEATURE:
<221> NAME/KEY: misc_feature
<222> LOCATION: (352)..(352)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (362)..(362)
<223> OTHER INFORMATION: Xaa can be any naturally occurring amino acid
<220> FEATURE:
<221> NAME/KEY: misc_feature
<222> LOCATION: (367)..(367)
<223> OTHER INFORMATION: Xaa can be any naturally occurring amino acid
<220> FEATURE:
<221> NAME/KEY: misc_feature
<222> LOCATION: (372)..(372)
<223> OTHER INFORMATION: Xaa can be any naturally occurring amino acid
<220> FEATURE:
<221> NAME/KEY: misc_feature
<222> LOCATION: (377)..(377)
<223> OTHER INFORMATION: Xaa can be any naturally occurring amino acid
<220> FEATURE:
<221> NAME/KEY: misc_feature
<222> LOCATION: (382)..(382)
<223> OTHER INFORMATION: Xaa can be any naturally occurring amino acid
<220> FEATURE:
<221> NAME/KEY: misc_feature
<222> LOCATION: (387)..(387)
<223> OTHER INFORMATION: Xaa can be any naturally occurring amino acid
<220> FEATURE:
<221> NAME/KEY: misc_feature
<222> LOCATION: (392)..(392)
<223> OTHER INFORMATION: Xaa can be any naturally occurring amino acid
<220> FEATURE:
<221> NAME/KEY: misc_feature
<222> LOCATION: (397)..(397)
<223> OTHER INFORMATION: Xaa can be any naturally occurring amino acid
<220> FEATURE:
<221> NAME/KEY: misc_feature
<222> LOCATION: (402)..(402)
<223> OTHER INFORMATION: Xaa can be any naturally occurring amino acid
<220> FEATURE:
<221> NAME/KEY: misc_feature
<222> LOCATION: (407)..(407)
<223> OTHER INFORMATION: Xaa can be any naturally occurring amino acid
<220> FEATURE:
<221> NAME/KEY: misc_feature
<222> LOCATION: (412)..(412)
<223> OTHER INFORMATION: Xaa can be any naturally occurring amino acid
<220> FEATURE:
<221> NAME/KEY: misc_feature
<222> LOCATION: (417)..(417)
<223> OTHER INFORMATION: Xaa can be any naturally occurring amino acid
<220> FEATURE:
<221> NAME/KEY: misc_feature
<222> LOCATION: (422)..(422)
<223> OTHER INFORMATION: Xaa can be any naturally occurring amino acid
<220> FEATURE:
<221> NAME/KEY: misc_feature
<222> LOCATION: (427)..(427)
<223> OTHER INFORMATION: Xaa can be any naturally occurring amino acid
<220> FEATURE:
<221> NAME/KEY: misc_feature
<222> LOCATION: (432)..(432)
<223> OTHER INFORMATION: Xaa can be any naturally occurring amino acid
<220> FEATURE:
<221> NAME/KEY: misc_feature
<222> LOCATION: (437)..(437)
<223> OTHER INFORMATION: Xaa can be any naturally occurring amino acid
<220> FEATURE:
<221> NAME/KEY: misc_feature
```

```
<222> LOCATION: (442)..(442)
<223> OTHER INFORMATION: Xaa can be any naturally occurring amino acid
<220> FEATURE:
<221> NAME/KEY: misc_feature
<222> LOCATION: (447)..(447)
<223> OTHER INFORMATION: Xaa can be any naturally occurring amino acid
<220> FEATURE:
<221> NAME/KEY: misc_feature
<222> LOCATION: (452)..(452)
<223> OTHER INFORMATION: Xaa can be any naturally occurring amino acid
<220> FEATURE:
<221> NAME/KEY: misc_feature
<222> LOCATION: (457)..(457)
<223> OTHER INFORMATION: Xaa can be any naturally occurring amino acid
<220> FEATURE:
<221> NAME/KEY: misc_feature
<222> LOCATION: (462)..(462)
<223> OTHER INFORMATION: Xaa can be any naturally occurring amino acid
<220> FEATURE:
<221> NAME/KEY: misc_feature
<222> LOCATION: (467)..(467)
<223> OTHER INFORMATION: Xaa can be any naturally occurring amino acid
<220> FEATURE:
<221> NAME/KEY: misc_feature
<222> LOCATION: (472)..(472)
<223> OTHER INFORMATION: Xaa can be any naturally occurring amino acid
<220> FEATURE:
<221> NAME/KEY: misc_feature
<222> LOCATION: (477)..(477)
<223> OTHER INFORMATION: Xaa can be any naturally occurring amino acid
<220> FEATURE:
<221> NAME/KEY: misc_feature
<222> LOCATION: (482)..(482)
<223> OTHER INFORMATION: Xaa can be any naturally occurring amino acid
<220> FEATURE:
<221> NAME/KEY: misc_feature
<222> LOCATION: (487)..(487)
<223> OTHER INFORMATION: Xaa can be any naturally occurring amino acid
<220> FEATURE:
<221> NAME/KEY: misc_feature
<222> LOCATION: (492)..(492)
<223> OTHER INFORMATION: Xaa can be any naturally occurring amino acid
<220> FEATURE:
<221> NAME/KEY: misc_feature
<222> LOCATION: (497)..(497)
<223> OTHER INFORMATION: Xaa can be any naturally occurring amino acid
<220> FEATURE:
<221> NAME/KEY: misc_feature
<222> LOCATION: (502)..(502)
<223> OTHER INFORMATION: Xaa can be any naturally occurring amino acid
<220> FEATURE:
<221> NAME/KEY: misc_feature
<222> LOCATION: (507)..(507)
<223> OTHER INFORMATION: Xaa can be any naturally occurring amino acid
<220> FEATURE:
<221> NAME/KEY: misc_feature
<222> LOCATION: (512)..(512)
<223> OTHER INFORMATION: Xaa can be any naturally occurring amino acid
<220> FEATURE:
<221> NAME/KEY: misc_feature
<222> LOCATION: (517)..(517)
<223> OTHER INFORMATION: Xaa can be any naturally occurring amino acid
<220> FEATURE:
<221> NAME/KEY: misc_feature
<222> LOCATION: (522)..(522)
<223> OTHER INFORMATION: Xaa can be any naturally occurring amino acid
<220> FEATURE:
<221> NAME/KEY: misc_feature
<222> LOCATION: (527)..(527)
<223> OTHER INFORMATION: Xaa can be any naturally occurring amino acid
<220> FEATURE:
<221> NAME/KEY: misc_feature
<222> LOCATION: (532)..(532)
<223> OTHER INFORMATION: Xaa can be any naturally occurring amino acid
<220> FEATURE:
<221> NAME/KEY: misc_feature
<222> LOCATION: (537)..(537)
<223> OTHER INFORMATION: Xaa can be any naturally occurring amino acid
<220> FEATURE:
```

```
<221> NAME/KEY: misc_feature
<222> LOCATION: (542)..(542)
<223> OTHER INFORMATION: Xaa can be any naturally occurring amino acid
<220> FEATURE:
<221> NAME/KEY: misc_feature
<222> LOCATION: (547)..(547)
<223> OTHER INFORMATION: Xaa can be any naturally occurring amino acid
<220> FEATURE:
<221> NAME/KEY: misc_feature
<222> LOCATION: (552)..(552)
<223> OTHER INFORMATION: Xaa can be any naturally occurring amino acid
<220> FEATURE:
<221> NAME/KEY: misc_feature
<222> LOCATION: (557)..(557)
<223> OTHER INFORMATION: Xaa can be any naturally occurring amino acid
<220> FEATURE:
<221> NAME/KEY: misc_feature
<222> LOCATION: (562)..(562)
<223> OTHER INFORMATION: Xaa can be any naturally occurring amino acid
<220> FEATURE:
<221> NAME/KEY: misc_feature
<222> LOCATION: (567)..(567)
<223> OTHER INFORMATION: Xaa can be any naturally occurring amino acid
<220> FEATURE:
<221> NAME/KEY: misc_feature
<222> LOCATION: (572)..(572)
<223> OTHER INFORMATION: Xaa can be any naturally occurring amino acid
<220> FEATURE:
<221> NAME/KEY: misc_feature
<222> LOCATION: (577)..(577)
<223> OTHER INFORMATION: Xaa can be any naturally occurring amino acid
<220> FEATURE:
<221> NAME/KEY: misc_feature
<222> LOCATION: (582)..(582)
<223> OTHER INFORMATION: Xaa can be any naturally occurring amino acid
<220> FEATURE:
<221> NAME/KEY: misc_feature
<222> LOCATION: (587)..(587)
<223> OTHER INFORMATION: Xaa can be any naturally occurring amino acid
<220> FEATURE:
<221> NAME/KEY: misc_feature
<222> LOCATION: (592)..(592)
<223> OTHER INFORMATION: Xaa can be any naturally occurring amino acid
<220> FEATURE:
<221> NAME/KEY: misc_feature
<222> LOCATION: (597)..(597)
<223> OTHER INFORMATION: Xaa can be any naturally occurring amino acid
<220> FEATURE:
<221> NAME/KEY: misc_feature
<222> LOCATION: (602)..(602)
<223> OTHER INFORMATION: Xaa can be any naturally occurring amino acid
<220> FEATURE:
<221> NAME/KEY: misc_feature
<222> LOCATION: (607)..(607)
<223> OTHER INFORMATION: Xaa can be any naturally occurring amino acid
<220> FEATURE:
<221> NAME/KEY: misc_feature
<222> LOCATION: (612)..(612)
<223> OTHER INFORMATION: Xaa can be any naturally occurring amino acid
<220> FEATURE:
<221> NAME/KEY: misc_feature
<222> LOCATION: (617)..(617)
<223> OTHER INFORMATION: Xaa can be any naturally occurring amino acid
<220> FEATURE:
<221> NAME/KEY: misc_feature
<222> LOCATION: (622)..(622)
<223> OTHER INFORMATION: Xaa can be any naturally occurring amino acid
<220> FEATURE:
<221> NAME/KEY: misc_feature
<222> LOCATION: (627)..(627)
<223> OTHER INFORMATION: Xaa can be any naturally occurring amino acid
<220> FEATURE:
<221> NAME/KEY: misc_feature
<222> LOCATION: (632)..(632)
<223> OTHER INFORMATION: Xaa can be any naturally occurring amino acid
<220> FEATURE:
<221> NAME/KEY: misc_feature
<222> LOCATION: (637)..(637)
<223> OTHER INFORMATION: Xaa can be any naturally occurring amino acid
```

```
<220> FEATURE:
<221> NAME/KEY: misc_feature
<222> LOCATION: (642)..(642)
<223> OTHER INFORMATION: Xaa can be any naturally occurring amino acid
<220> FEATURE:
<221> NAME/KEY: misc_feature
<222> LOCATION: (647)..(647)
<223> OTHER INFORMATION: Xaa can be any naturally occurring amino acid
<220> FEATURE:
<221> NAME/KEY: misc_feature
<222> LOCATION: (652)..(652)
<223> OTHER INFORMATION: Xaa can be any naturally occurring amino acid
<220> FEATURE:
<221> NAME/KEY: misc_feature
<222> LOCATION: (657)..(657)
<223> OTHER INFORMATION: Xaa can be any naturally occurring amino acid
<220> FEATURE:
<221> NAME/KEY: misc_feature
<222> LOCATION: (662)..(662)
<223> OTHER INFORMATION: Xaa can be any naturally occurring amino acid
<220> FEATURE:
<221> NAME/KEY: misc_feature
<222> LOCATION: (667)..(667)
<223> OTHER INFORMATION: Xaa can be any naturally occurring amino acid
<220> FEATURE:
<221> NAME/KEY: misc_feature
<222> LOCATION: (672)..(672)
<223> OTHER INFORMATION: Xaa can be any naturally occurring amino acid
<220> FEATURE:
<221> NAME/KEY: misc_feature
<222> LOCATION: (677)..(677)
<223> OTHER INFORMATION: Xaa can be any naturally occurring amino acid
<220> FEATURE:
<221> NAME/KEY: misc_feature
<222> LOCATION: (682)..(682)
<223> OTHER INFORMATION: Xaa can be any naturally occurring amino acid
<220> FEATURE:
<221> NAME/KEY: misc_feature
<222> LOCATION: (687)..(687)
<223> OTHER INFORMATION: Xaa can be any naturally occurring amino acid
<220> FEATURE:
<221> NAME/KEY: misc_feature
<222> LOCATION: (692)..(692)
<223> OTHER INFORMATION: Xaa can be any naturally occurring amino acid
<220> FEATURE:
<221> NAME/KEY: misc_feature
<222> LOCATION: (697)..(697)
<223> OTHER INFORMATION: Xaa can be any naturally occurring amino acid
<220> FEATURE:
<221> NAME/KEY: misc_feature
<222> LOCATION: (702)..(702)
<223> OTHER INFORMATION: Xaa can be any naturally occurring amino acid
<220> FEATURE:
<221> NAME/KEY: misc_feature
<222> LOCATION: (707)..(707)
<223> OTHER INFORMATION: Xaa can be any naturally occurring amino acid
<220> FEATURE:
<221> NAME/KEY: misc_feature
<222> LOCATION: (712)..(712)
<223> OTHER INFORMATION: Xaa can be any naturally occurring amino acid
<220> FEATURE:
<221> NAME/KEY: misc_feature
<222> LOCATION: (717)..(717)
<223> OTHER INFORMATION: Xaa can be any naturally occurring amino acid
<220> FEATURE:
<221> NAME/KEY: misc_feature
<222> LOCATION: (722)..(722)
<223> OTHER INFORMATION: Xaa can be any naturally occurring amino acid
<220> FEATURE:
<221> NAME/KEY: misc_feature
<222> LOCATION: (727)..(727)
<223> OTHER INFORMATION: Xaa can be any naturally occurring amino acid
<220> FEATURE:
<221> NAME/KEY: misc_feature
<222> LOCATION: (732)..(732)
<223> OTHER INFORMATION: Xaa can be any naturally occurring amino acid
<220> FEATURE:
<221> NAME/KEY: misc_feature
<222> LOCATION: (737)..(737)
```

```
<223> OTHER INFORMATION: Xaa can be any naturally occurring amino acid
<220> FEATURE:
<221> NAME/KEY: misc_feature
<222> LOCATION: (742)..(742)
<223> OTHER INFORMATION: Xaa can be any naturally occurring amino acid
<220> FEATURE:
<221> NAME/KEY: misc_feature
<222> LOCATION: (747)..(747)
<223> OTHER INFORMATION: Xaa can be any naturally occurring amino acid
<220> FEATURE:
<221> NAME/KEY: misc_feature
<222> LOCATION: (752)..(752)
<223> OTHER INFORMATION: Xaa can be any naturally occurring amino acid
<220> FEATURE:
<221> NAME/KEY: misc_feature
<222> LOCATION: (757)..(757)
<223> OTHER INFORMATION: Xaa can be any naturally occurring amino acid
<220> FEATURE:
<221> NAME/KEY: misc_feature
<222> LOCATION: (762)..(762)
<223> OTHER INFORMATION: Xaa can be any naturally occurring amino acid
<220> FEATURE:
<221> NAME/KEY: misc_feature
<222> LOCATION: (767)..(767)
<223> OTHER INFORMATION: Xaa can be any naturally occurring amino acid
<220> FEATURE:
<221> NAME/KEY: misc_feature
<222> LOCATION: (772)..(772)
<223> OTHER INFORMATION: Xaa can be any naturally occurring amino acid

<400> SEQUENCE: 6

Arg Gly Gly Arg Leu Ser Tyr Ser Arg Arg Phe Ser Thr Ser Thr
1               5                   10                  15

Gly Arg Gly Pro Gly Val Gly Val Pro Gly Xaa Gly Val Pro Gly Xaa
            20                  25                  30

Gly Val Pro Gly Xaa Gly Val Pro Gly Xaa Gly Val Pro Gly Xaa Gly
        35                  40                  45

Val Pro Gly Xaa Gly Val Pro Gly Xaa Gly Val Pro Gly Xaa Gly Val
    50                  55                  60

Pro Gly Xaa Gly Val Pro Gly Xaa Gly Val Pro Gly Xaa Gly Val Pro
65                  70                  75                  80

Gly Xaa Gly Val Pro Gly Xaa Gly Val Pro Gly Xaa Gly Val Pro Gly
                85                  90                  95

Xaa Gly Val Pro Gly Xaa Gly Val Pro Gly Xaa Gly Val Pro Gly Xaa
            100                 105                 110

Gly Val Pro Gly Xaa Gly Val Pro Gly Xaa Gly Val Pro Gly Xaa Gly
        115                 120                 125

Val Pro Gly Xaa Gly Val Pro Gly Xaa Gly Val Pro Gly Xaa Gly Val
    130                 135                 140

Pro Gly Xaa Gly Val Pro Gly Xaa Gly Val Pro Gly Xaa Gly Val Pro
145                 150                 155                 160

Gly Xaa Gly Val Pro Gly Xaa Gly Val Pro Gly Xaa Gly Val Pro Gly
                165                 170                 175

Xaa Gly Val Pro Gly Xaa Gly Val Pro Gly Xaa Gly Val Pro Gly Xaa
            180                 185                 190

Gly Val Pro Gly Xaa Gly Val Pro Gly Xaa Gly Val Pro Gly Xaa Gly
        195                 200                 205

Val Pro Gly Xaa Gly Val Pro Gly Xaa Gly Val Pro Gly Xaa Gly Val
    210                 215                 220

Pro Gly Xaa Gly Val Pro Gly Xaa Gly Val Pro Gly Xaa Gly Val Pro
225                 230                 235                 240

Gly Xaa Gly Val Pro Gly Xaa Gly Val Pro Gly Xaa Gly Val Pro Gly
                245                 250                 255
```

```
Xaa Gly Val Pro Gly Xaa Gly Val Pro Gly Xaa Gly Val Pro Gly Xaa
            260                 265                 270

Gly Val Pro Gly Xaa Gly Val Pro Gly Xaa Gly Val Pro Gly Xaa Gly
        275                 280                 285

Val Pro Gly Xaa Gly Val Pro Gly Xaa Gly Val Pro Gly Xaa Gly Val
    290                 295                 300

Pro Gly Xaa Gly Val Pro Gly Xaa Gly Val Pro Gly Xaa Gly Val Pro
305                 310                 315                 320

Gly Xaa Gly Val Pro Gly Xaa Gly Val Pro Gly Xaa Gly Val Pro Gly
            325                 330                 335

Xaa Gly Val Pro Gly Xaa Gly Val Pro Gly Xaa Gly Val Pro Gly Xaa
            340                 345                 350

Gly Val Pro Gly Xaa Gly Val Pro Gly Xaa Gly Val Pro Gly Xaa Gly
        355                 360                 365

Val Pro Gly Xaa Gly Val Pro Gly Xaa Gly Val Pro Gly Xaa Gly Val
    370                 375                 380

Pro Gly Xaa Gly Val Pro Gly Xaa Gly Val Pro Gly Xaa Gly Val Pro
385                 390                 395                 400

Gly Xaa Gly Val Pro Gly Xaa Gly Val Pro Gly Xaa Gly Val Pro Gly
            405                 410                 415

Xaa Gly Val Pro Gly Xaa Gly Val Pro Gly Xaa Gly Val Pro Gly Xaa
            420                 425                 430

Gly Val Pro Gly Xaa Gly Val Pro Gly Xaa Gly Val Pro Gly Xaa Gly
        435                 440                 445

Val Pro Gly Xaa Gly Val Pro Gly Xaa Gly Val Pro Gly Xaa Gly Val
    450                 455                 460

Pro Gly Xaa Gly Val Pro Gly Xaa Gly Val Pro Gly Xaa Gly Val Pro
465                 470                 475                 480

Gly Xaa Gly Val Pro Gly Xaa Gly Val Pro Gly Xaa Gly Val Pro Gly
            485                 490                 495

Xaa Gly Val Pro Gly Xaa Gly Val Pro Gly Xaa Gly Val Pro Gly Xaa
            500                 505                 510

Gly Val Pro Gly Xaa Gly Val Pro Gly Xaa Gly Val Pro Gly Xaa Gly
        515                 520                 525

Val Pro Gly Xaa Gly Val Pro Gly Xaa Gly Val Pro Gly Xaa Gly Val
    530                 535                 540

Pro Gly Xaa Gly Val Pro Gly Xaa Gly Val Pro Gly Xaa Gly Val Pro
545                 550                 555                 560

Gly Xaa Gly Val Pro Gly Xaa Gly Val Pro Gly Xaa Gly Val Pro Gly
            565                 570                 575

Xaa Gly Val Pro Gly Xaa Gly Val Pro Gly Xaa Gly Val Pro Gly Xaa
            580                 585                 590

Gly Val Pro Gly Xaa Gly Val Pro Gly Xaa Gly Val Pro Gly Xaa Gly
        595                 600                 605

Val Pro Gly Xaa Gly Val Pro Gly Xaa Gly Val Pro Gly Xaa Gly Val
    610                 615                 620

Pro Gly Xaa Gly Val Pro Gly Xaa Gly Val Pro Gly Xaa Gly Val Pro
625                 630                 635                 640

Gly Xaa Gly Val Pro Gly Xaa Gly Val Pro Gly Xaa Gly Val Pro Gly
            645                 650                 655

Xaa Gly Val Pro Gly Xaa Gly Val Pro Gly Xaa Gly Val Pro Gly Xaa
            660                 665                 670
```

```
Gly Val Pro Gly Xaa Gly Val Pro Gly Xaa Gly Val Pro Gly Xaa Gly
            675                 680                 685
Val Pro Gly Xaa Gly Val Pro Gly Xaa Gly Val Pro Gly Xaa Gly Val
    690                 695                 700
Pro Gly Xaa Gly Val Pro Gly Xaa Gly Val Pro Gly Xaa Gly Val Pro
705                 710                 715                 720
Gly Xaa Gly Val Pro Gly Xaa Gly Val Pro Gly Xaa Gly Val Pro Gly
                725                 730                 735
Xaa Gly Val Pro Gly Xaa Gly Val Pro Gly Xaa Gly Val Pro Gly Xaa
            740                 745                 750
Gly Val Pro Gly Xaa Gly Val Pro Gly Xaa Gly Val Pro Gly Xaa Gly
            755                 760                 765
Val Pro Gly Xaa Gly Trp Pro Gly Ser Gly Gly Cys
    770                 775                 780

<210> SEQ ID NO 7
<211> LENGTH: 830
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (87)..(87)
```

```
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid
<220> FEATURE:
<221> NAME/KEY: misc_feature
```

```
<222> LOCATION: (187)..(187)
<223> OTHER INFORMATION: Xaa can be any naturally occurring amino acid
<220> FEATURE:
<221> NAME/KEY: misc_feature
<222> LOCATION: (192)..(192)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (232)..(232)
<223> OTHER INFORMATION: Xaa can be any naturally occurring amino acid
<220> FEATURE:
<221> NAME/KEY: misc_feature
<222> LOCATION: (237)..(237)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (252)..(252)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (262)..(262)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (272)..(272)
<223> OTHER INFORMATION: Xaa can be any naturally occurring amino acid
<220> FEATURE:
<221> NAME/KEY: misc_feature
<222> LOCATION: (277)..(277)
<223> OTHER INFORMATION: Xaa can be any naturally occurring amino acid
<220> FEATURE:
<221> NAME/KEY: misc_feature
<222> LOCATION: (282)..(282)
<223> OTHER INFORMATION: Xaa can be any naturally occurring amino acid
<220> FEATURE:
```

```
<221> NAME/KEY: misc_feature
<222> LOCATION: (287)..(287)
<223> OTHER INFORMATION: Xaa can be any naturally occurring amino acid
<220> FEATURE:
<221> NAME/KEY: misc_feature
<222> LOCATION: (292)..(292)
<223> OTHER INFORMATION: Xaa can be any naturally occurring amino acid
<220> FEATURE:
<221> NAME/KEY: misc_feature
<222> LOCATION: (297)..(297)
<223> OTHER INFORMATION: Xaa can be any naturally occurring amino acid
<220> FEATURE:
<221> NAME/KEY: misc_feature
<222> LOCATION: (302)..(302)
<223> OTHER INFORMATION: Xaa can be any naturally occurring amino acid
<220> FEATURE:
<221> NAME/KEY: misc_feature
<222> LOCATION: (307)..(307)
<223> OTHER INFORMATION: Xaa can be any naturally occurring amino acid
<220> FEATURE:
<221> NAME/KEY: misc_feature
<222> LOCATION: (312)..(312)
<223> OTHER INFORMATION: Xaa can be any naturally occurring amino acid
<220> FEATURE:
<221> NAME/KEY: misc_feature
<222> LOCATION: (317)..(317)
<223> OTHER INFORMATION: Xaa can be any naturally occurring amino acid
<220> FEATURE:
<221> NAME/KEY: misc_feature
<222> LOCATION: (322)..(322)
<223> OTHER INFORMATION: Xaa can be any naturally occurring amino acid
<220> FEATURE:
<221> NAME/KEY: misc_feature
<222> LOCATION: (327)..(327)
<223> OTHER INFORMATION: Xaa can be any naturally occurring amino acid
<220> FEATURE:
<221> NAME/KEY: misc_feature
<222> LOCATION: (332)..(332)
<223> OTHER INFORMATION: Xaa can be any naturally occurring amino acid
<220> FEATURE:
<221> NAME/KEY: misc_feature
<222> LOCATION: (337)..(337)
<223> OTHER INFORMATION: Xaa can be any naturally occurring amino acid
<220> FEATURE:
<221> NAME/KEY: misc_feature
<222> LOCATION: (342)..(342)
<223> OTHER INFORMATION: Xaa can be any naturally occurring amino acid
<220> FEATURE:
<221> NAME/KEY: misc_feature
<222> LOCATION: (347)..(347)
<223> OTHER INFORMATION: Xaa can be any naturally occurring amino acid
<220> FEATURE:
<221> NAME/KEY: misc_feature
<222> LOCATION: (352)..(352)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (362)..(362)
<223> OTHER INFORMATION: Xaa can be any naturally occurring amino acid
<220> FEATURE:
<221> NAME/KEY: misc_feature
<222> LOCATION: (367)..(367)
<223> OTHER INFORMATION: Xaa can be any naturally occurring amino acid
<220> FEATURE:
<221> NAME/KEY: misc_feature
<222> LOCATION: (372)..(372)
<223> OTHER INFORMATION: Xaa can be any naturally occurring amino acid
<220> FEATURE:
<221> NAME/KEY: misc_feature
<222> LOCATION: (377)..(377)
<223> OTHER INFORMATION: Xaa can be any naturally occurring amino acid
<220> FEATURE:
<221> NAME/KEY: misc_feature
<222> LOCATION: (382)..(382)
<223> OTHER INFORMATION: Xaa can be any naturally occurring amino acid
```

```
<220> FEATURE:
<221> NAME/KEY: misc_feature
<222> LOCATION: (387)..(387)
<223> OTHER INFORMATION: Xaa can be any naturally occurring amino acid
<220> FEATURE:
<221> NAME/KEY: misc_feature
<222> LOCATION: (392)..(392)
<223> OTHER INFORMATION: Xaa can be any naturally occurring amino acid
<220> FEATURE:
<221> NAME/KEY: misc_feature
<222> LOCATION: (397)..(397)
<223> OTHER INFORMATION: Xaa can be any naturally occurring amino acid
<220> FEATURE:
<221> NAME/KEY: misc_feature
<222> LOCATION: (402)..(402)
<223> OTHER INFORMATION: Xaa can be any naturally occurring amino acid
<220> FEATURE:
<221> NAME/KEY: misc_feature
<222> LOCATION: (407)..(407)
<223> OTHER INFORMATION: Xaa can be any naturally occurring amino acid
<220> FEATURE:
<221> NAME/KEY: misc_feature
<222> LOCATION: (412)..(412)
<223> OTHER INFORMATION: Xaa can be any naturally occurring amino acid
<220> FEATURE:
<221> NAME/KEY: misc_feature
<222> LOCATION: (417)..(417)
<223> OTHER INFORMATION: Xaa can be any naturally occurring amino acid
<220> FEATURE:
<221> NAME/KEY: misc_feature
<222> LOCATION: (422)..(422)
<223> OTHER INFORMATION: Xaa can be any naturally occurring amino acid
<220> FEATURE:
<221> NAME/KEY: misc_feature
<222> LOCATION: (427)..(427)
<223> OTHER INFORMATION: Xaa can be any naturally occurring amino acid
<220> FEATURE:
<221> NAME/KEY: misc_feature
<222> LOCATION: (432)..(432)
<223> OTHER INFORMATION: Xaa can be any naturally occurring amino acid
<220> FEATURE:
<221> NAME/KEY: misc_feature
<222> LOCATION: (437)..(437)
<223> OTHER INFORMATION: Xaa can be any naturally occurring amino acid
<220> FEATURE:
<221> NAME/KEY: misc_feature
<222> LOCATION: (442)..(442)
<223> OTHER INFORMATION: Xaa can be any naturally occurring amino acid
<220> FEATURE:
<221> NAME/KEY: misc_feature
<222> LOCATION: (447)..(447)
<223> OTHER INFORMATION: Xaa can be any naturally occurring amino acid
<220> FEATURE:
<221> NAME/KEY: misc_feature
<222> LOCATION: (452)..(452)
<223> OTHER INFORMATION: Xaa can be any naturally occurring amino acid
<220> FEATURE:
<221> NAME/KEY: misc_feature
<222> LOCATION: (457)..(457)
<223> OTHER INFORMATION: Xaa can be any naturally occurring amino acid
<220> FEATURE:
<221> NAME/KEY: misc_feature
<222> LOCATION: (462)..(462)
<223> OTHER INFORMATION: Xaa can be any naturally occurring amino acid
<220> FEATURE:
<221> NAME/KEY: misc_feature
<222> LOCATION: (467)..(467)
<223> OTHER INFORMATION: Xaa can be any naturally occurring amino acid
<220> FEATURE:
<221> NAME/KEY: misc_feature
<222> LOCATION: (472)..(472)
<223> OTHER INFORMATION: Xaa can be any naturally occurring amino acid
<220> FEATURE:
<221> NAME/KEY: misc_feature
<222> LOCATION: (477)..(477)
<223> OTHER INFORMATION: Xaa can be any naturally occurring amino acid
<220> FEATURE:
<221> NAME/KEY: misc_feature
<222> LOCATION: (482)..(482)
```

```
<223> OTHER INFORMATION: Xaa can be any naturally occurring amino acid
<220> FEATURE:
<221> NAME/KEY: misc_feature
<222> LOCATION: (487)..(487)
<223> OTHER INFORMATION: Xaa can be any naturally occurring amino acid
<220> FEATURE:
<221> NAME/KEY: misc_feature
<222> LOCATION: (492)..(492)
<223> OTHER INFORMATION: Xaa can be any naturally occurring amino acid
<220> FEATURE:
<221> NAME/KEY: misc_feature
<222> LOCATION: (497)..(497)
<223> OTHER INFORMATION: Xaa can be any naturally occurring amino acid
<220> FEATURE:
<221> NAME/KEY: misc_feature
<222> LOCATION: (502)..(502)
<223> OTHER INFORMATION: Xaa can be any naturally occurring amino acid
<220> FEATURE:
<221> NAME/KEY: misc_feature
<222> LOCATION: (507)..(507)
<223> OTHER INFORMATION: Xaa can be any naturally occurring amino acid
<220> FEATURE:
<221> NAME/KEY: misc_feature
<222> LOCATION: (512)..(512)
<223> OTHER INFORMATION: Xaa can be any naturally occurring amino acid
<220> FEATURE:
<221> NAME/KEY: misc_feature
<222> LOCATION: (517)..(517)
<223> OTHER INFORMATION: Xaa can be any naturally occurring amino acid
<220> FEATURE:
<221> NAME/KEY: misc_feature
<222> LOCATION: (522)..(522)
<223> OTHER INFORMATION: Xaa can be any naturally occurring amino acid
<220> FEATURE:
<221> NAME/KEY: misc_feature
<222> LOCATION: (527)..(527)
<223> OTHER INFORMATION: Xaa can be any naturally occurring amino acid
<220> FEATURE:
<221> NAME/KEY: misc_feature
<222> LOCATION: (532)..(532)
<223> OTHER INFORMATION: Xaa can be any naturally occurring amino acid
<220> FEATURE:
<221> NAME/KEY: misc_feature
<222> LOCATION: (537)..(537)
<223> OTHER INFORMATION: Xaa can be any naturally occurring amino acid
<220> FEATURE:
<221> NAME/KEY: misc_feature
<222> LOCATION: (542)..(542)
<223> OTHER INFORMATION: Xaa can be any naturally occurring amino acid
<220> FEATURE:
<221> NAME/KEY: misc_feature
<222> LOCATION: (547)..(547)
<223> OTHER INFORMATION: Xaa can be any naturally occurring amino acid
<220> FEATURE:
<221> NAME/KEY: misc_feature
<222> LOCATION: (552)..(552)
<223> OTHER INFORMATION: Xaa can be any naturally occurring amino acid
<220> FEATURE:
<221> NAME/KEY: misc_feature
<222> LOCATION: (557)..(557)
<223> OTHER INFORMATION: Xaa can be any naturally occurring amino acid
<220> FEATURE:
<221> NAME/KEY: misc_feature
<222> LOCATION: (562)..(562)
<223> OTHER INFORMATION: Xaa can be any naturally occurring amino acid
<220> FEATURE:
<221> NAME/KEY: misc_feature
<222> LOCATION: (567)..(567)
<223> OTHER INFORMATION: Xaa can be any naturally occurring amino acid
<220> FEATURE:
<221> NAME/KEY: misc_feature
<222> LOCATION: (572)..(572)
<223> OTHER INFORMATION: Xaa can be any naturally occurring amino acid
<220> FEATURE:
<221> NAME/KEY: misc_feature
<222> LOCATION: (577)..(577)
<223> OTHER INFORMATION: Xaa can be any naturally occurring amino acid
<220> FEATURE:
<221> NAME/KEY: misc_feature
```

```
<222> LOCATION: (582)..(582)
<223> OTHER INFORMATION: Xaa can be any naturally occurring amino acid
<220> FEATURE:
<221> NAME/KEY: misc_feature
<222> LOCATION: (587)..(587)
<223> OTHER INFORMATION: Xaa can be any naturally occurring amino acid
<220> FEATURE:
<221> NAME/KEY: misc_feature
<222> LOCATION: (592)..(592)
<223> OTHER INFORMATION: Xaa can be any naturally occurring amino acid
<220> FEATURE:
<221> NAME/KEY: misc_feature
<222> LOCATION: (597)..(597)
<223> OTHER INFORMATION: Xaa can be any naturally occurring amino acid
<220> FEATURE:
<221> NAME/KEY: misc_feature
<222> LOCATION: (602)..(602)
<223> OTHER INFORMATION: Xaa can be any naturally occurring amino acid
<220> FEATURE:
<221> NAME/KEY: misc_feature
<222> LOCATION: (607)..(607)
<223> OTHER INFORMATION: Xaa can be any naturally occurring amino acid
<220> FEATURE:
<221> NAME/KEY: misc_feature
<222> LOCATION: (612)..(612)
<223> OTHER INFORMATION: Xaa can be any naturally occurring amino acid
<220> FEATURE:
<221> NAME/KEY: misc_feature
<222> LOCATION: (617)..(617)
<223> OTHER INFORMATION: Xaa can be any naturally occurring amino acid
<220> FEATURE:
<221> NAME/KEY: misc_feature
<222> LOCATION: (622)..(622)
<223> OTHER INFORMATION: Xaa can be any naturally occurring amino acid
<220> FEATURE:
<221> NAME/KEY: misc_feature
<222> LOCATION: (627)..(627)
<223> OTHER INFORMATION: Xaa can be any naturally occurring amino acid
<220> FEATURE:
<221> NAME/KEY: misc_feature
<222> LOCATION: (632)..(632)
<223> OTHER INFORMATION: Xaa can be any naturally occurring amino acid
<220> FEATURE:
<221> NAME/KEY: misc_feature
<222> LOCATION: (637)..(637)
<223> OTHER INFORMATION: Xaa can be any naturally occurring amino acid
<220> FEATURE:
<221> NAME/KEY: misc_feature
<222> LOCATION: (642)..(642)
<223> OTHER INFORMATION: Xaa can be any naturally occurring amino acid
<220> FEATURE:
<221> NAME/KEY: misc_feature
<222> LOCATION: (647)..(647)
<223> OTHER INFORMATION: Xaa can be any naturally occurring amino acid
<220> FEATURE:
<221> NAME/KEY: misc_feature
<222> LOCATION: (652)..(652)
<223> OTHER INFORMATION: Xaa can be any naturally occurring amino acid
<220> FEATURE:
<221> NAME/KEY: misc_feature
<222> LOCATION: (657)..(657)
<223> OTHER INFORMATION: Xaa can be any naturally occurring amino acid
<220> FEATURE:
<221> NAME/KEY: misc_feature
<222> LOCATION: (662)..(662)
<223> OTHER INFORMATION: Xaa can be any naturally occurring amino acid
<220> FEATURE:
<221> NAME/KEY: misc_feature
<222> LOCATION: (667)..(667)
<223> OTHER INFORMATION: Xaa can be any naturally occurring amino acid
<220> FEATURE:
<221> NAME/KEY: misc_feature
<222> LOCATION: (672)..(672)
<223> OTHER INFORMATION: Xaa can be any naturally occurring amino acid
<220> FEATURE:
<221> NAME/KEY: misc_feature
<222> LOCATION: (677)..(677)
<223> OTHER INFORMATION: Xaa can be any naturally occurring amino acid
<220> FEATURE:
```

```
<221> NAME/KEY: misc_feature
<222> LOCATION: (682)..(682)
<223> OTHER INFORMATION: Xaa can be any naturally occurring amino acid
<220> FEATURE:
<221> NAME/KEY: misc_feature
<222> LOCATION: (687)..(687)
<223> OTHER INFORMATION: Xaa can be any naturally occurring amino acid
<220> FEATURE:
<221> NAME/KEY: misc_feature
<222> LOCATION: (692)..(692)
<223> OTHER INFORMATION: Xaa can be any naturally occurring amino acid
<220> FEATURE:
<221> NAME/KEY: misc_feature
<222> LOCATION: (697)..(697)
<223> OTHER INFORMATION: Xaa can be any naturally occurring amino acid
<220> FEATURE:
<221> NAME/KEY: misc_feature
<222> LOCATION: (702)..(702)
<223> OTHER INFORMATION: Xaa can be any naturally occurring amino acid
<220> FEATURE:
<221> NAME/KEY: misc_feature
<222> LOCATION: (707)..(707)
<223> OTHER INFORMATION: Xaa can be any naturally occurring amino acid
<220> FEATURE:
<221> NAME/KEY: misc_feature
<222> LOCATION: (712)..(712)
<223> OTHER INFORMATION: Xaa can be any naturally occurring amino acid
<220> FEATURE:
<221> NAME/KEY: misc_feature
<222> LOCATION: (717)..(717)
<223> OTHER INFORMATION: Xaa can be any naturally occurring amino acid
<220> FEATURE:
<221> NAME/KEY: misc_feature
<222> LOCATION: (722)..(722)
<223> OTHER INFORMATION: Xaa can be any naturally occurring amino acid
<220> FEATURE:
<221> NAME/KEY: misc_feature
<222> LOCATION: (727)..(727)
<223> OTHER INFORMATION: Xaa can be any naturally occurring amino acid
<220> FEATURE:
<221> NAME/KEY: misc_feature
<222> LOCATION: (732)..(732)
<223> OTHER INFORMATION: Xaa can be any naturally occurring amino acid
<220> FEATURE:
<221> NAME/KEY: misc_feature
<222> LOCATION: (737)..(737)
<223> OTHER INFORMATION: Xaa can be any naturally occurring amino acid
<220> FEATURE:
<221> NAME/KEY: misc_feature
<222> LOCATION: (742)..(742)
<223> OTHER INFORMATION: Xaa can be any naturally occurring amino acid
<220> FEATURE:
<221> NAME/KEY: misc_feature
<222> LOCATION: (747)..(747)
<223> OTHER INFORMATION: Xaa can be any naturally occurring amino acid
<220> FEATURE:
<221> NAME/KEY: misc_feature
<222> LOCATION: (752)..(752)
<223> OTHER INFORMATION: Xaa can be any naturally occurring amino acid
<220> FEATURE:
<221> NAME/KEY: misc_feature
<222> LOCATION: (757)..(757)
<223> OTHER INFORMATION: Xaa can be any naturally occurring amino acid
<220> FEATURE:
<221> NAME/KEY: misc_feature
<222> LOCATION: (762)..(762)
<223> OTHER INFORMATION: Xaa can be any naturally occurring amino acid
<220> FEATURE:
<221> NAME/KEY: misc_feature
<222> LOCATION: (767)..(767)
<223> OTHER INFORMATION: Xaa can be any naturally occurring amino acid
<220> FEATURE:
<221> NAME/KEY: misc_feature
<222> LOCATION: (772)..(772)
<223> OTHER INFORMATION: Xaa can be any naturally occurring amino acid
<220> FEATURE:
<221> NAME/KEY: misc_feature
<222> LOCATION: (777)..(777)
<223> OTHER INFORMATION: Xaa can be any naturally occurring amino acid
```

```
<220> FEATURE:
<221> NAME/KEY: misc_feature
<222> LOCATION: (782)..(782)
<223> OTHER INFORMATION: Xaa can be any naturally occurring amino acid
<220> FEATURE:
<221> NAME/KEY: misc_feature
<222> LOCATION: (787)..(787)
<223> OTHER INFORMATION: Xaa can be any naturally occurring amino acid
<220> FEATURE:
<221> NAME/KEY: misc_feature
<222> LOCATION: (792)..(792)
<223> OTHER INFORMATION: Xaa can be any naturally occurring amino acid
<220> FEATURE:
<221> NAME/KEY: misc_feature
<222> LOCATION: (797)..(797)
<223> OTHER INFORMATION: Xaa can be any naturally occurring amino acid
<220> FEATURE:
<221> NAME/KEY: misc_feature
<222> LOCATION: (802)..(802)
<223> OTHER INFORMATION: Xaa can be any naturally occurring amino acid
<220> FEATURE:
<221> NAME/KEY: misc_feature
<222> LOCATION: (807)..(807)
<223> OTHER INFORMATION: Xaa can be any naturally occurring amino acid
<220> FEATURE:
<221> NAME/KEY: misc_feature
<222> LOCATION: (812)..(812)
<223> OTHER INFORMATION: Xaa can be any naturally occurring amino acid
<220> FEATURE:
<221> NAME/KEY: misc_feature
<222> LOCATION: (817)..(817)
<223> OTHER INFORMATION: Xaa can be any naturally occurring amino acid
<220> FEATURE:
<221> NAME/KEY: misc_feature
<222> LOCATION: (822)..(822)
<223> OTHER INFORMATION: Xaa can be any naturally occurring amino acid

<400> SEQUENCE: 7

Arg Gly Gly Arg Leu Ser Tyr Ser Arg Arg Phe Ser Thr Ser Thr
1               5                   10                  15

Gly Arg Gly Pro Gly Val Gly Val Pro Gly Xaa Gly Val Pro Gly Xaa
            20                  25                  30

Gly Val Pro Gly Xaa Gly Val Pro Gly Xaa Gly Val Pro Gly Xaa Gly
        35                  40                  45

Val Pro Gly Xaa Gly Val Pro Gly Xaa Gly Val Pro Gly Xaa Gly Val
50                  55                  60

Pro Gly Xaa Gly Val Pro Gly Xaa Gly Val Pro Gly Xaa Gly Val Pro
65                  70                  75                  80

Gly Xaa Gly Val Pro Gly Xaa Gly Val Pro Gly Xaa Gly Val Pro Gly
                85                  90                  95

Xaa Gly Val Pro Gly Xaa Gly Val Pro Gly Xaa Gly Val Pro Gly Xaa
            100                 105                 110

Gly Val Pro Gly Xaa Gly Val Pro Gly Xaa Gly Val Pro Gly Xaa Gly
        115                 120                 125

Val Pro Gly Xaa Gly Val Pro Gly Xaa Gly Val Pro Gly Xaa Gly Val
    130                 135                 140

Pro Gly Xaa Gly Val Pro Gly Xaa Gly Val Pro Gly Xaa Gly Val Pro
145                 150                 155                 160

Gly Xaa Gly Val Pro Gly Xaa Gly Val Pro Gly Xaa Gly Val Pro Gly
                165                 170                 175

Xaa Gly Val Pro Gly Xaa Gly Val Pro Gly Xaa Gly Val Pro Gly Xaa
            180                 185                 190

Gly Val Pro Gly Xaa Gly Val Pro Gly Xaa Gly Val Pro Gly Xaa Gly
        195                 200                 205

Val Pro Gly Xaa Gly Val Pro Gly Xaa Gly Val Pro Gly Xaa Gly Val
```

```
                210                 215                 220

Pro Gly Xaa Gly Val Pro Gly Xaa Gly Val Pro Gly Xaa Gly Val Pro
225                 230                 235                 240

Gly Xaa Gly Val Pro Gly Xaa Gly Val Pro Gly Xaa Gly Val Pro Gly
                245                 250                 255

Xaa Gly Val Pro Gly Xaa Gly Val Pro Gly Xaa Gly Val Pro Gly Xaa
            260                 265                 270

Gly Val Pro Gly Xaa Gly Val Pro Gly Xaa Gly Val Pro Gly Xaa Gly
        275                 280                 285

Val Pro Gly Xaa Gly Val Pro Gly Xaa Gly Val Pro Gly Xaa Gly Val
    290                 295                 300

Pro Gly Xaa Gly Val Pro Gly Xaa Gly Val Pro Gly Xaa Gly Val Pro
305                 310                 315                 320

Gly Xaa Gly Val Pro Gly Xaa Gly Val Pro Gly Xaa Gly Val Pro Gly
                325                 330                 335

Xaa Gly Val Pro Gly Xaa Gly Val Pro Gly Xaa Gly Val Pro Gly Xaa
            340                 345                 350

Gly Val Pro Gly Xaa Gly Val Pro Gly Xaa Gly Val Pro Gly Xaa Gly
        355                 360                 365

Val Pro Gly Xaa Gly Val Pro Gly Xaa Gly Val Pro Gly Xaa Gly Val
    370                 375                 380

Pro Gly Xaa Gly Val Pro Gly Xaa Gly Val Pro Gly Xaa Gly Val Pro
385                 390                 395                 400

Gly Xaa Gly Val Pro Gly Xaa Gly Val Pro Gly Xaa Gly Val Pro Gly
                405                 410                 415

Xaa Gly Val Pro Gly Xaa Gly Val Pro Gly Xaa Gly Val Pro Gly Xaa
            420                 425                 430

Gly Val Pro Gly Xaa Gly Val Pro Gly Xaa Gly Val Pro Gly Xaa Gly
        435                 440                 445

Val Pro Gly Xaa Gly Val Pro Gly Xaa Gly Val Pro Gly Xaa Gly Val
    450                 455                 460

Pro Gly Xaa Gly Val Pro Gly Xaa Gly Val Pro Gly Xaa Gly Val Pro
465                 470                 475                 480

Gly Xaa Gly Val Pro Gly Xaa Gly Val Pro Gly Xaa Gly Val Pro Gly
                485                 490                 495

Xaa Gly Val Pro Gly Xaa Gly Val Pro Gly Xaa Gly Val Pro Gly Xaa
            500                 505                 510

Gly Val Pro Gly Xaa Gly Val Pro Gly Xaa Gly Val Pro Gly Xaa Gly
        515                 520                 525

Val Pro Gly Xaa Gly Val Pro Gly Xaa Gly Val Pro Gly Xaa Gly Val
    530                 535                 540

Pro Gly Xaa Gly Val Pro Gly Xaa Gly Val Pro Gly Xaa Gly Val Pro
545                 550                 555                 560

Gly Xaa Gly Val Pro Gly Xaa Gly Val Pro Gly Xaa Gly Val Pro Gly
                565                 570                 575

Xaa Gly Val Pro Gly Xaa Gly Val Pro Gly Xaa Gly Val Pro Gly Xaa
            580                 585                 590

Gly Val Pro Gly Xaa Gly Val Pro Gly Xaa Gly Val Pro Gly Xaa Gly
        595                 600                 605

Val Pro Gly Xaa Gly Val Pro Gly Xaa Gly Val Pro Gly Xaa Gly Val
    610                 615                 620

Pro Gly Xaa Gly Val Pro Gly Xaa Gly Val Pro Gly Xaa Gly Val Pro
625                 630                 635                 640
```

```
Gly Xaa Gly Val Pro Gly Xaa Gly Val Pro Gly Xaa Gly Val Pro Gly
            645                 650                 655

Xaa Gly Val Pro Gly Xaa Gly Val Pro Gly Xaa Gly Val Pro Gly Xaa
            660                 665                 670

Gly Val Pro Gly Xaa Gly Val Pro Gly Xaa Gly Val Pro Gly Xaa Gly
            675                 680                 685

Val Pro Gly Xaa Gly Val Pro Gly Xaa Gly Val Pro Gly Xaa Gly Val
            690                 695                 700

Pro Gly Xaa Gly Val Pro Gly Xaa Gly Val Pro Gly Xaa Gly Val Pro
705                 710                 715                 720

Gly Xaa Gly Val Pro Gly Xaa Gly Val Pro Gly Xaa Gly Val Pro Gly
            725                 730                 735

Xaa Gly Val Pro Gly Xaa Gly Val Pro Gly Xaa Gly Val Pro Gly Xaa
            740                 745                 750

Gly Val Pro Gly Xaa Gly Val Pro Gly Xaa Gly Val Pro Gly Xaa Gly
            755                 760                 765

Val Pro Gly Xaa Gly Val Pro Gly Xaa Gly Val Pro Gly Xaa Gly Val
            770                 775                 780

Pro Gly Xaa Gly Val Pro Gly Xaa Gly Val Pro Gly Xaa Gly Val Pro
785                 790                 795                 800

Gly Xaa Gly Val Pro Gly Xaa Gly Val Pro Gly Xaa Gly Val Pro Gly
            805                 810                 815

Xaa Gly Val Pro Gly Xaa Gly Trp Pro Gly Ser Gly Gly Cys
            820                 825                 830

<210> SEQ ID NO 8
<211> LENGTH: 11
<212> TYPE: PRT
<213> ORGANISM: Artificial Sequence
<220> FEATURE:
<223> OTHER INFORMATION: Synthesized

<400> SEQUENCE: 8

Tyr Gly Arg Lys Lys Arg Arg Gln Arg Arg
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Synthesized

<400> SEQUENCE: 9

Arg Gln Ile Lys Ile Trp Phe Gln Asn Arg Arg Met Lys Trp Lys Lys
1               5                   10                  15

<210> SEQ ID NO 10
<211> LENGTH: 24
<212> TYPE: PRT
<213> ORGANISM: Artificial Sequence
<220> FEATURE:
<223> OTHER INFORMATION: Synthesized

<400> SEQUENCE: 10

Arg Arg Ile Arg Pro Arg Pro Pro Arg Leu Pro Arg Pro Arg Pro Arg
1               5                   10                  15

Pro Leu Pro Phe Pro Arg Pro Gly
            20
```

```
<210> SEQ ID NO 11
<211> LENGTH: 18
<212> TYPE: PRT
<213> ORGANISM: Artificial Sequence
<220> FEATURE:
<223> OTHER INFORMATION: Synthesized

<400> SEQUENCE: 11

Arg Gly Gly Arg Leu Ser Tyr Ser Arg Arg Phe Ser Thr Ser Thr
1               5                   10                  15

Gly Arg

<210> SEQ ID NO 12
<211> LENGTH: 7
<212> TYPE: PRT
<213> ORGANISM: Artificial Sequence
<220> FEATURE:
<223> OTHER INFORMATION: Synthesized

<400> SEQUENCE: 12

Arg Arg Arg Arg Arg Arg Arg
1               5

<210> SEQ ID NO 13
<211> LENGTH: 8
<212> TYPE: PRT
<213> ORGANISM: Artificial Sequence
<220> FEATURE:
<223> OTHER INFORMATION: Synthesized

<400> SEQUENCE: 13

Arg Arg Arg Arg Arg Arg Arg Arg
1               5

<210> SEQ ID NO 14
<211> LENGTH: 9
<212> TYPE: PRT
<213> ORGANISM: Artificial Sequence
<220> FEATURE:
<223> OTHER INFORMATION: Synthesized

<400> SEQUENCE: 14

Arg Arg Arg Arg Arg Arg Arg Arg Arg
1               5

<210> SEQ ID NO 15
<211> LENGTH: 10
<212> TYPE: PRT
<213> ORGANISM: Artificial Sequence
<220> FEATURE:
<223> OTHER INFORMATION: Synthesized

<400> SEQUENCE: 15

Arg Arg Arg Arg Arg Arg Arg Arg Arg Arg
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthesized

<400> SEQUENCE: 16

Arg Arg Arg Arg Arg Arg Arg Arg Arg Arg Arg
1               5                   10
```

<210> SEQ ID NO 17
<211> LENGTH: 34
<212> TYPE: PRT
<213> ORGANISM: Artificial Sequence
<220> FEATURE:
<223> OTHER INFORMATION: Synthesized

<400> SEQUENCE: 17

Asp Ala Ala Thr Ala Thr Arg Gly Arg Ser Ala Ser Arg Pro Thr
1               5                   10                  15
Gln Arg Pro Arg Ala Pro Ala Arg Ser Ala Ser Arg Pro Arg Arg Pro
            20                  25                  30
Val Gln

<210> SEQ ID NO 18
<211> LENGTH: 27
<212> TYPE: PRT
<213> ORGANISM: Artificial Sequence
<220> FEATURE:
<223> OTHER INFORMATION: Synthesized

<400> SEQUENCE: 18

Gly Trp Thr Leu Asn Ser Ala Gly Tyr Leu Leu Gly Lys Ile Asn Leu
1               5                   10                  15
Lys Ala Leu Ala Ala Leu Ala Lys Lys Ile Leu
            20                  25

<210> SEQ ID NO 19
<211> LENGTH: 18
<212> TYPE: PRT
<213> ORGANISM: Artificial Sequence
<220> FEATURE:
<223> OTHER INFORMATION: Synthesized

<400> SEQUENCE: 19

Lys Leu Ala Leu Lys Leu Ala Leu Lys Ala Leu Lys Ala Ala Leu Lys
1               5                   10                  15
Leu Ala

<210> SEQ ID NO 20
<211> LENGTH: 18
<212> TYPE: PRT
<213> ORGANISM: Artificial Sequence
<220> FEATURE:
<223> OTHER INFORMATION: Synthesized

<400> SEQUENCE: 20

Leu Leu Ile Ile Leu Arg Arg Arg Ile Arg Lys Gln Ala His Ala His
1               5                   10                  15
Ser Lys

<210> SEQ ID NO 21
<211> LENGTH: 15
<212> TYPE: PRT
<213> ORGANISM: Artificial Sequence
<220> FEATURE:
<223> OTHER INFORMATION: Synthesized

<400> SEQUENCE: 21

Ala Ala Val Ala Leu Leu Pro Ala Val Leu Leu Ala Leu Leu Pro
1               5                   10                  15

```
<210> SEQ ID NO 22
<211> LENGTH: 24
<212> TYPE: PRT
<213> ORGANISM: Artificial Sequence
<220> FEATURE:
<223> OTHER INFORMATION: Synthesized

<400> SEQUENCE: 22

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 23
<211> LENGTH: 27
<212> TYPE: PRT
<213> ORGANISM: Artificial Sequence
<220> FEATURE:
<223> OTHER INFORMATION: Synthesized

<400> SEQUENCE: 23

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 24
<211> LENGTH: 21
<212> TYPE: PRT
<213> ORGANISM: Artificial Sequence
<220> FEATURE:
<223> OTHER INFORMATION: Synthesized

<400> SEQUENCE: 24

Thr Arg Ser Ser Arg Ala Gly Leu Gln Phe Pro Val Gly Arg Val His
1               5                   10                  15

Arg Leu Leu Arg Lys
            20

<210> SEQ ID NO 25
<211> LENGTH: 21
<212> TYPE: PRT
<213> ORGANISM: Artificial Sequence
<220> FEATURE:
<223> OTHER INFORMATION: Synthesized

<400> SEQUENCE: 25

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 26
<211> LENGTH: 23
<212> TYPE: PRT
<213> ORGANISM: Artificial Sequence
<220> FEATURE:
<223> OTHER INFORMATION: Synthesized

<400> SEQUENCE: 26

Gly Ile Gly Lys Phe Leu His Ser Ala Lys Lys Phe Gly Lys Ala Phe
1               5                   10                  15

Val Gly Glu Ile Met Asn Ser
            20
```

```
<210> SEQ ID NO 27
<211> LENGTH: 8
<212> TYPE: PRT
<213> ORGANISM: Artificial Sequence
<220> FEATURE:
<223> OTHER INFORMATION: Synthesized

<400> SEQUENCE: 27

Gly Arg Lys Arg Lys Lys Arg Thr
1               5

<210> SEQ ID NO 28
<211> LENGTH: 21
<212> TYPE: PRT
<213> ORGANISM: Artificial Sequence
<220> FEATURE:
<223> OTHER INFORMATION: Synthesized

<400> SEQUENCE: 28

Val Thr Val Leu Phe Arg Arg Leu Arg Ile Arg Arg Ala Ser Gly Pro
1               5                   10                  15

Pro Arg Val Arg Val
            20

<210> SEQ ID NO 29
<211> LENGTH: 20
<212> TYPE: PRT
<213> ORGANISM: Artificial Sequence
<220> FEATURE:
<223> OTHER INFORMATION: Synthesized

<400> SEQUENCE: 29

Phe His Cys Val Pro Arg Asp Leu Ser Trp Leu Asp Leu Glu Ala Asn
1               5                   10                  15

Met Cys Leu Pro
            20

<210> SEQ ID NO 30
<211> LENGTH: 17
<212> TYPE: PRT
<213> ORGANISM: Artificial Sequence
<220> FEATURE:
<223> OTHER INFORMATION: Synthesized

<400> SEQUENCE: 30

Thr Tyr Ala Asp Phe Ile Ala Ser Gly Arg Thr Gly Arg Arg Asn Ala
1               5                   10                  15

Ile

<210> SEQ ID NO 31
<211> LENGTH: 12
<212> TYPE: PRT
<213> ORGANISM: Artificial sequence
<220> FEATURE:
<223> OTHER INFORMATION: Synthesized

<400> SEQUENCE: 31

Thr Arg Thr Lys Ile Asp Trp Asn Lys Ile Leu Ser
1               5                   10

<210> SEQ ID NO 32
<211> LENGTH: 133
<212> TYPE: PRT
<213> ORGANISM: artificial sequence
<220> FEATURE:
```

<223> OTHER INFORMATION: Synthesized

<400> SEQUENCE: 32

Gly Ser Pro Ala Ala Pro Pro Thr Leu Pro Pro Tyr Phe Met Lys
1               5                   10                  15

Gly Ser Ile Ile Gln Leu Ala Asn Gly Glu Leu Lys Lys Val Glu Asp
            20                  25                  30

Leu Lys Thr Glu Asp Phe Ile Gln Ser Ala Glu Ile Ser Asn Asp Leu
        35                  40                  45

Lys Ile Asp Ser Ser Thr Val Glu Arg Ile Glu Asp Ser His Ser Pro
    50                  55                  60

Gly Val Ala Val Ile Gln Phe Ala Val Gly Glu His Arg Ala Gln Val
65                  70                  75                  80

Ser Val Glu Val Leu Val Glu Tyr Pro Phe Phe Val Phe Gly Gln Gly
                85                  90                  95

Trp Ser Ser Cys Cys Pro Glu Arg Thr Ser Gln Leu Phe Asp Leu Pro
            100                 105                 110

Cys Ser Lys Leu Ser Val Gly Asp Val Cys Ile Ser Leu Thr Leu Lys
        115                 120                 125

Asn Leu Lys Asn Gly
    130

<210> SEQ ID NO 33
<211> LENGTH: 40
<212> TYPE: PRT
<213> ORGANISM: Artificial Sequence
<220> FEATURE:
<223> OTHER INFORMATION: Synthesized

<400> SEQUENCE: 33

Glu Asp Cys Ile Pro Lys Trp Lys Gly Cys Val Asn Arg His Gly Asp
1               5                   10                  15

Cys Cys Glu Gly Leu Glu Cys Trp Lys Arg Arg Arg Ser Phe Glu Val
            20                  25                  30

Cys Val Pro Lys Thr Pro Lys Thr
        35                  40

<210> SEQ ID NO 34
<211> LENGTH: 11
<212> TYPE: PRT
<213> ORGANISM: Artificial sequence
<220> FEATURE:
<223> OTHER INFORMATION: Synthesized

<400> SEQUENCE: 34

Val Asp Pro Val Asn Phe Lys Leu Leu Ser His
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthesized

<400> SEQUENCE: 35

Arg Val Asp Pro Val Asn Phe Lys Leu Leu Ser His
1               5                   10

<210> SEQ ID NO 36
<211> LENGTH: 25

<212> TYPE: PRT
<213> ORGANISM: Artificial Sequence
<220> FEATURE:
<223> OTHER INFORMATION: Synthesized

<400> SEQUENCE: 36

Arg Lys Arg Arg Lys Arg Val Asn Thr Lys Arg Ser Ser Arg Ala Phe
1               5                   10                  15

Arg Ala Asn Leu Lys Thr Pro Leu Lys
            20                  25

<210> SEQ ID NO 37
<211> LENGTH: 28
<212> TYPE: PRT
<213> ORGANISM: Artificial sequence
<220> FEATURE:
<223> OTHER INFORMATION: Synthesized

<400> SEQUENCE: 37

Ser Asn Pro Asp Ser Pro Ala Lys Pro Glu Lys Asn Gly His Ala Lys
1               5                   10                  15

Ile Val Asn Pro Arg Ile Ala Lys Phe Phe Glu Ile
            20                  25

<210> SEQ ID NO 38
<211> LENGTH: 30
<212> TYPE: PRT
<213> ORGANISM: Artificial sequence
<220> FEATURE:
<223> OTHER INFORMATION: Synthesized

<400> SEQUENCE: 38

Gln Thr Met Pro Asn Gly Lys Thr Arg Thr Ser Leu Lys Thr Met Ser
1               5                   10                  15

Arg Arg Lys Leu Ser Gln Gln Lys Glu Lys Lys Ala Thr Gln
            20                  25                  30

<210> SEQ ID NO 39
<211> LENGTH: 58
<212> TYPE: PRT
<213> ORGANISM: Artificial Sequence
<220> FEATURE:
<223> OTHER INFORMATION: Synthesized

<400> SEQUENCE: 39

Ser Asn Pro Asp Ser Pro Ala Lys Pro Glu Lys Asn Gly His Ala Lys
1               5                   10                  15

Ile Val Asn Pro Arg Ile Ala Lys Phe Phe Glu Ile Gln Thr Met Pro
            20                  25                  30

Asn Gly Lys Thr Arg Thr Ser Leu Lys Thr Met Ser Arg Arg Lys Leu
        35                  40                  45

Ser Gln Gln Lys Glu Lys Lys Ala Thr Gln
    50                  55

<210> SEQ ID NO 40
<211> LENGTH: 129
<212> TYPE: PRT
<213> ORGANISM: Artificial sequence
<220> FEATURE:
<223> OTHER INFORMATION: Synthesized

<400> SEQUENCE: 40

Arg Lys Arg Arg Lys Arg Val Asn Thr Lys Arg Ser Ser Arg Ala Phe
1               5                   10                  15

```
Arg Ala Asn Leu Lys Thr Pro Leu Lys Asp Ala Ala Arg Arg Ala Gln
             20                  25                  30

Glu Leu Glu Met Glu Met Leu Ser Ser Thr Ser Pro Pro Glu Arg Thr
             35                  40                  45

Arg Tyr Ser Pro Ile Pro Pro Ser His His Gln Leu Thr Leu Pro Asp
             50                  55                  60

Pro Ser His His Gly Leu His Ser Asn Pro Asp Ser Pro Ala Lys Pro
 65                  70                  75                  80

Glu Lys Asn Gly His Ala Lys Ile Val Asn Pro Arg Ile Ala Lys Phe
                 85                  90                  95

Phe Glu Ile Gln Thr Met Pro Asn Gly Lys Thr Arg Thr Ser Leu Lys
             100                 105                 110

Thr Met Ser Arg Arg Lys Leu Ser Gln Gln Lys Glu Lys Lys Ala Thr
             115                 120                 125

Gln

<210> SEQ ID NO 41
<211> LENGTH: 6
<212> TYPE: PRT
<213> ORGANISM: Artificial Sequence
<220> FEATURE:
<223> OTHER INFORMATION: Synthesized

<400> SEQUENCE: 41

Trp Pro Gly Ser Gly Gly
1               5
```